US012036053B2

(12) United States Patent
Takata et al.

(10) Patent No.: US 12,036,053 B2
(45) Date of Patent: Jul. 16, 2024

(54) RADIODIAGNOSTIC APPARATUS AND METHOD OF OPERATING RADIODIAGNOSTIC APPARATUS

(71) Applicant: FUJIFILM CORPORATION, Tokyo (JP)

(72) Inventors: Kenji Takata, Kanagawa (JP); Yoshihiro Nishi, Kanagawa (JP); Keiji Tsubota, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 498 days.

(21) Appl. No.: 17/358,054

(22) Filed: Jun. 25, 2021

(65) Prior Publication Data

US 2022/0047229 A1 Feb. 17, 2022

(30) Foreign Application Priority Data

Aug. 17, 2020 (JP) .................. 2020-137646
Nov. 24, 2020 (JP) .................. 2020-194559

(51) Int. Cl.
*A61B 6/04* (2006.01)
*A61B 6/00* (2024.01)
*A61L 2/10* (2006.01)

(52) U.S. Cl.
CPC .......... *A61B 6/0435* (2013.01); *A61B 6/0414* (2013.01); *A61B 6/4452* (2013.01);
(Continued)

(58) Field of Classification Search
CPC ....... A61B 6/0414; A61B 6/0435; A61B 6/10; A61B 6/4423; A61B 6/4441;
(Continued)

(56) References Cited

U.S. PATENT DOCUMENTS

2013/0117959 A1* 5/2013 Stryker ............... A47L 11/4088
15/319
2014/0016851 A1* 1/2014 Nakano ................ A61B 6/5241
382/131
(Continued)

FOREIGN PATENT DOCUMENTS

JP H09-253083 A 9/1997
JP 2008-513090 A 5/2008
(Continued)

OTHER PUBLICATIONS

English language translation of the following: Office action dated Apr. 4, 2023 from the JPO in a Japanese patent application No. 2020-194559 corresponding to the instant patent application. This office action translation is submitted now in order to supplement the understanding of the cited references which are being disclosed in the instant Information Disclosure Statement.

*Primary Examiner* — Mark R Gaworecki
(74) *Attorney, Agent, or Firm* — SOLARIS Intellectual Property Group, PLLC

(57) ABSTRACT

A breast imaging apparatus includes a radiation source that irradiates a breast of a subject with radiation, a radiation detector that detects the radiation transmitted through the breast to output a radiographic image, an ultraviolet light source that performs irradiation of ultraviolet light, and a controller that controls an operation of the ultraviolet light source. The controller prohibits the irradiation of the ultraviolet light by the ultraviolet light source in a case where a predetermined set condition is satisfied. The controller determines that the set condition is satisfied, for example, in a case where a person is shown in a captured image of a camera.

26 Claims, 54 Drawing Sheets

(52) U.S. Cl.
CPC .............. *A61L 2/10* (2013.01); *A61L 2202/11* (2013.01); *A61L 2202/24* (2013.01)

(58) Field of Classification Search
CPC ..... A61B 6/4452; A61B 6/4464; A61B 6/502; A61L 2/10; A61L 2/24; A61L 2202/11; A61L 2202/14; A61L 2202/24
See application file for complete search history.

(56) References Cited

U.S. PATENT DOCUMENTS

| | | | |
|---|---|---|---|
| 2016/0158082 A1* | 6/2016 | Gainor | A61G 13/107 5/690 |
| 2016/0271803 A1* | 9/2016 | Stewart | B25J 11/0085 |
| 2019/0083202 A1* | 3/2019 | Brawn | A61C 8/0006 |

FOREIGN PATENT DOCUMENTS

| | | | | |
|---|---|---|---|---|
| KR | 10-2014-0118694 A | 10/2014 | | |
| WO | WO-2017020028 A1 * | 2/2017 | ............... | A23L 3/28 |
| WO | 2019/182077 A1 | 9/2019 | | |

* cited by examiner

FIG. 13

IRRADIATION CONDITION TABLE 66

| IMAGING METHOD | BREAST SIZE | BREAST SHAPE | IRRADIATION CONDITION (TUBE VOLTAGE, TUBE CURRENT, IRRADIATION TIME, IRRADIATION FIELD SIZE) |
|---|---|---|---|
| CC_A IMAGING | LARGE | CIRCULAR | 50 KV  10 mA  0.5 ms  50 cm × 50 cm — 81 |
| | | HORIZONTALLY LONG | 52 KV  12 mA  0.5 ms  60 cm × 50 cm |
| | | VERTICALLY LONG | 52 KV  12 mA  0.5 ms  50 cm × 60 cm |
| | MIDDLE | CIRCULAR | 45 KV  9 mA  0.5 ms  45 cm × 45 cm |
| CO_B IMAGING | SMALL | VERTICALLY LONG | 40 KV  6 mA  0.5 ms  40 cm × 45 cm |
| MLO IMAGING | LARGE | CIRCULAR | 55 KV  12 mA  0.5 ms  50 cm × 50 cm |

FIG. 16
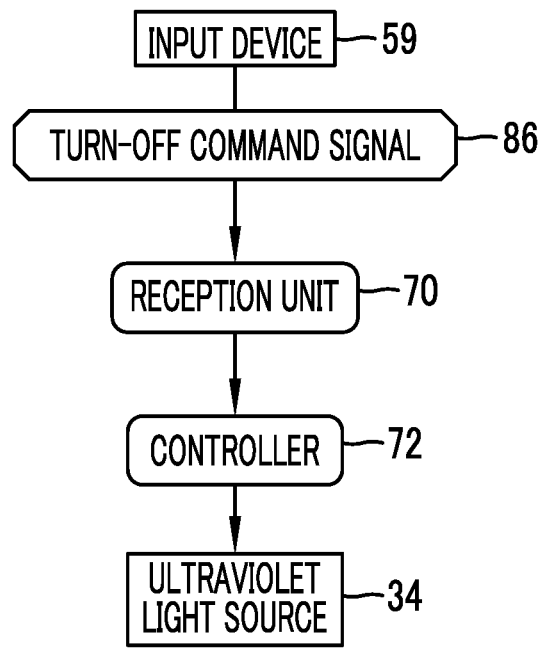
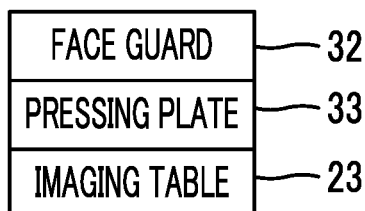
FIG. 17
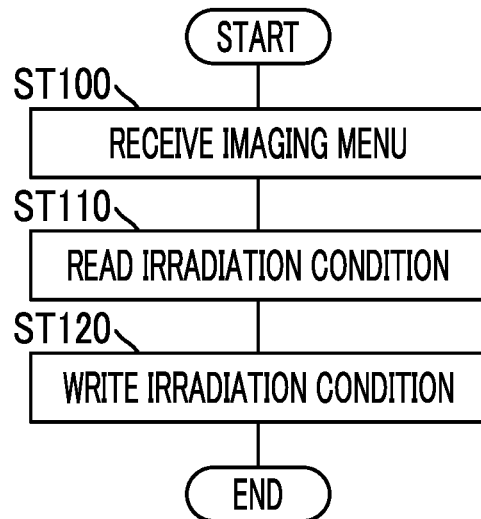

FIG. 25
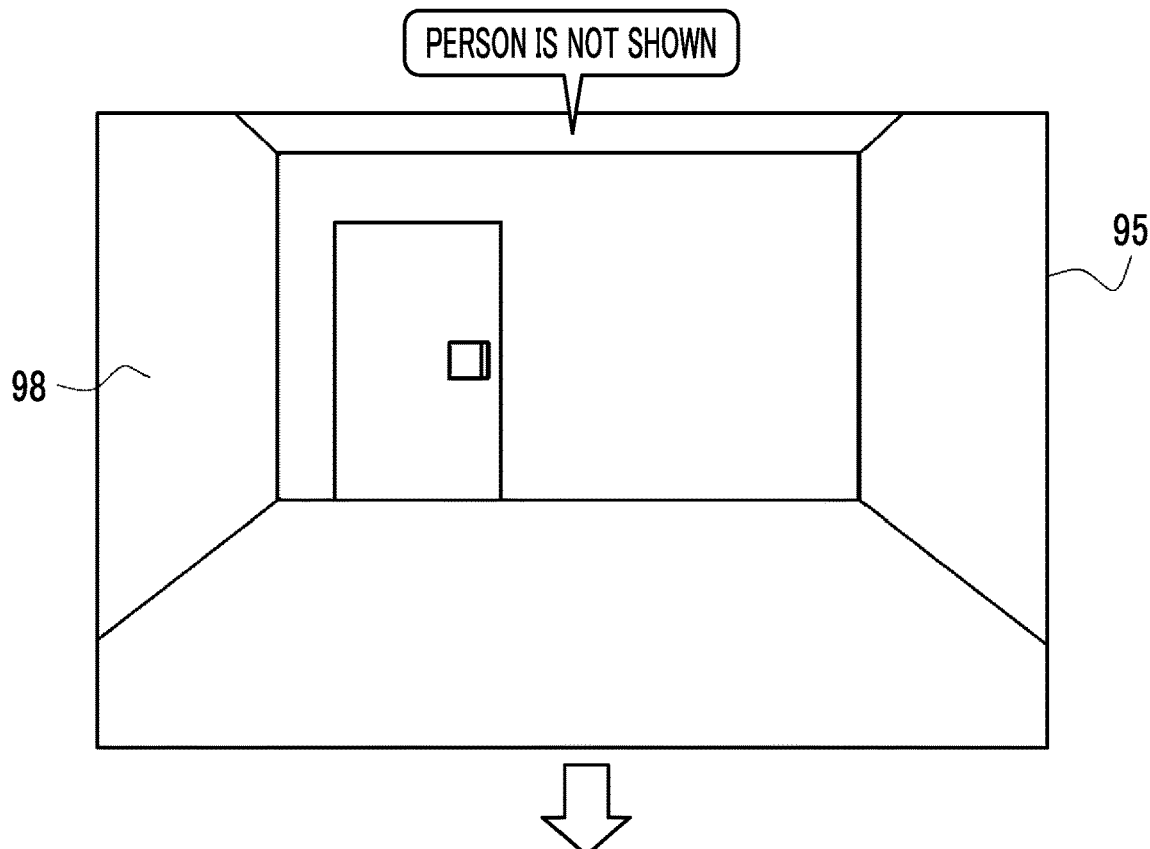
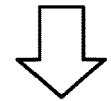
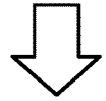
FIG. 26
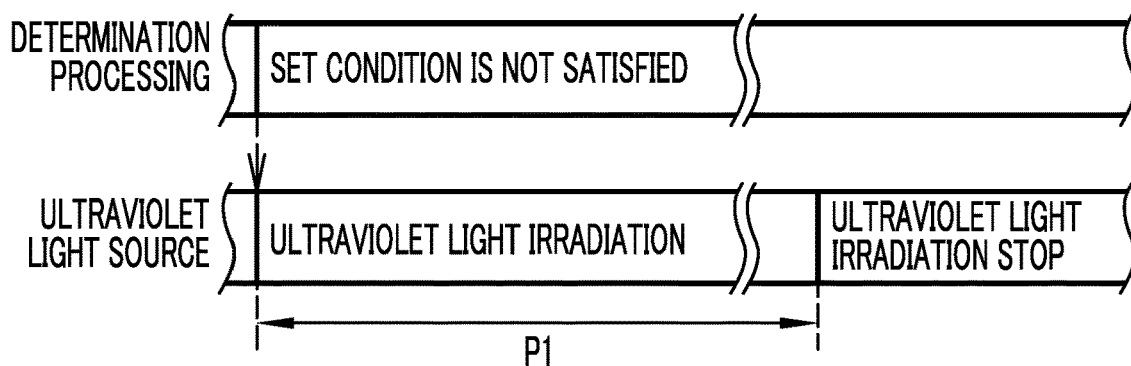

RADIODIAGNOSTIC APPARATUS AND METHOD OF OPERATING RADIODIAGNOSTIC APPARATUS

CROSS-REFERENCE TO RELATED APPLICATIONS

This application claims priority under 35 USC 119 from Japanese Patent Application No. 2020-137646 filed on Aug. 17, 2020, and Japanese Patent Application No. 2020-194559 filed on Nov. 24, 2020, the disclosures of which are incorporated herein by reference in their entireties.

BACKGROUND

1. Technical Field

A technique of the present disclosure relates to a radiodiagnostic apparatus and a method of operating a radiodiagnostic apparatus.

2. Description of the Related Art

As a radiodiagnostic apparatus, for example, a breast imaging apparatus that irradiates a breast of a subject with radiation and captures a radiographic image of the breast is known. In the breast imaging apparatus, there is a place (hereinafter, referred to as a contaminated place) where a skin of the subject is in direct contact with the breast imaging apparatus or a body fluid of the subject, such as saliva, is stuck. Examples of the contaminated place include an imaging table on which the breast is placed, a pressing plate that presses the breast while sandwiching the breast with the imaging table, and a face guard that protect a face of the subject from radiation. In the related art, for example, as described in JP2008-513090A and WO2019/182077A, an operator, such as a radiographer, disinfects such contaminated places using a disinfectant solution or the like for infection prophylaxis.

SUMMARY

In a case where the operator disinfects the contaminated places using the disinfectant solution or the like, nonuniformity of disinfection is likely to occur inevitably because disinfection depends on manual operation. Accordingly, there is a concern that infection prophylaxis is insufficient.

As an infection prophylaxis other than the disinfectant solution, a case where a contaminated place is disinfected by irradiation of ultraviolet light is considered. With the irradiation of ultraviolet light, nonuniformity of disinfection is reduced. However, irradiation of a human body with ultraviolet light should be avoided as much as possible.

An embodiment according to the technique of the present disclosure provides a radiodiagnostic apparatus and a method of operating a radiodiagnostic apparatus capable of performing disinfection by irradiation of ultraviolet light while reducing a concern that a human body is irradiated with ultraviolet light.

A radiodiagnostic apparatus according to the present disclosure comprises a radiation source that irradiates an imaging part of a subject with radiation, a radiation detector that detects the radiation transmitted through the imaging part to output a radiographic image, an ultraviolet light source that performs irradiation of ultraviolet light, and a controller that prohibits the irradiation of the ultraviolet light by the ultraviolet light source in a case where a predetermined set condition is satisfied.

It is preferable that the radiodiagnostic apparatus further comprises a camera, and the controller determines that the set condition is satisfied in a case where a person is shown in a captured image of the camera.

It is preferable that the radiodiagnostic apparatus further comprises a moving body detection sensor that detects a moving body, and the controller determines that the set condition is satisfied in a case where the moving body detection sensor detects the moving body.

It is preferable that the radiodiagnostic apparatus further comprises a reception unit that receives an imaging menu indicating an imaging content, and the controller determines that the set condition is satisfied in a case where the reception unit receives the imaging menu.

It is preferable that the radiodiagnostic apparatus further comprises a mode switching unit that switches between a first operation mode where power consumption is relatively high and a second operation mode where power consumption is relatively low, and the controller determines that the set condition is not satisfied in a case where the mode switching unit performs switching to the second operation mode and permits the irradiation of the ultraviolet light by the ultraviolet light source.

It is preferable that, in a case of making the ultraviolet light source perform the irradiation of the ultraviolet light, the controller makes the ultraviolet light source continue the irradiation of the ultraviolet light for a predetermined first set period.

It is preferable that the controller makes the ultraviolet light source interrupt the irradiation of the ultraviolet light in a case where determination is made that the set condition is satisfied before the first set period elapses. In this case, it is preferable that the radiodiagnostic apparatus further comprises a first notification controller that performs control for notifying that the irradiation of the ultraviolet light is interrupted.

It is preferable that the controller makes the ultraviolet light source restart the irradiation of the ultraviolet light in a case where determination is made that the set condition is not satisfied within a predetermined second set period after the irradiation of the ultraviolet light is interrupted.

It is preferable that the imaging part is a breast, and the ultraviolet light source is provided at a place where at least one of an imaging table that incorporates the radiation detector and on which the breast is placed or a pressing plate that presses the breast while sandwiching the breast with the imaging table is irradiatable with the ultraviolet light.

It is preferable that the radiodiagnostic apparatus further comprises an irradiation field limiter that is provided between the radiation source and the pressing plate, and defines an irradiation field of the radiation to the imaging table, and the ultraviolet light source is provided on an external surface of the irradiation field limiter.

It is preferable that the radiodiagnostic apparatus further comprises an irradiation field limiter that is provided between the radiation source and the pressing plate, and defines an irradiation field of the radiation to the imaging table, and the ultraviolet light source is provided inside the irradiation field limiter.

It is preferable that an irradiation field lamp that performs irradiation of light representing the irradiation field toward the imaging table is provided in the irradiation field limiter, and the ultraviolet light source is provided alongside the irradiation field lamp.

It is preferable that the radiation source and the radiation detector are capable of changing an angle with respect to the breast, the radiodiagnostic apparatus further comprises an angle detection sensor that detects the angle, and the controller determines that the set condition is satisfied in a case where the angle detected by the angle detection sensor is a predetermined set angle.

It is preferable that the pressing plate is formed of a material that transmits the ultraviolet light.

It is preferable that the radiodiagnostic apparatus further comprises at least one of an upright imaging table or a decubitus imaging table that accommodates the radiation detector, and the ultraviolet light source is provided at a place where at least one of the upright imaging table or the decubitus imaging table is irradiatable with the ultraviolet light.

It is preferable that, in a case where the radiodiagnostic apparatus comprises both the upright imaging table and the decubitus imaging table, an ultraviolet light source for the upright imaging table and an ultraviolet light source for the decubitus imaging table are provided separately.

It is preferable that the radiodiagnostic apparatus further comprises an arm that integrally retains the radiation source and the radiation detector at facing positions, and the ultraviolet light source is provided at a place where a bed that is disposed between the radiation source and the radiation detector and on which the subject lies is irradiatable with the ultraviolet light.

It is preferable that the radiodiagnostic apparatus further comprises a body portion on which the radiation source and a portable radiation detector are mounted and that has wheels for running, and the ultraviolet light source is provided at a place where the portable radiation detector is irradiatable with the ultraviolet light.

It is preferable that the radiodiagnostic apparatus further comprises a gantry that incorporates the radiation source and the radiation detector, and a bed on which the subject lies and that slides and moves in the gantry, and the ultraviolet light source is provided at a place where the bed is irradiatable with the ultraviolet light.

It is preferable that the ultraviolet light source is provided in an irradiation field limiter that defines an irradiation field of the radiation.

It is preferable that the radiodiagnostic apparatus further comprises a foot switch that is stepped on by an operator with a foot and operated, and the ultraviolet light source is provided at a place where the foot switch is irradiatable with the ultraviolet light.

It is preferable that the ultraviolet light source is provided in a foot-operating portion of the foot switch.

It is preferable that the radiodiagnostic apparatus further comprises a cover that covers the foot switch from above, and the ultraviolet light source is provided inside the cover.

It is preferable that the radiodiagnostic apparatus further comprises a measurement unit that measures an irradiation time of the ultraviolet light by the ultraviolet light source, and a storage controller that stores the irradiation time measured by the measurement unit in a storage unit.

It is preferable that there are a plurality of places where the irradiation of the ultraviolet light is performed, the measurement unit measures the irradiation time for each of the plurality of places, and the storage controller stores the irradiation time of each of the plurality of places measured by the measurement unit for each of the plurality of places.

It is preferable that the radiodiagnostic apparatus further comprises a second notification controller that performs control for notifying of the irradiation time.

It is preferable that the radiodiagnostic apparatus further comprises a third notification controller that, in a case where a cumulative irradiation time obtained by integrating the irradiation time exceeds a set time set in advance, performs control for notifying that the cumulative irradiation time exceeds the set time.

A method of operating an radiodiagnostic apparatus according to the present disclosure comprises irradiating an imaging part of a subject with radiation from a radiation source, detecting the radiation transmitted through the imaging part with a radiation detector to output a radiographic image, performing irradiation of ultraviolet light from an ultraviolet light source, and prohibiting the irradiation of the ultraviolet light by the ultraviolet light source in a case where a predetermined set condition is satisfied.

According to the technique of the present disclosure, it is possible to provide a radiodiagnostic apparatus and a method of operating a radiodiagnostic apparatus capable of performing disinfection by irradiation of ultraviolet light while reducing a concern that a human body is irradiated with ultraviolet light.

BRIEF DESCRIPTION OF THE DRAWINGS

Exemplary embodiments according to the technique of the present disclosure will be described in detail based on the following figures, wherein:

FIG. 1 is a diagram showing a breast imaging apparatus and the like;

FIG. 13 is a diagram showing an irradiation condition table;

FIG. 16 is a diagram showing a scene in which a turn-off command signal is received and irradiation of ultraviolet light from the ultraviolet light source is stopped;

FIG. 17 is a flowchart showing a processing procedure of the control device;

FIG. 25 is a diagram showing processing of the controller in a case where a person is not shown in the captured image of the camera;

FIG. 26 is a diagram showing an aspect in which the ultraviolet light source continues irradiation of ultraviolet light for a first set period;

DETAILED DESCRIPTION

First Embodiment

Figure 1:
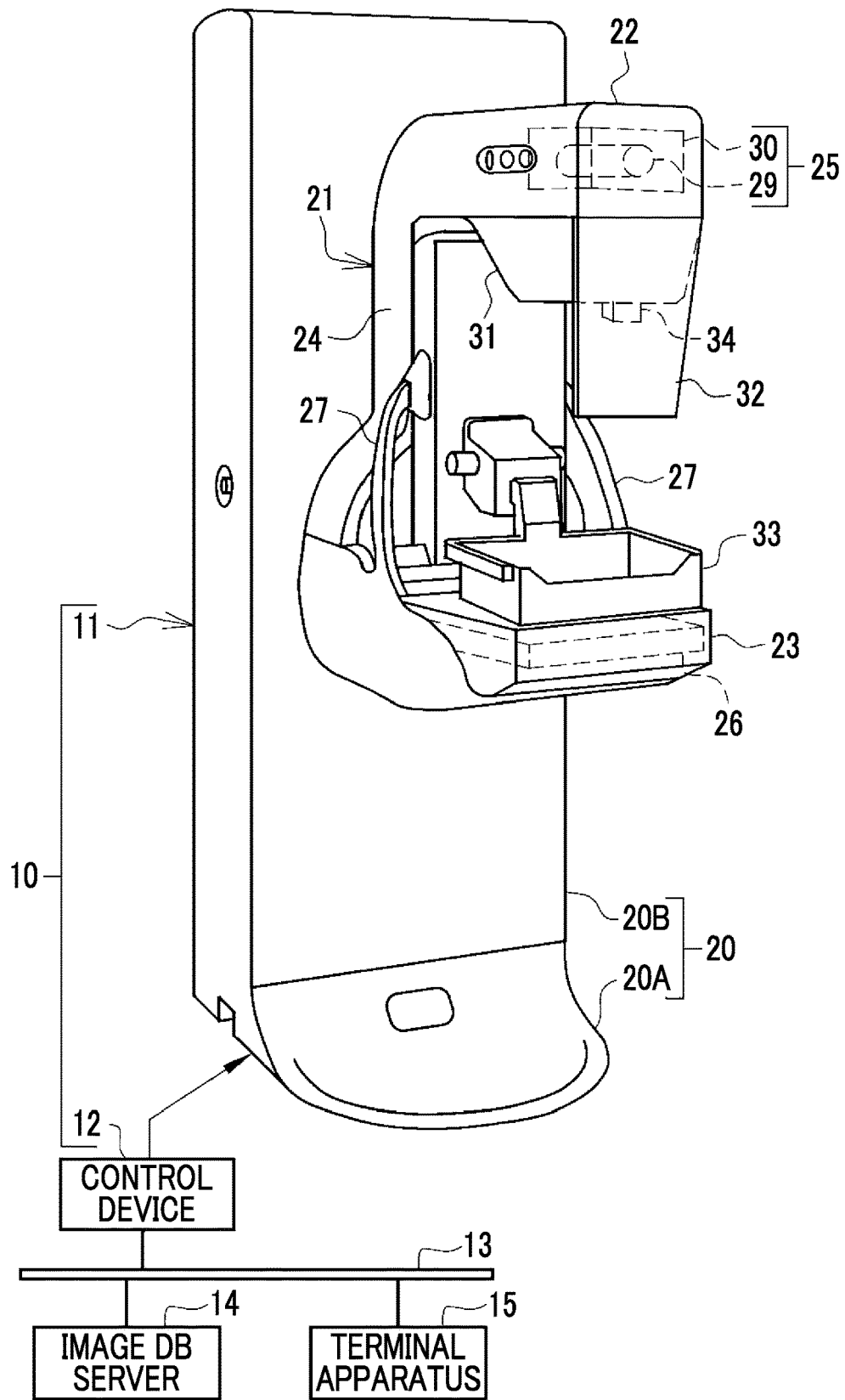
Figure 2:
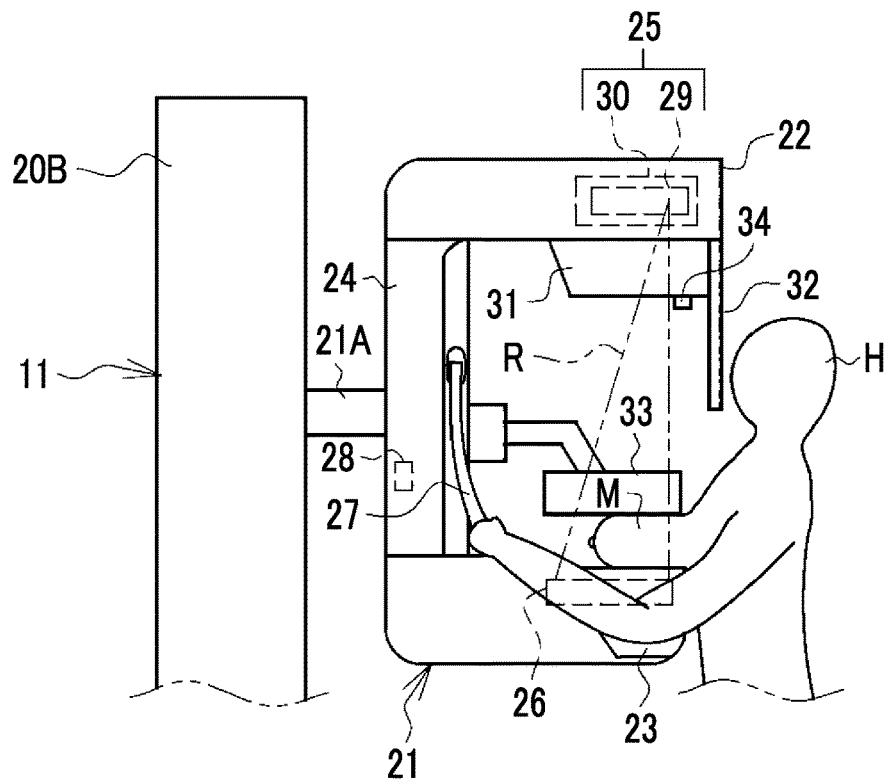
FIG. 2 is a diagram showing a scene in which a breast of a subject is irradiated with radiation.

As an example, as shown in FIGS. 1 and 2, a breast imaging apparatus 10 has a breast M of a subject H as an object. The breast imaging apparatus 10 irradiates the breast M with radiation R, such as X-rays or γ-rays, to capture a radiographic image RI (see FIG. 11) of the breast M. The breast imaging apparatus 10 is an example of a "radiodiagnostic apparatus" according to the technique of the present disclosure. The breast M is an example of an "imaging part" according to the technique of the present disclosure.

The breast imaging apparatus 10 comprises an apparatus body 11 and a control device 12. The apparatus body 11 is provided, for example, in a radiography room 98 (see FIG. 24 or the like) of a medical facility. The control device 12 is provided, for example, a control room next to the radiography room 98. The control device 12 is, for example, a desktop personal computer. The control device 12 is connected to an image database (hereinafter, abbreviated as DB) server 14 through a network 13, such as a local area network (LAN) in a communicable manner. The image DB server 14 is, for example, a picture archiving and communication system (PACS) server, receives the radiographic image RI from the breast imaging apparatus 10, and accumulates and manages the received radiographic image RI.

A terminal apparatus 15 is also connected to the network 13. The terminal apparatus 15 is, for example, a personal computer that is used by a physician who performs medical examination using the radiographic image RI. The terminal apparatus 15 receives the radiographic image RI from the image DB server 14 and displays the received radiographic image RI on a display.

The apparatus body 11 has a stand 20 and an arm 21. The stand 20 is configured with a pedestal 20A that is provided on a floor surface of the radiography room 98, and a column 20B that extends from the pedestal 20A in a height direction. The arm 21 substantially has a C shape as viewed sidewise and is connected to the column 20B through a connection portion 21A. The arm 21 is movable in the height direction with respect to the column 20B and can perform height adjustment corresponding to the height of the subject H with the connection portion 21A. The arm 21 is rotatable around a rotation axis that passes through the connection portion 21A and is perpendicular to the column 20B.

The arm 21 is configured with a radiation source accommodation portion 22, an imaging table 23, and a body portion 24. A radiation source 25 is accommodated in the radiation source accommodation portion 22. The breast M is placed on the imaging table 23. A radiation detector 26 is accommodated in the imaging table 23. The body portion 24 integrally connects the radiation source accommodation portion 22 and the imaging table 23. The body portion 24 retains the radiation source accommodation portion 22 and the imaging table 23 at facing positions. Banisters 27 that are gripped by the hands of the subject H are provided on both sides of the body portion 24.

An indirect illumination lamp 28 is attached to the body portion 24. The indirect illumination lamp 28 performs irradiation of warm-colored and subdued indirect illumination light toward the column 20B to alleviate the anxiety of the subject H. The indirect illumination lamp 28 may be attached to the external surface and/or the inside of the column 20B. In this case, the indirect illumination lamp 28 performs irradiation of indirect illumination light toward the body portion 24.

The radiation source 25 is configured with a radiation tube 29, and a housing 30 that accommodates the radiation tube 29. The housing 30 is filled with insulating oil. The radiation tube 29 performs the irradiation of the radiation R toward the breast M placed on the imaging table 23. The radiation detector 26 detects the radiation R transmitted through the breast M to output the radiographic image RI.

An irradiation field limiter 31 is provided between the radiation source accommodation portion 22 and the imaging table 23. The irradiation field limiter 31 is also referred to as a collimator and defines an irradiation field of the radiation R to the imaging table 23.

A face guard 32 is attached to the radiation source accommodation portion 22. The face guard 32 is formed of or coated with a material not transmitting the radiation R and protects the face of the subject H from the radiation R.

A pressing plate 33 is attached between the imaging table 23 and the irradiation field limiter 31. The pressing plate 33 is formed of a material transmitting the radiation R. The pressing plate 33 is disposed at a position facing the imaging table 23. The pressing plate 33 is movable in a direction toward the imaging table 23 and a direction apart from the imaging table 23 corresponding to an operation of a lift switch (not shown). The pressing plate 33 moves toward the imaging table 23 to press the breast M while sandwiching the breast M with the imaging table 23.

A tube voltage generator (not shown) that generates a tube voltage to be applied to the radiation tube 29 is provided in the column 20B. A voltage cable (not shown) that extends from the tube voltage generator is also provided in the column 20B. The voltage cable is introduced into the radiation source accommodation portion 22 from the connection portion 21A through the arm 21 and is connected to the radiation tube 29.

Figure 3:
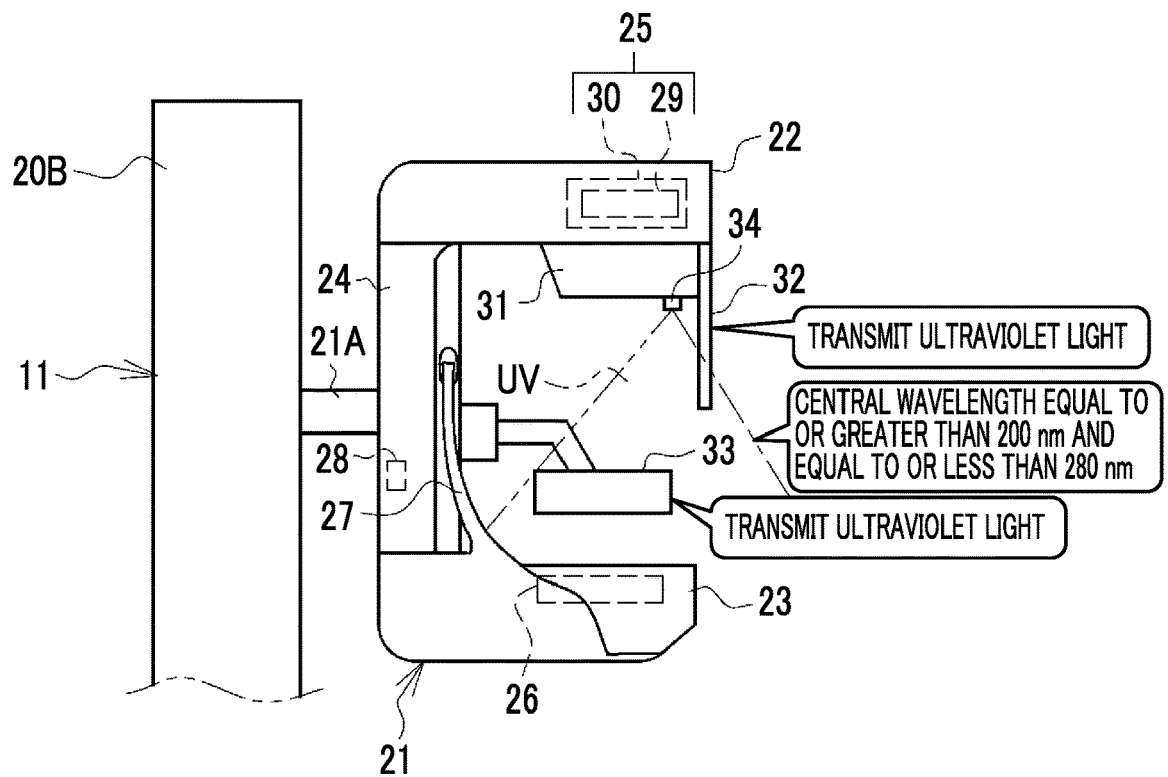
FIG. 3 is a diagram showing a scene in which irradiation of ultraviolet light is performed.

An ultraviolet light source 34 is provided on the external surface of the irradiation field limiter 31 facing the pressing plate 33. In more detail, the ultraviolet light source 34 is provided on the external surface of the irradiation field limiter 31 on a rear side of the face guard 32. As an example, as shown in FIG. 3, the ultraviolet light source 34 performs irradiation of ultraviolet light UV having a central wavelength equal to or greater than 200 nm and equal to or less than 280 nm toward the face guard 32, the pressing plate 33, and the like. As the ultraviolet light source 34, in addition to a general ultraviolet lamp using a silica tube, such as an excimer lamp, a light emitting diode (LED), a laser diode (LD), or the like can be employed.

The face guard 32 and the pressing plate 33 are formed of a material transmitting the ultraviolet light UV. Examples of the material transmitting the ultraviolet light UV include "CYTOP (Registered Trademark)" (Product Name, manufactured by AGC Inc). For this reason, the ultraviolet light UV is incident into the face guard 32 from a rear surface of the face guard 32, and a surface of the face guard 32 confronting the face of the subject H is irradiated with the ultraviolet light UV. The ultraviolet light UV is incident into the pressing plate 33 from a rear surface of the pressing plate 33, and a surface of the pressing plate 33 in contact with the breast M is irradiated with the ultraviolet light UV. The imaging table 23 on which the breast M is placed is irradiated with the ultraviolet light UV transmitted through the pressing plate 33. That is, in the example, the imaging table 23, the face guard 32, and the pressing plate 33 are primarily irradiated with the ultraviolet light UV.

Figure 4:
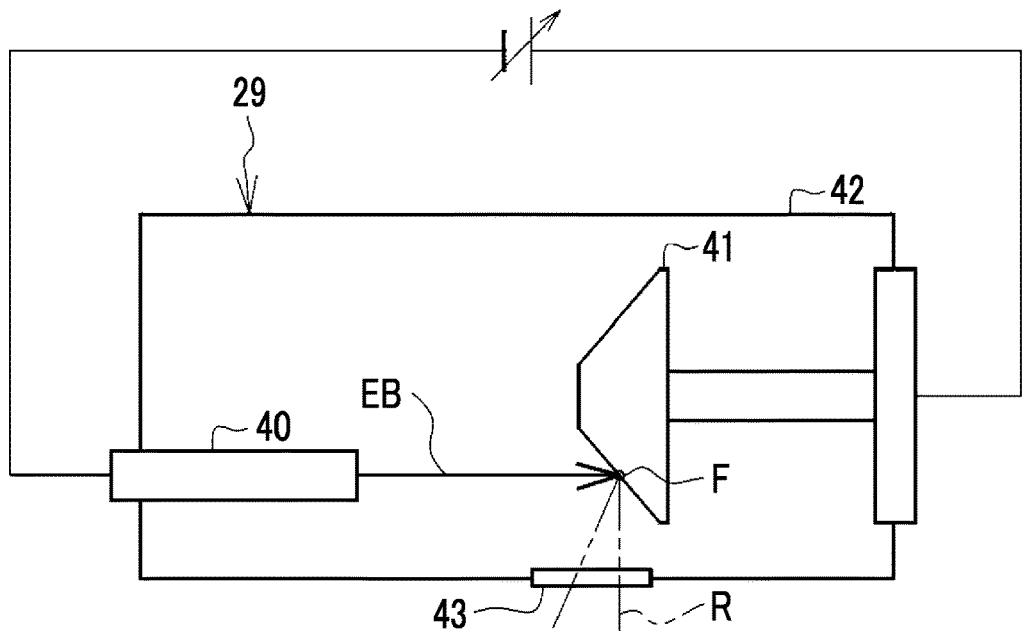
FIG. 4 is a diagram showing a radiation tube.

As an example, as shown in FIG. 4, the radiation tube 29 has a cathode 40 and an anode 41. The cathode 40 emits electrons. The anode 41 emits the radiation R upon colliding with the electrons. The cathode 40 and the anode 41 are accommodated in a substantially cylindrical vacuum glass tube 42. The cathode 40 is a cold cathode. In more detail, the cathode 40 is an electric field emission type having an electron emission source that emits electron beam EB toward the anode 41 using an electric field emission phenomenon. The anode 41 is a rotating anode that is rotated by a rotation mechanism. A fixed anode that is not rotated and is fixedly positioned may be used.

The tube voltage from the tube voltage generator is applied between the cathode 40 and the anode 41. With the application of the tube voltage, the electron beam EB is emitted from the cathode 40 toward the anode 41. Then, the radiation R is emitted from a point (hereinafter, referred to as a focus) F of the anode 41 where the electron beam EB collides. The radiation R is emitted from an irradiation window 43 provided in the glass tube 42 to the outside.

Figure 5:
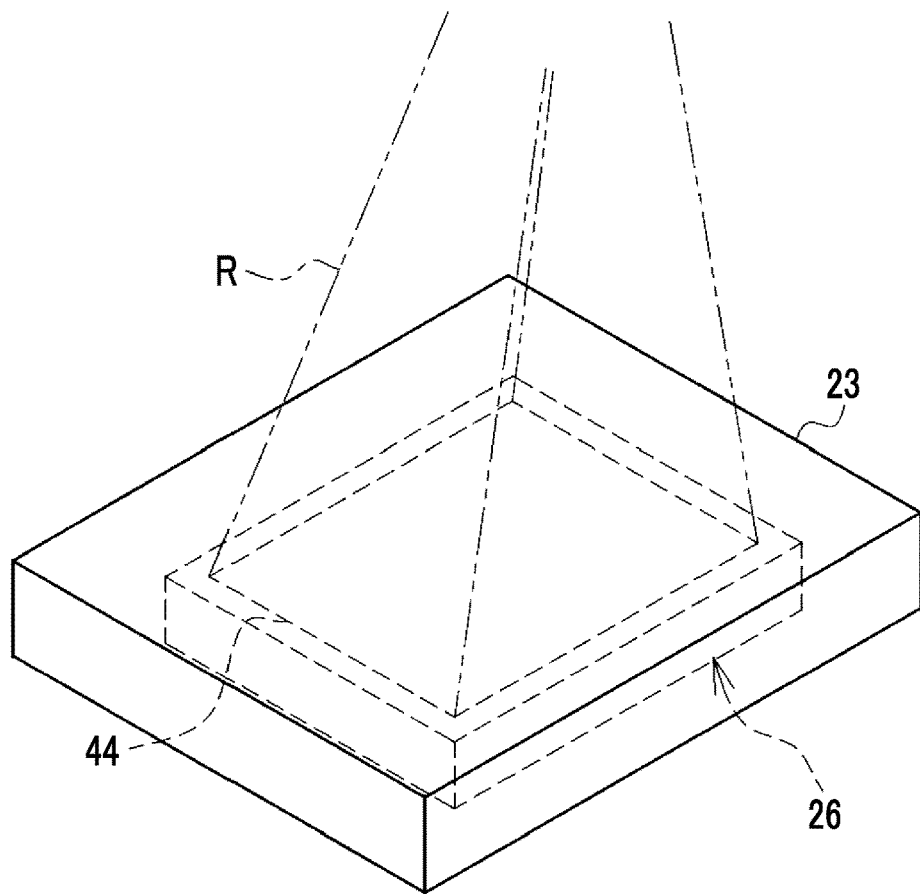
FIG. 5 is a diagram showing a portion of an imaging table.

In FIG. 5 showing a portion of the imaging table 23, the radiation detector 26 has a detection surface 44. The detection surface 44 is a surface that detects the radiation R transmitted through the breast M. In more detail, the detection surface 44 is a two-dimensional plane in which pixels for converting the radiation R into an electrical signal are arranged in a two-dimensional manner. Such a radiation detector 26 is referred to as a flat panel detector (FPD). The radiation detector 26 may be an indirect conversion type that has a scintillator configured to convert the radiation R into visible light and converts visible light emitted from the scintillator into an electrical signal or may be a direct conversion type that directly converts the radiation R into an electrical signal.

Figure 6:
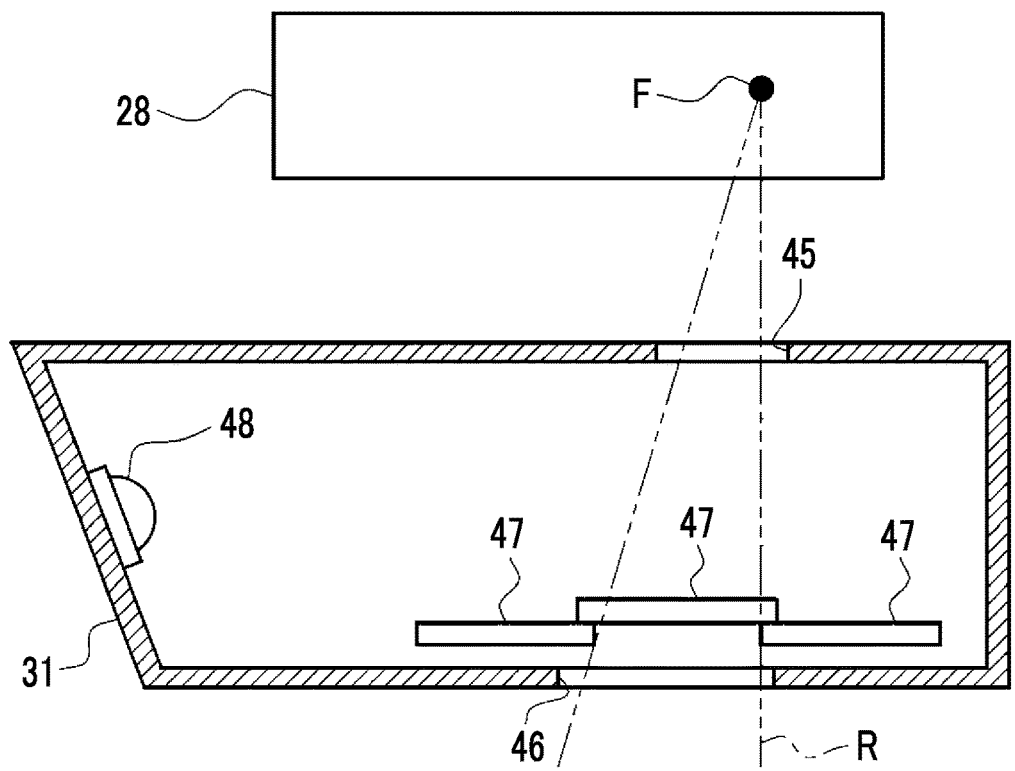
FIG. 6 is a diagram showing a scene in which an irradiation field of radiation is defined with an irradiation field limiter.
Figure 7:
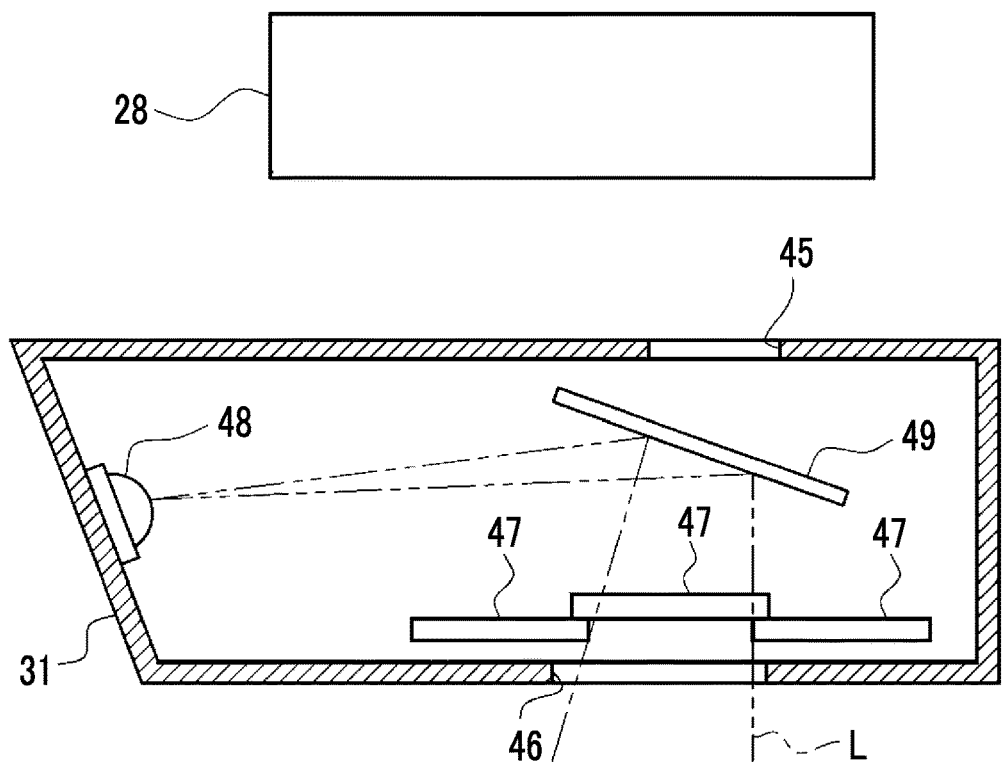
FIG. 7 is a diagram showing a scene in which irradiation of visible light representing an irradiation field is performed from an irradiation field lamp.

As an example, as shown in FIGS. 6 and 7, in the irradiation field limiter 31, an incidence opening 45 on which the radiation R from the radiation tube 29 is incident, and an emission opening 46 from which the radiation R is emitted. Four shield plates 47 (in FIGS. 6 and 7, only three shield plates are shown) are provided in the vicinity of the emission opening 46. The shield plates 47 are formed of a material shielding the radiation R, for example, lead. The shield plates 47 are disposed on sides of a quadrangle, in order words, are arranged in parallel crosses (checkered pattern) and form a quadrangular irradiation opening that transmits the radiation R. The irradiation field limiter 31 changes the size of the irradiation opening by changing the position of each shield plate 47, and as a result, changes the irradiation field of the radiation R to the imaging table 23.

An irradiation field lamp 48 and a mirror 49 are provided in the irradiation field limiter 31. The irradiation field lamp 48 emits, for example, orange-colored visible light L toward the mirror 49. As shown in FIG. 7, the mirror 49 reflects the visible light L. The mirror 49 is made, for example, by depositing an aluminum film on an acrylic plate. The visible light L reflected by the mirror 49 is emitted as light representing the irradiation field toward the imaging table 23 through the emission opening 46. The mirror 49 is retracted to a position out of the incidence opening 45 and the emission opening 46 at the time of the irradiation of the radiation R shown in FIG. 6. A filter that changes the quality of the radiation R may be provided in the irradiation field limiter 31.

Figure 8:
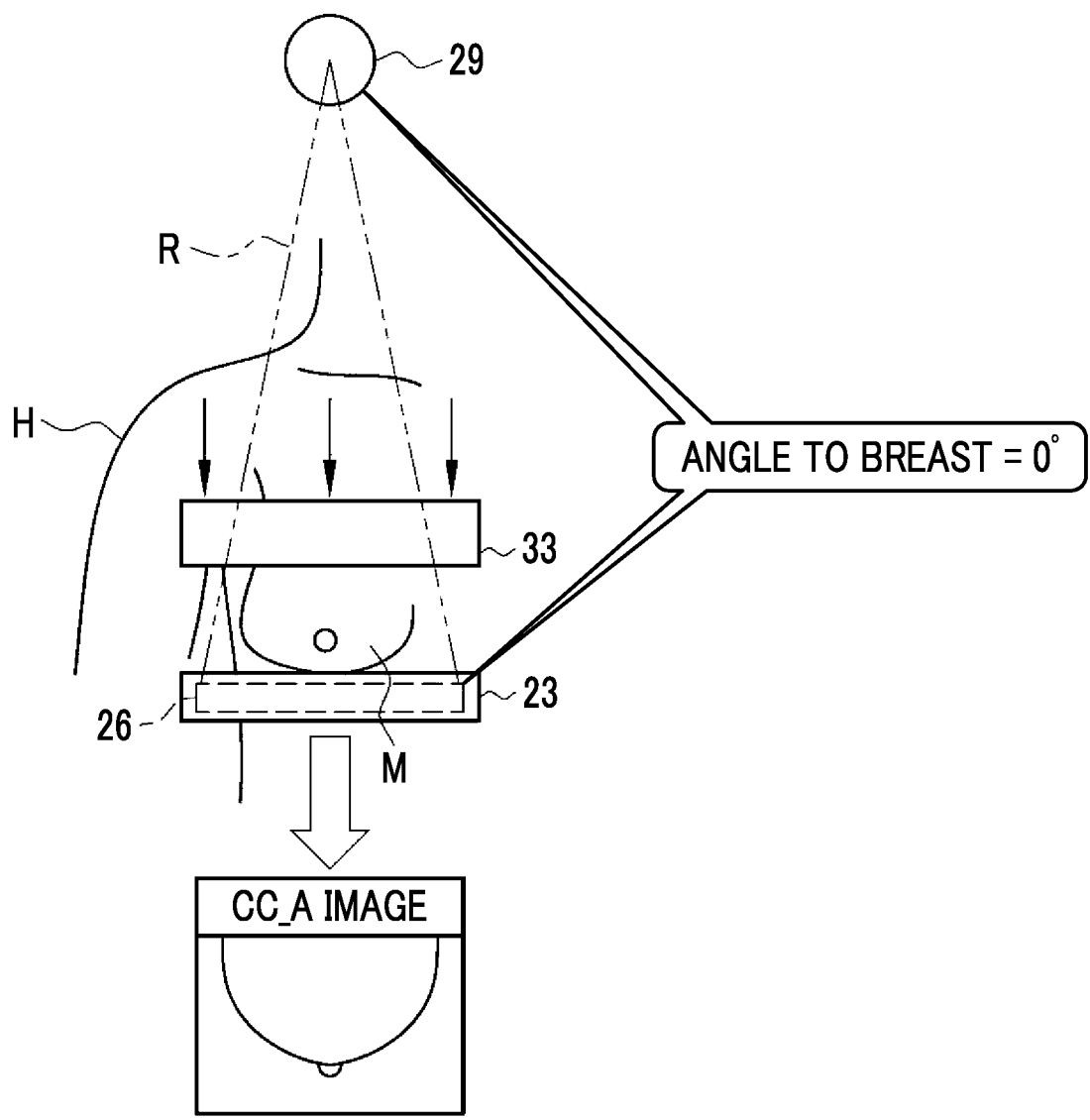
FIG. 8 is a diagram showing a scene of CC_A imaging.
Figure 9:
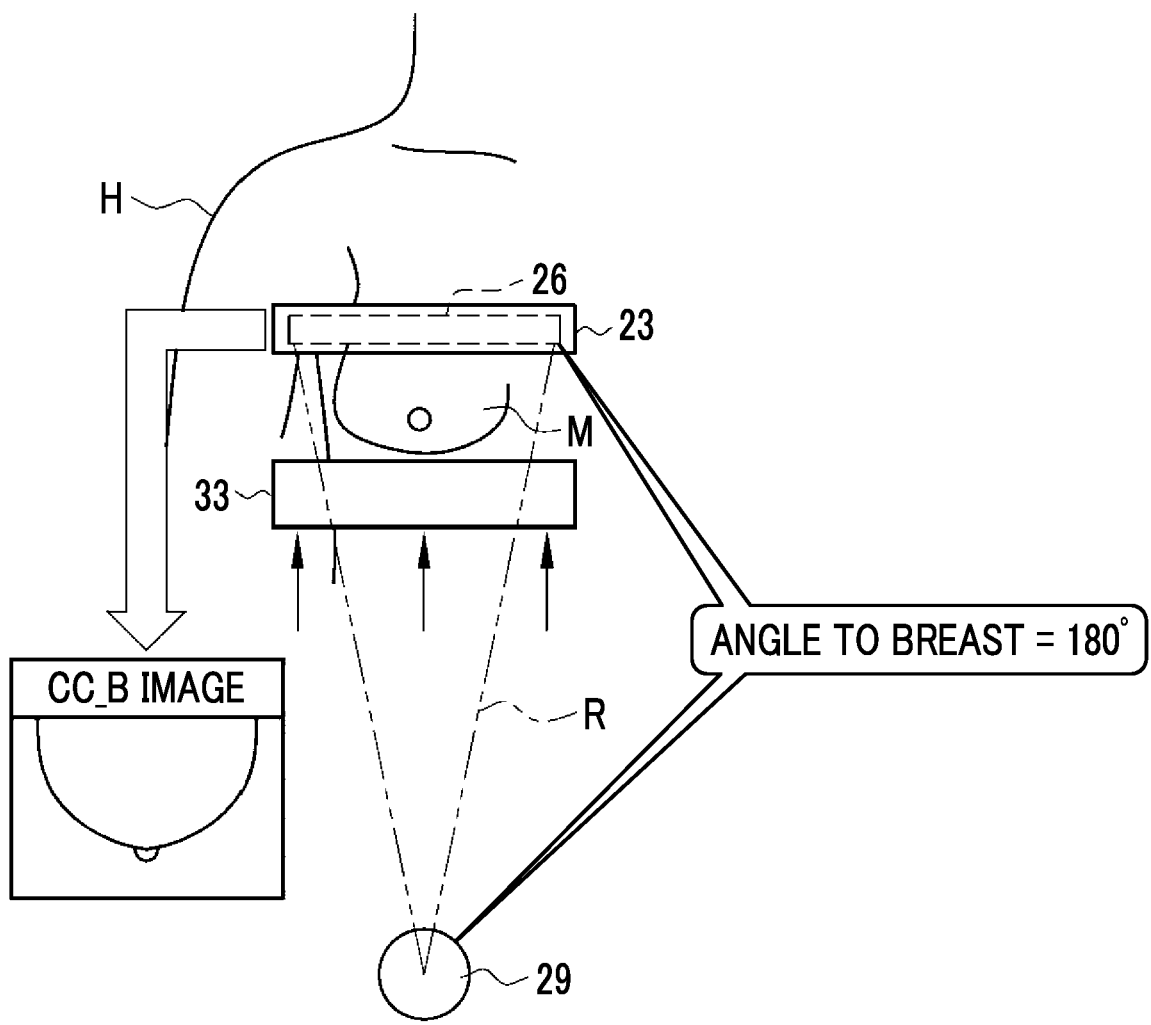
FIG. 9 is a diagram showing a scene of CC_B imaging.
Figure 10:
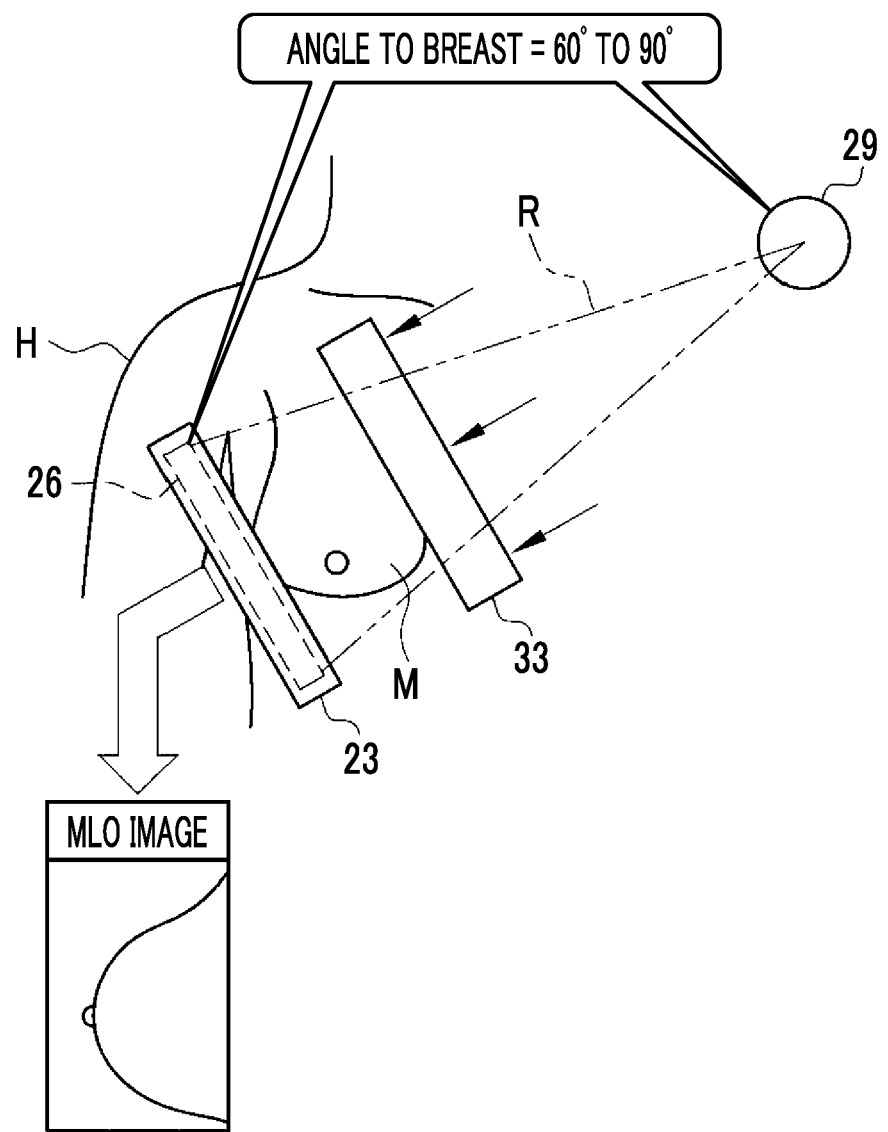
FIG. 10 is a diagram showing a scene of MLO imaging.

FIGS. 8 to 10 show an example of an imaging method of the breast M in the breast imaging apparatus 10. FIG. 8 is first craniocaudal (Craniocaudal view (CC)_A) imaging, FIG. 9 is second craniocaudal (CC_B) imaging, and FIG. 10 is mediolateral oblique (MLO view) imaging.

In FIG. 8, CC_A imaging is an imaging method in which imaging is performed while vertically sandwiching and pressing the breast M between the imaging table 23 and the pressing plate 33 in a state in which the radiation tube 29 (radiation source 25) is disposed directly above the breast M and the imaging table 23 (radiation detector 26) is disposed directly below the breast while sandwiching the breast M therebetween. In this case, the radiation detector 26 outputs a CC-A image as the radiographic image RI. It is assumed that an angle of the radiation source 25 and the radiation detector 26 with respect to the breast M in CC_A imaging is 0°.

In FIG. 9, CC_B imaging is an imaging method in which imaging is performed while vertically sandwiching and pressing the breast M between the imaging table 23 and the pressing plate 33 in a state in which the radiation tube 29 (radiation source 25) is disposed directly below the breast M and the imaging table 23 (radiation detector 26) is disposed directly above the breast M while sandwiching the breast M therebetween. In this case, the radiation detector 26 outputs a CC_B image as the radiographic image RI. The angle of the radiation source 25 and the radiation detector 26 with respect to the breast M in CC_B imaging is 180°.

In FIG. 10, MLO imaging is an imaging method in which imaging is performed while obliquely sandwiching and pressing the breast M between the imaging table 23 and the pressing plate 33 at an angle in a range of 60° to 90°. In this case, the radiation detector 26 outputs an MLO image as the radiographic image RI. The angle of the radiation source 25 and the radiation detector 26 with respect to the breast M in MLO imaging is 60° to 90°. In FIGS. 8 and 10, although the right breast M is shown, imaging of the left breast M can be of course performed.

Figure 11:
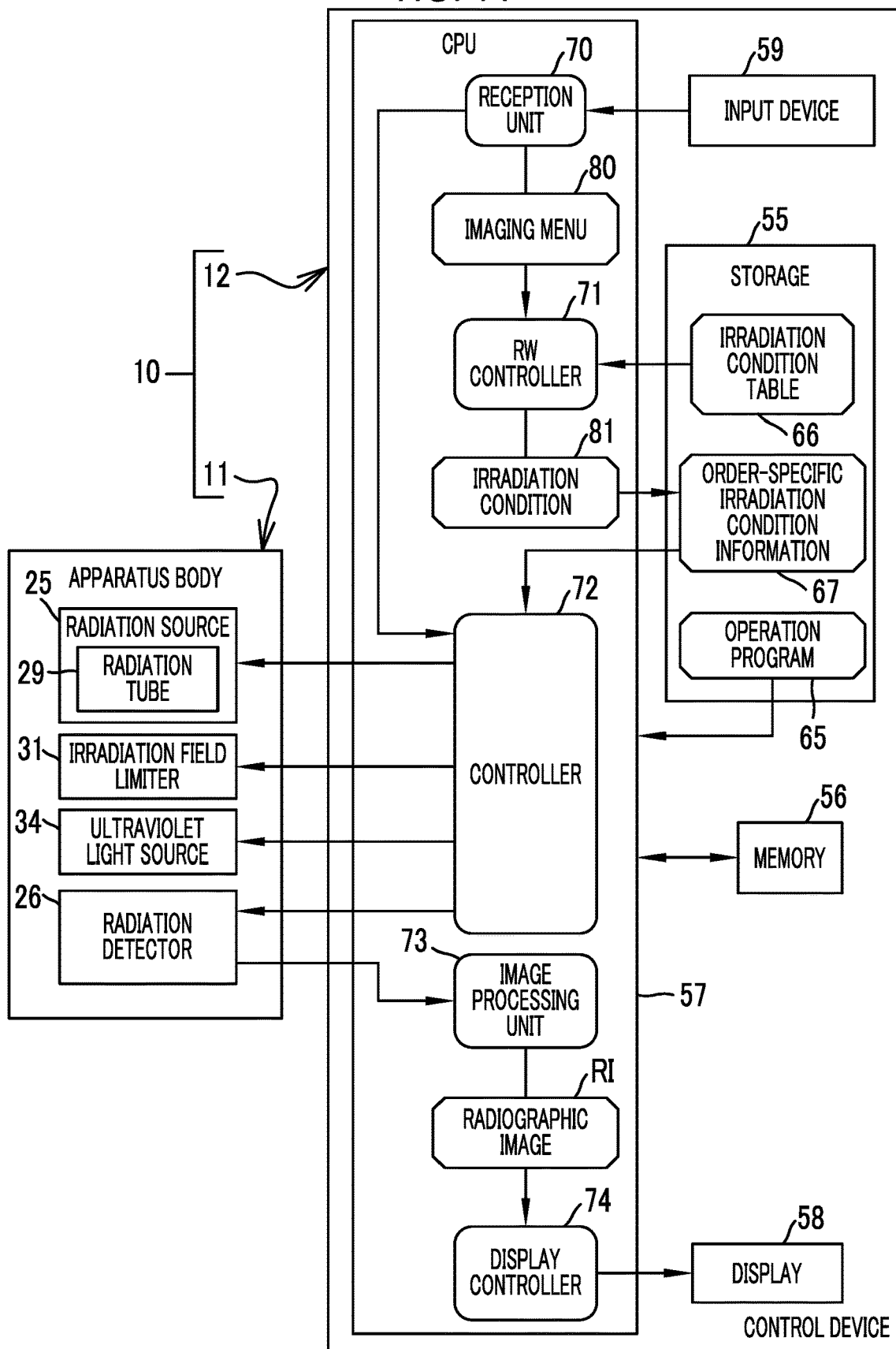
FIG. 11 is a block diagram primarily showing a processing unit of a CPU of a control device.

As an example, as shown in FIG. 11, a computer configuring the control device 12 comprises a storage 55, a memory 56, a central processing unit (CPU) 57, a display 58, an input device 59, and the like.

The storage 55 is a hard disk drive that is incorporated in the computer configuring the control device 12 or is connected to the computer through a cable or a network. Of course, the storage 55 is a disk array in which a plurality of hard disk drives are mounted. In the storage 55, a control program, such as an operating system, various application programs, various kinds of data associated with such programs, and the like are stored. A solid state drive may be used instead of the hard disk drive.

The memory 56 is a work memory on which the CPU 57 executes processing. The CPU 57 integrally controls the units of the computer by loading the programs stored in the storage 55 into the memory 56 and executing processing compliant with the programs.

The display 58 displays various screens. Various screens are provided with an operation function by a graphical user interface (GUI). The computer configuring the control device 12 receives an input of an operation command from the input device 59 through various screens. The input device 59 is a keyboard, a mouse, a touch panel, or the like.

An operation program 65 is stored in the storage 55. The operation program 65 is an application program for causing the computer to function as the control device 12. In the storage 55, in addition to the operation program 65, an irradiation condition table 66, order-specific irradiation condition information 67, and the like are stored.

In a case where the operation program 65 is activated, the CPU 57 of the control device 12 functions as a reception unit 70, a read-write (hereinafter, abbreviated as RW) controller 71, a controller 72, an image processing unit 73, and a display controller 74 in cooperation with the memory 56.

The reception unit 70 receives various operation commands input by an operator OP (see FIG. 24 or the like) through the input device 59. For example, the reception unit 70 receives an imaging menu 80. The reception unit 70 outputs the imaging menu 80 to the RW controller 71.

The RW controller 71 receives the imaging menu 80 from the reception unit 70. The RW controller 71 reads an irradiation condition 81 corresponding to the received imaging menu 80 from the irradiation condition table 66. The RW controller 71 writes the irradiation condition 81 read from the irradiation condition table 66 in the order-specific irradiation condition information 67.

The controller 72 controls the operation of the radiation source 25 (radiation tube 29), the radiation detector 26, the irradiation field limiter 31, and the ultraviolet light source 34. The controller 72 reads the irradiation condition 81 from the order-specific irradiation condition information 67. The controller 72 operates the irradiation field limiter 31 in compliance with the irradiation condition 81 and adjusts the irradiation field. The controller 72 operates the radiation tube 29 in compliance with the irradiation condition 81 and performs the irradiation of the radiation R from the radiation tube 29. The controller 72 outputs the radiographic image RI detected by the radiation detector 26 with the irradiation of the radiation R from the radiation detector 26 to the image processing unit 73.

The image processing unit 73 receives the radiographic image RI from the radiation detector 26. The image processing unit 73 executes various kinds of image processing on the radiographic image RI. The image processing unit 73 outputs the radiographic image RI after the image processing to the display controller 74. The display controller 74 receives the radiographic image RI from the image processing unit 73. The display controller 74 displays the radiographic image RI on the display 58.

Figure 12:
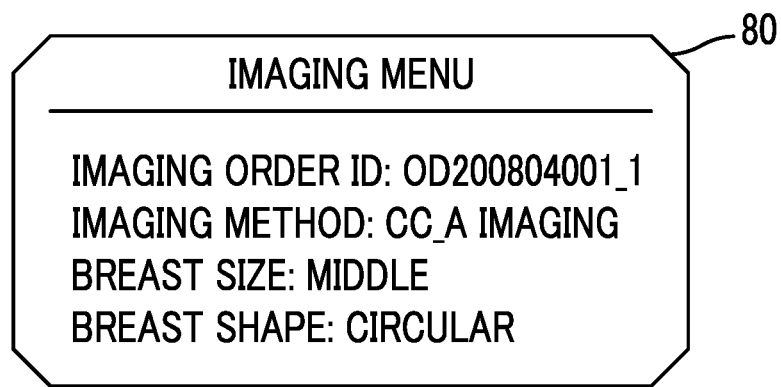
FIG. 12 is a diagram showing an imaging menu.

As an example, as shown in FIG. 12, the imaging menu 80 includes imaging order identification data (ID), an imaging method, the size of the breast M, and the shape of the breast M. The imaging order ID is identification information of an imaging order issued by the physician who performs medical examination using the radiographic image RI. The imaging method is any of CC_A imaging, CC_B imaging, and MLO imaging shown in FIGS. 8 to 10. The size of the breast M is any of large, middle, and small. The shape of the breast M is any of circular, horizontally long, and vertically long. In the imaging order, the imaging method, the size of the breast M, and the shape of the breast M are registered. The size and the shape of the breast M may not be included in the imaging order and the imaging menu 80.

The imaging order is transmitted from a radiology information system (RIS) (not shown) to the control device 12. The control device 12 displays a list of imaging orders on the display 58 under the control of the display controller 74. The operator OP views the list of imaging orders and confirms the contents. Subsequently, the control device 12 displays the imaging menu corresponding to the imaging order on the display 58 in a settable form. The operator OP selects and inputs the imaging menu corresponding to the imaging order by operating the input device 59.

As an example, as shown in FIG. 13, in the irradiation condition table 66, the irradiation condition 81 is registered for each combination of the imaging method, the size of the breast M, and the shape of the breast M. The irradiation condition 81 includes a tube voltage, a tube current, an irradiation time, and an irradiation field size. In a case where the size and the shape of the breast M are not included in the imaging menu 80, the irradiation condition table 66 is a table in which the irradiation condition 81 is registered for each imaging method. Instead of the tube current and the irradiation time, a tube current-irradiation time product, called an mAs value, may be included in the irradiation condition 81.

Figures 14, 15:
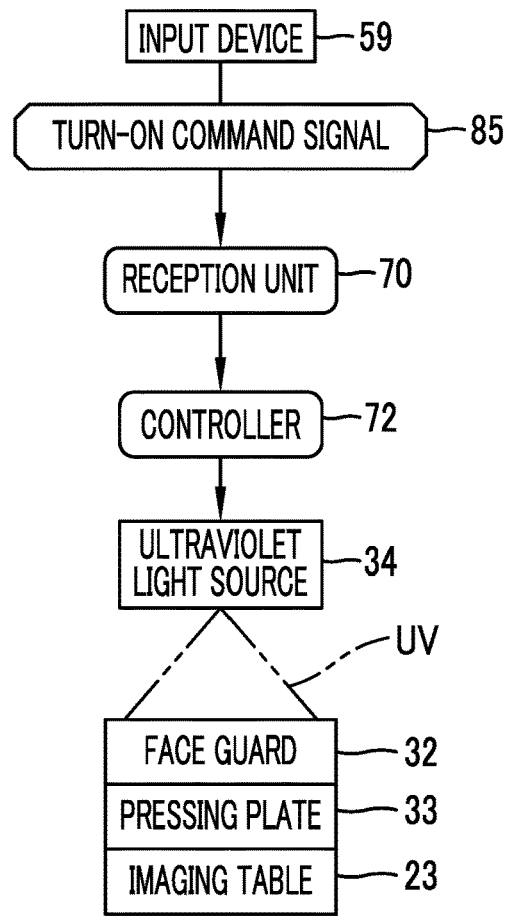
FIG. 14 is a diagram showing order-specific irradiation condition information.
FIG. 15 is a diagram showing a scene in which a turn-on command signal is received and irradiation of ultraviolet light is performed from an ultraviolet light source.

As an example, as shown in FIG. 14, in the order-specific irradiation condition information 67, the irradiation condition 81 is registered for each imaging order ID. In the order-specific irradiation condition information 67, an item of status is provided. The status includes "completed" indicating that imaging of the radiographic image RI of the imaging order is completed, "during imaging" indicating that the radiographic image RI of the imaging order is being captured, and "before imaging" indicating before imaging of the radiographic image RI of the imaging order.

As an example, as shown in FIG. 15, the reception unit 70 receives a turn-on command signal 85 input from the operator OP through the input device 59. The reception unit 70 outputs the reception of the turn-on command signal 85 to the controller 72. In this case, the controller 72 controls the operation of the ultraviolet light source 34 such that the irradiation of the ultraviolet light UV is performed.

As an example, as shown in FIG. 16, the reception unit 70 receives a turn-off command signal 86 input from the operator OP through the input device 59. The reception unit 70 outputs the reception of the turn-off command signal 86 to the controller 72. In this case, the controller 72 controls the operation of the ultraviolet light source 34 such that the irradiation of the ultraviolet light UV is stopped. That is, in the first embodiment, the irradiation and the irradiation stop of the ultraviolet light UV are switched in response to a command of the operator OP.

Next, operations of the above-described configuration will be described referring to flowcharts shown in FIGS. 17 to 19. In a case where the operation program 65 is activated, as shown in FIG. 11, the CPU 57 of the control device 12 functions as the reception unit 70, the RW controller 71, the controller 72, the image processing unit 73, and the display controller 74.

First, as an example, as shown in FIG. 17, the imaging menu 80 is received by the reception unit 70 (Step ST100). The imaging menu 80 is output from the reception unit 70 to the RW controller 71. The irradiation condition 81 corresponding to the imaging menu 80 is read from the irradiation condition table 66 by the RW controller 71 (Step ST110). Then, the irradiation condition 81 is written in the order-specific irradiation condition information 67 by the RW controller 71 (Step ST120).

The operator OP allows the subject H to enter the radiography room 98. Then, the breast M of the subject H is placed on the imaging table 23 and is pressed by the pressing plate 33.

Figure 18:
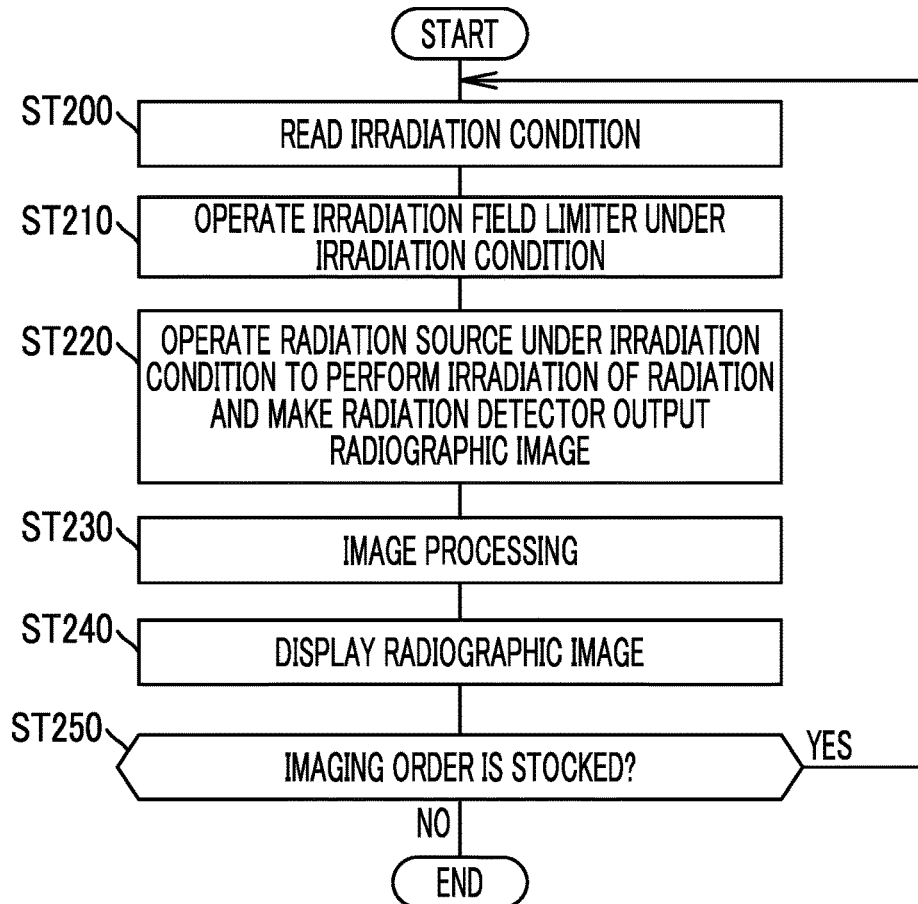
FIG. 18 is a flowchart showing a processing procedure of the control device.
Figure 19:
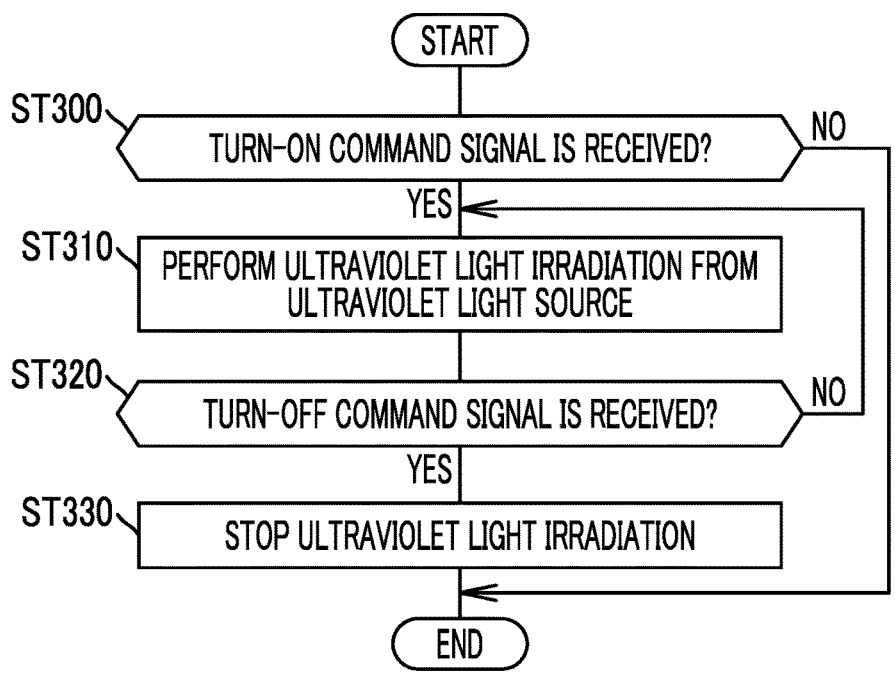
FIG. 19 is a flowchart showing a processing procedure of the control device.

As an example, as shown in FIG. 18, the irradiation condition 81 of the imaging order corresponding to the subject H is read from the order-specific irradiation condition information 67 to the controller 72 (Step ST200). Then, the irradiation field limiter 31 is operated in compliance with the irradiation condition 81 under the control of the controller 72 (Step ST210). In this case, the irradiation field lamp 48 is turned on as needed, and the irradiation field is viewed by the visible light L emitted from the irradiation field lamp 48 and reflected by the mirror 49.

The radiation tube 29 is operated in compliance with the irradiation condition 81 under the control of the controller 72, and the irradiation of the radiation R is performed (Step ST220). The radiation R emitted from the radiation tube 29 is incident on the irradiation field limiter 31. The radiation R incident on the irradiation field limiter 31 passes through the irradiation opening formed by the shield plates 47. With this, the irradiation field of the radiation R is defined.

The radiation R the irradiation field of which is defined by the irradiation field limiter 31 and with which the breast M is irradiated is detected by the radiation detector 26. With this, the radiographic image RI is output from the radiation detector 26 (Step ST220). The radiographic image RI is subjected to various kinds of image processing in the image processing unit 73 (Step ST230). The radiographic image RI after the image processing is displayed on the display 58 under the control of the display controller 74 (Step ST240). The processing of Steps ST200 to ST240 is continuously repeated while the imaging order of the status "before imaging" is in the order-specific irradiation condition information 67 (in Step ST250, YES).

The operator OP operates the input device 59 to give a command to turn on the ultraviolet light UV for the purpose of disinfecting places contaminated by the subject H, such as the imaging table 23, the face guard 32, and the pressing plate 33. With this, as an example, as shown in FIG. 19, the turn-on command signal 85 is received in the reception unit 70 (in Step ST300, YES). Then, the operation of the ultraviolet light source 34 is controlled by the controller 72, and the irradiation of the ultraviolet light UV from the ultraviolet light source 34 is performed (Step ST310).

In a case where determination is made that disinfection by the ultraviolet light UV is sufficiently performed, the operator OP operates the input device 59 to give a command to turn off the ultraviolet light UV. With this, the turn-off command signal 86 is received in the reception unit 70 (in Step ST320, YES). Then, the operation of the ultraviolet light source 34 is controlled by the controller 72, and the irradiation of the ultraviolet light UV is stopped (Step ST330).

As described above, the breast imaging apparatus 10 comprises the ultraviolet light source 34 that performs the irradiation of the ultraviolet light UV. Accordingly, it is possible to reduce nonuniformity of disinfection compared to a disinfection method depending on the hand of the operator OP using a disinfectant solution or the like.

As shown in FIG. 3, the ultraviolet light source 34 emits the ultraviolet light UV having the central wavelength equal to or greater than 200 nm and equal to or less than 280 nm. The ultraviolet light UV having the central wavelength equal to or greater than 200 nm and equal to or less than 280 nm is generally referred to as deep ultraviolet light (UV-C), has comparatively high energy, and is excellent in disinfection ability. For this reason, it is possible to exhibit a lot of disinfection effects in a short irradiation time.

As shown in FIGS. 3 and 15, the ultraviolet light source 34 is provided at a position where the imaging table 23 in which the radiation detector 26 is incorporated and on which the breast M is placed and the pressing plate 33 that sandwiches and presses the breast M with the imaging table 23 are irradiatable with the ultraviolet light UV. The imaging table 23 and the pressing plate 33 are places that are contaminated by the subject H. Accordingly, it is possible to intensively disinfect the places that are contaminated by the subject H. The place where the irradiation of the ultraviolet light UV is performed is not limited to a place where both the imaging table 23 and the pressing plate 33 are irradiated with the ultraviolet light UV, and may be a place where at least one of the imaging table 23 or the pressing plate 33 is irradiated with the ultraviolet light UV.

As shown in FIG. 1 and the like, the ultraviolet light source 34 is provided on the external surface of the irradiation field limiter 31. For this reason, it is possible to efficiently irradiate the pressing plate 33 with the ultraviolet light UV. As shown in FIG. 3, the pressing plate 33 is formed of the material transmitting the ultraviolet light UV. For this reason, it is possible to efficiently irradiate the imaging table 23 with the ultraviolet light UV through the pressing plate 33.

Although the irradiation of the ultraviolet light UV is stopped in a case where there is the turn-off command of the operator OP, the technique of the present disclosure is not limited thereto. After a predetermined period has elapsed after the reception unit 70 has received the turn-on command signal 85, the irradiation of the ultraviolet light UV may be automatically stopped.

Figure 20:
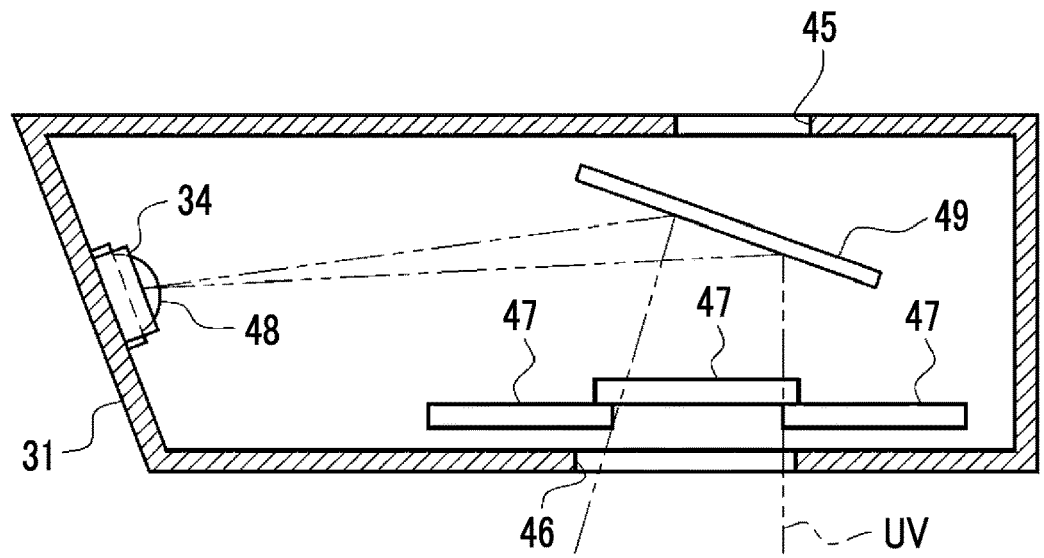
FIG. 20 is a diagram showing an aspect in which the ultraviolet light source is provided inside the irradiation field limiter.

The place where the ultraviolet light source 34 is provided is not limited to the rear side of the face guard 32 on the external surface of the irradiation field limiter 31 facing the pressing plate 33 exemplified above. As an example, as shown in FIG. 20, the ultraviolet light source 34 may be provided inside the irradiation field limiter 31. In more detail, the ultraviolet light source 34 is provided alongside the irradiation field lamp 48. Similarly to the visible light L emitted from the irradiation field lamp 48, the ultraviolet light UV emitted from the ultraviolet light source 34 is reflected by the mirror 49 and is emitted toward the imaging table 23 through the emission opening 46. In this case, the shield plates 47 are moved to positions for maximizing the size of the irradiation opening under the control of the controller 72 such that an irradiation range of the ultraviolet light UV is the maximum.

In this way, in a case where the ultraviolet light source 34 is provided inside the irradiation field limiter 31, the subject H and the operator OP do not touch the ultraviolet light source 34, and thus, there is no concern that the ultraviolet light source 34 is damaged. In a case where the ultraviolet light source 34 is provided alongside the irradiation field lamp 48, it is possible to perform the irradiation of the ultraviolet light UV using the same mechanism as for the visible light L from the irradiation field lamp 48. Note that there is a need to move the shield plates 47 to the positions for maximizing the size of the irradiation opening, and thus, it is preferable that the ultraviolet light source 34 is provided on the external surface of the irradiation field limiter 31 in that there is no need to perform such control.

Figure 21:
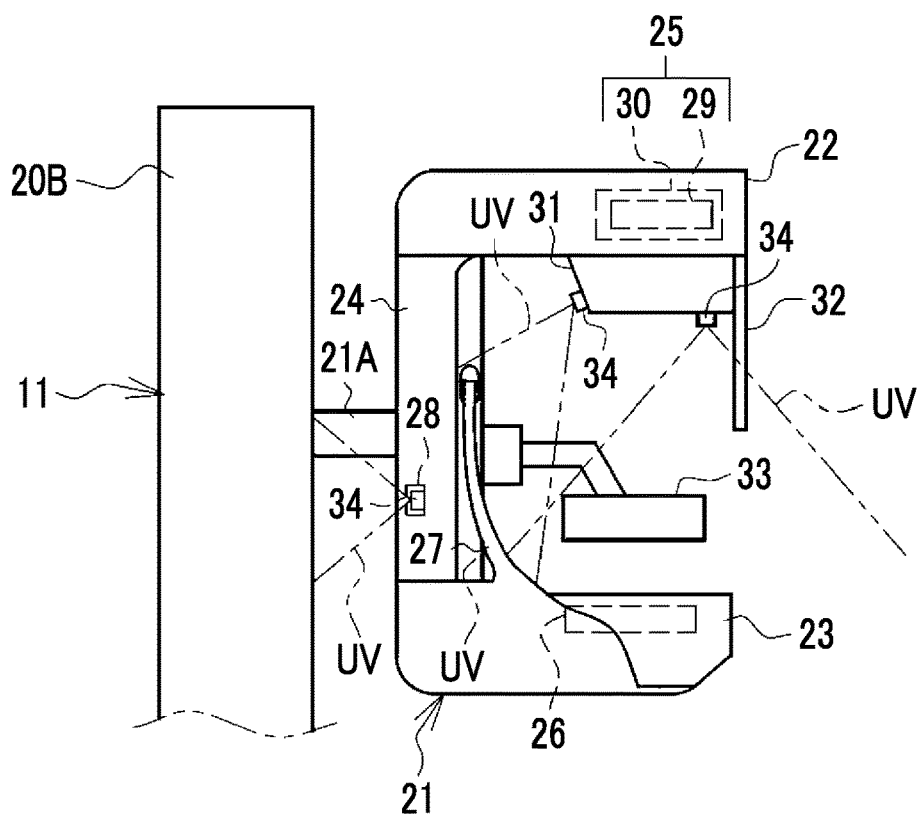
FIG. 21 is a diagram showing an aspect in which a plurality of ultraviolet light sources are provided at a plurality of places.

The place where the ultraviolet light source 34 is provided is not limited to the external surface of or inside the irradiation field limiter 31, and the number of ultraviolet light sources 34 is not limited to one. As an example, as shown in FIG. 21, the ultraviolet light sources 34 may be provided at all possible places, such as the external surface of the irradiation field limiter 31 facing the body portion 24 and a place next to the indirect illumination lamp 28. The ultraviolet light source 34 may be provided at any place as long as the places contaminated by the subject H are irradiatable with the ultraviolet light UV. It is possible to disinfect places that have been covered by one ultraviolet light source 34 provided in the irradiation field limiter 31, such as the stand 20, the body portion 24, and the banisters 27. The ultraviolet light source 34 may be provided with a swinging function such that a wide range of places is covered by one ultraviolet light source.

The ultraviolet light source 34 that is attachable and detachable with a magnet or the like and performs wireless communication with the controller 72 may be used. With such an ultraviolet light source 34, it is possible to freely attach the ultraviolet light source 34 to a place to be disinfected. Alternatively, the ultraviolet light source 34 may be attached to a place separated from the apparatus body 11, such as a wall surface or a ceiling of the radiography room 98 by a simple attachment tool, such as a screw. In this case, it is preferable that communication with the control device 12 is performed in a wireless manner.

In a case where the pressing plate 33 is replaceable depending on the size of the breast M, the irradiation of the ultraviolet light UV may be performed in a case where replacement of the pressing plate 33 is detected. Alternatively, the irradiation of the ultraviolet light UV may be performed in a case where attachment of an optional article, such as a biopsy positioner for use in performing biopsy on the breast M is detected.

Second Embodiment

In a second embodiment shown in FIGS. 22 to 46, the irradiation of the ultraviolet light UV by the ultraviolet light source 34 is prohibited in a case where a predetermined set condition is satisfied.

Second_1 Embodiment

Figure 22:
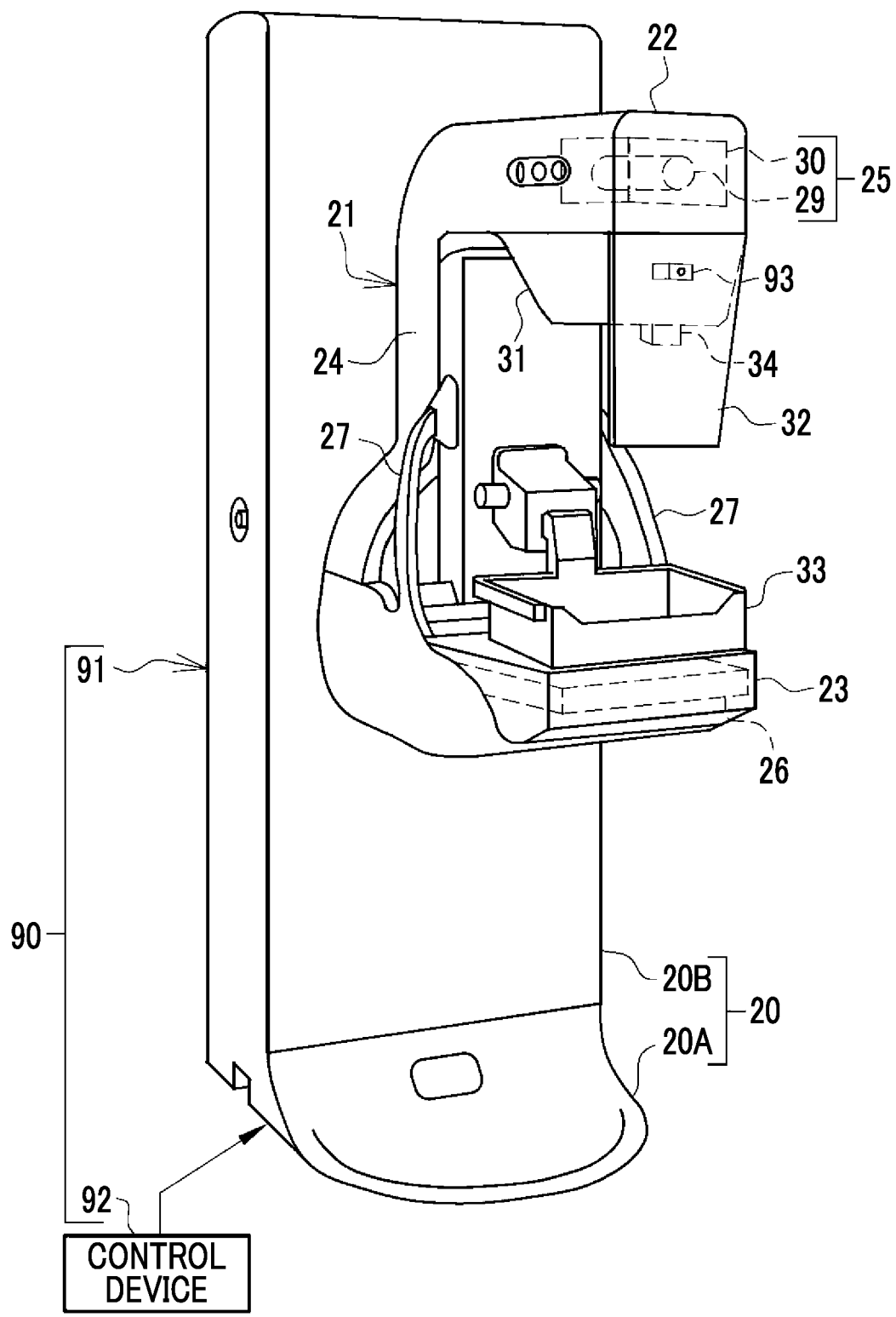
FIG. 22 is a diagram showing a breast imaging apparatus of a second_1 embodiment.

As an example, as shown in FIG. 22, a breast imaging apparatus 90 of a second_1 embodiment comprises an apparatus body 91 and a control device 92. The apparatus body 91 is different from the apparatus body 11 of the above-described first embodiment in that a camera 93 is incorporated on a side of the irradiation field limiter 31 facing the subject H. Other configurations are the same as those of the apparatus body 11 and are thus represented by the same reference numerals, and description thereof will not be repeated.

The camera 93 comprises an objective lens on the external surface of the irradiation field limiter 31 facing the subject H. The camera 93 incorporates an imaging sensor, such as a charge coupled device (CCD) image sensor or a complementary metal oxide semiconductor (CMOS) image sensor. The imaging sensor captures an object image taken by the objective lens and sequentially outputs a captured image 95 (see FIG. 23) at a predetermined frame rate, for example, 30 frames per second (fps). The object image is a scene of the radiography room 98 expanding in front of the breast imaging apparatus 90 on a side opposite to the stand 20 (see FIGS. 24 and 25).

Figure 23:
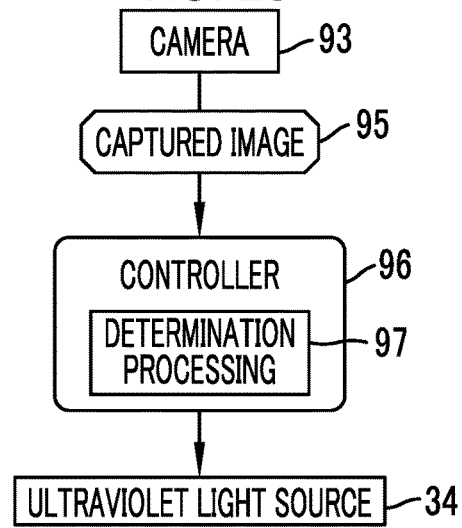
FIG. 23 is a diagram conceptually showing processing of a controller in the second_1 embodiment.

As an example, as shown in FIG. 23, the camera 93 outputs the captured image 95 to a controller 96 of the control device 92. The controller 96 executes determination processing 97 regarding whether or not a set condition for prohibiting the irradiation of the ultraviolet light UV by the ultraviolet light source 34 is satisfied, based on the captured image 95. The controller 96 controls the operation of the ultraviolet light source 34 corresponding to a determination result of the determination processing 97.

Figure 24:
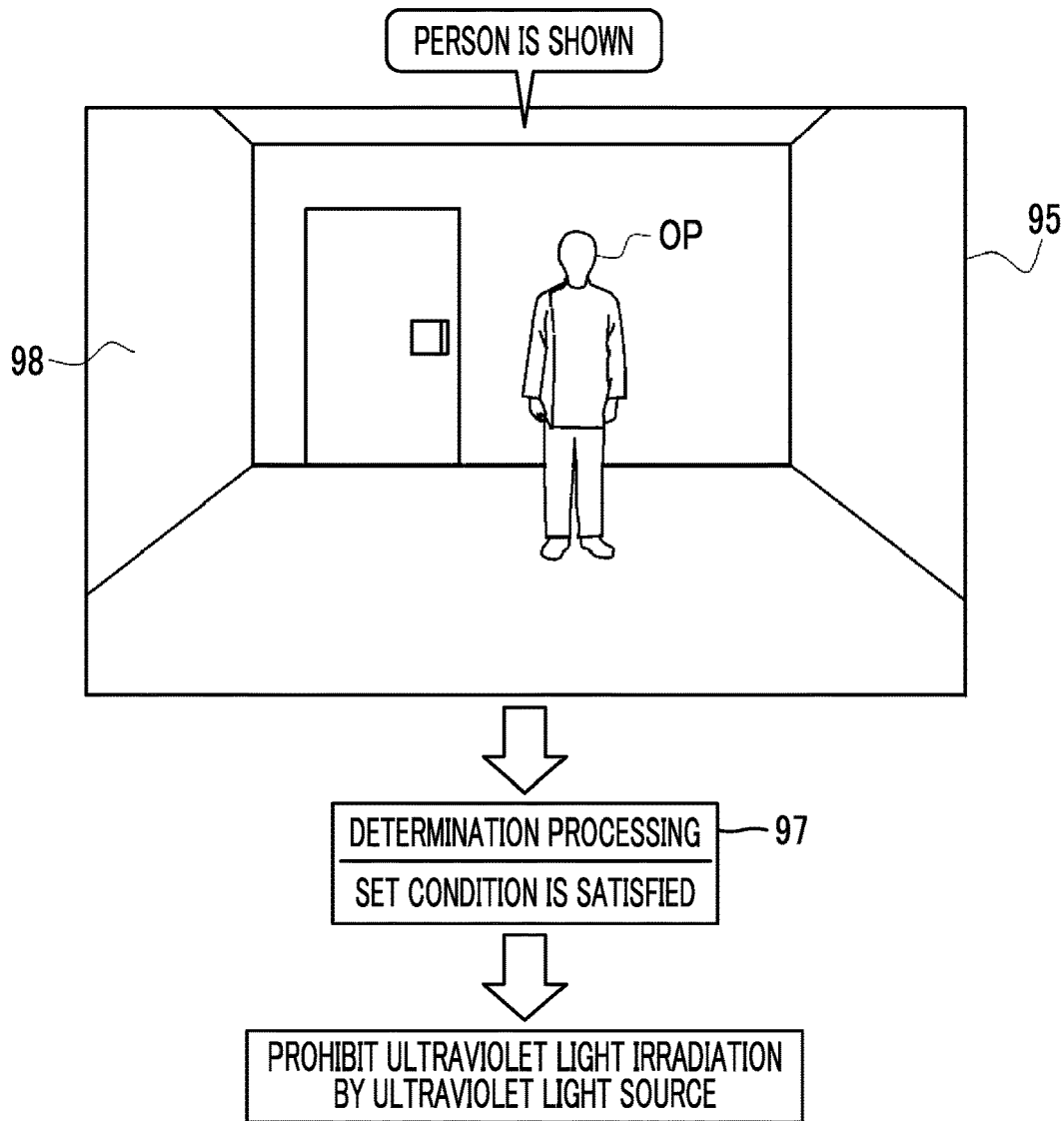
FIG. 24 is a diagram showing processing of the controller in a case where a person is shown in a captured image of a camera.

As an example, as shown in FIG. 24, in a case where a person, such as the operator OP, is shown in the captured image 95, the controller 96 determines that the set condition is satisfied. The controller 96 determines that the set condition is satisfied, for example, while a person is shown in the captured image 95. That is, the set condition in this case is that a person is shown in the captured image 95. In this case, the controller 96 prohibits the irradiation of the ultraviolet light UV by the ultraviolet light source 34. Here, "a person is shown" includes not only a case where the whole of the body of the person is shown but also a case where a portion of the body of the person is shown.

In contrast, as an example, as shown in FIG. 25, in a case where a person, such as the operator OP, is not shown in the captured image 95, the controller 96 determines that the set condition is not satisfied. In this case, the controller 96 permits the irradiation of the ultraviolet light UV by the ultraviolet light source 34.

As an example, as shown in FIG. 26, in a case where determination is made that the set condition is not satisfied, and the irradiation of the ultraviolet light UV is permitted, the controller 96 makes the ultraviolet light source 34 start the irradiation of the ultraviolet light UV. Then, when a predetermined first set period P1 has elapsed, the controller 96 makes the ultraviolet light source 34 stop the irradiation of the ultraviolet light UV. That is, in a case of making the ultraviolet light source 34 perform the irradiation of the ultraviolet light UV, the controller 96 makes the ultraviolet light source 34 continue the irradiation of the ultraviolet light UV for the first set period P1.

The first set period P1 is a period needed for inactivating bacterium or virus to be disinfected. The first set period P1 is different depending on irradiation energy of the ultraviolet light UV, a distance between the ultraviolet light source 34 and a place that is irradiated with the ultraviolet light UV, and a type of bacterium or virus to be disinfected, or the like, and is generally several seconds or several tens of minutes. For example, there is a report that novel coronavirus (Severe Acute Respiratory Syndrome (SARS)-Coronavirus (CoV)-2) is inactivated with the irradiation of the ultraviolet light UV for several seconds. In more detail, there is a report that, in a case of the ultraviolet light UV having a central wavelength of 222 nm and intensity of 1 W/m$^2$, 99.7% of novel coronavirus is inactivated with irradiation for 30 seconds (https://xtech.nikkei.com/atcl/nxt/news/18/08672/). There is also a report that, in a case of the ultraviolet light UV having a central wavelength of 254 nm, 99.9% of novel coronavirus is inactivated with irradiation for 10 seconds to 15 seconds (https://robotstart.info/2020/09/10/uvbuster-covid19.html).

Figure 27:
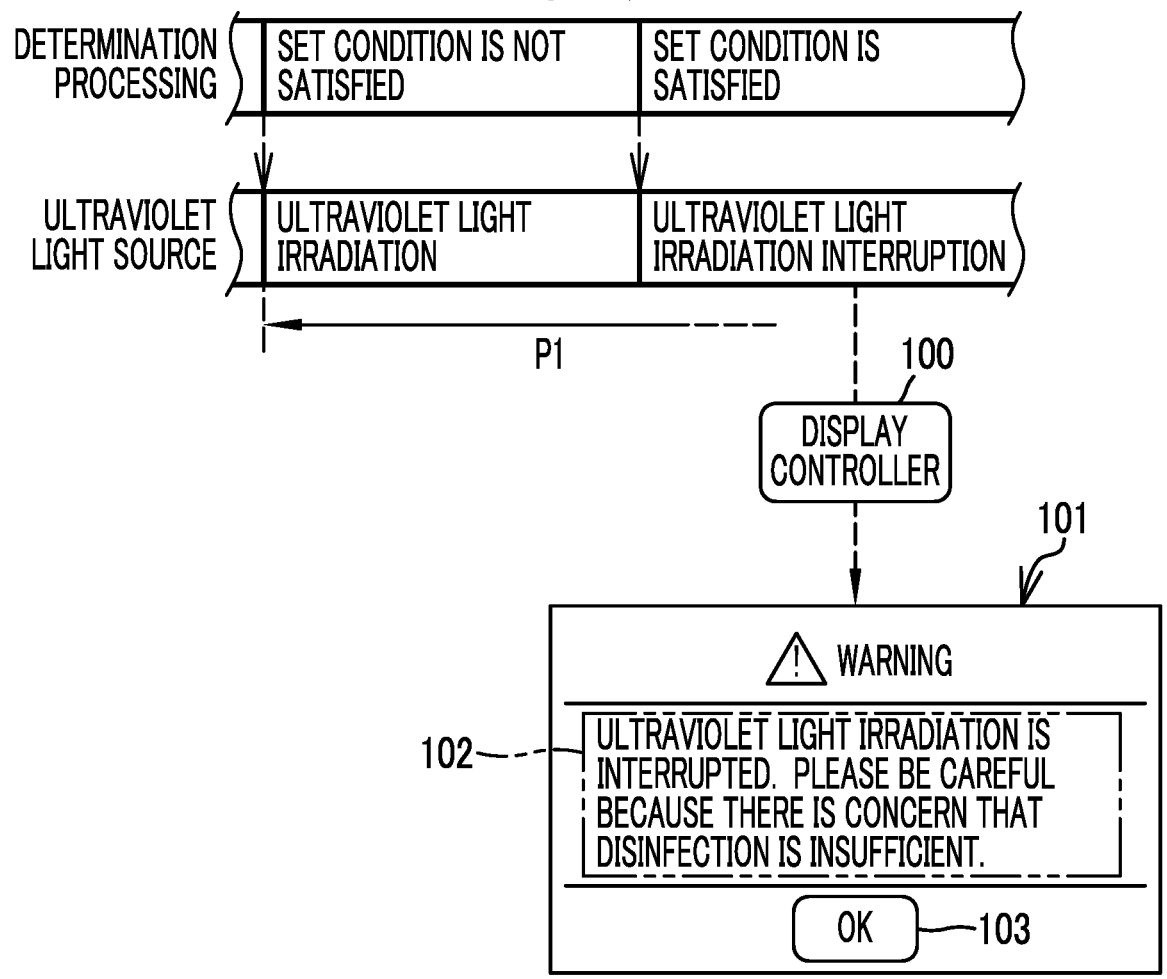
FIG. 27 is a diagram showing an aspect in which, in a case where determination is made that a set condition is satisfied before the first set period elapses, irradiation of ultraviolet light from the ultraviolet light source is interrupted and a warning window including a message indicating that irradiation of ultraviolet light is interrupted is displayed.

As an example, as shown in FIG. 27, in a case where a person is shown in the captured image 95 before the first set period P1 elapses and determination is made that the set condition is satisfied after determination is made that the set condition is not satisfied and the ultraviolet light source 34 is made to start the irradiation of the ultraviolet light UV, the controller 96 makes the ultraviolet light source 34 interrupt the irradiation of the ultraviolet light UV. In this case, a display controller 100 of the control device 92 displays a warning window 101 on the display 58. The warning window 101 includes a message 102 indicating that the irradiation of the ultraviolet light UV is interrupted and there is a concern that disinfection is insufficient. That is, the display controller 100 is an example of a "first notification controller" according to the technique of the present disclosure. The display of the warning window 101 is erased with selection of an OK button 103. Notification that the irradiation of the ultraviolet light UV is interrupted may be given by playing a voice message indicating that the irradiation of the ultraviolet light UV is interrupted, or the like. In this case, a voice controller that controls the play of the voice message operates as the first notification controller.

Figure 28:
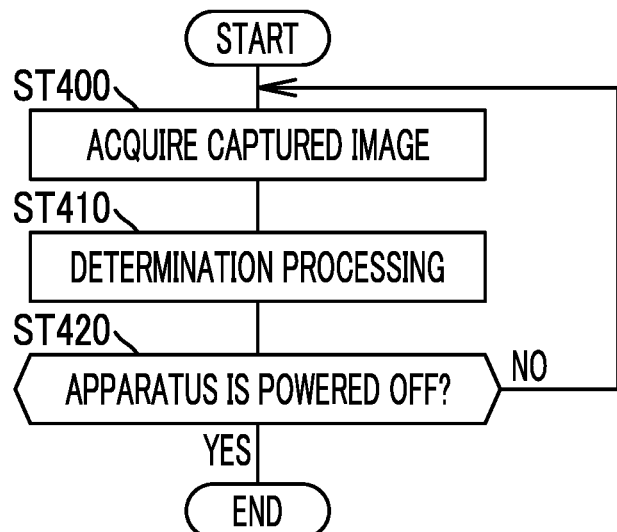
FIG. 28 is a flowchart showing a processing procedure of the control device in the second_1 embodiment.

Next, operations of an aspect shown in FIGS. 22 to 27 will be described referring to flowcharts shown in FIGS. 28 to 30. First, as an example, as shown in FIG. 28, in the controller 96, the captured image 95 from the camera 93 is acquired (Step ST400). Then, in the controller 96, the determination processing 97 is executed based on the captured image 95 (Step ST410). The processing of Steps ST400 and ST410 is continuously repeated while the breast imaging apparatus 90 is not powered off (in Step ST420, NO).

Figure 29:
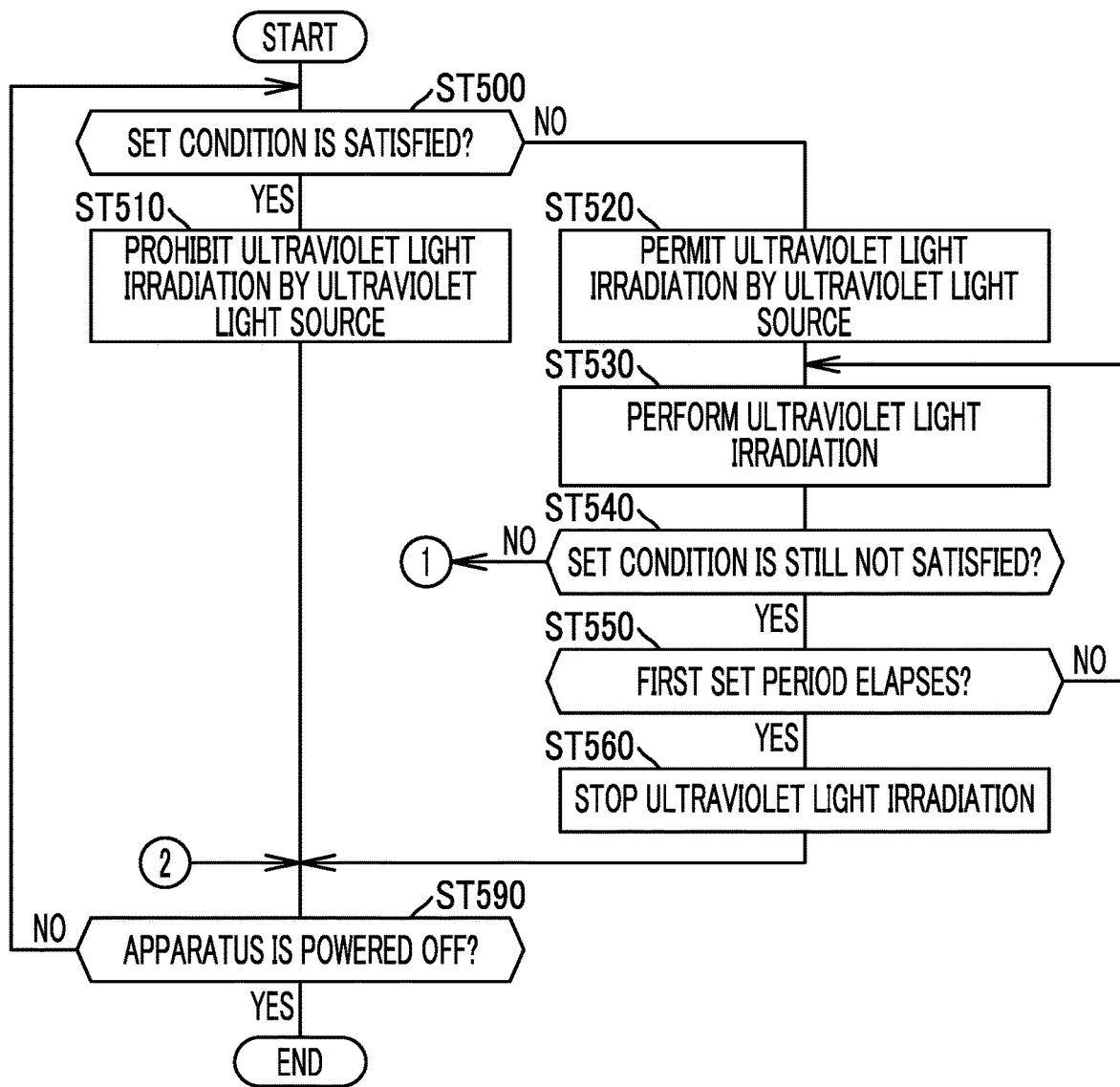
FIG. 29 is a flowchart showing a processing procedure of the control device in the second_1 embodiment.

As an example, as shown in FIG. 29, in a state in which the irradiation of the ultraviolet light UV is not performed, in a case where a person is shown in the captured image 95 and determination is made in the determination processing 97 that the set condition is satisfied (in Step ST500, YES), the irradiation of the ultraviolet light UV by the ultraviolet light source 34 is prohibited by the controller 96 (Step ST510).

In contrast, in a case where a person is not shown in the captured image 95 and determination is made in the determination processing 97 that the set condition is not satisfied (in Step ST500, NO), the irradiation of the ultraviolet light UV by the ultraviolet light source 34 is permitted by the controller 96 (Step ST520). Then, the irradiation of the ultraviolet light UV by the ultraviolet light source 34 is started under the control of the controller 96 (Step ST530). The irradiation of the ultraviolet light UV is continued while determination is still made in the determination processing 97 that the set condition is not satisfied (in Step ST540, YES), and the first set period P1 has not elapsed (in Step ST550, NO). After the first set period P1 has elapsed (in Step ST550, YES), the irradiation of the ultraviolet light UV by the ultraviolet light source 34 is stopped by the controller 96 (Step ST560).

Figure 30:
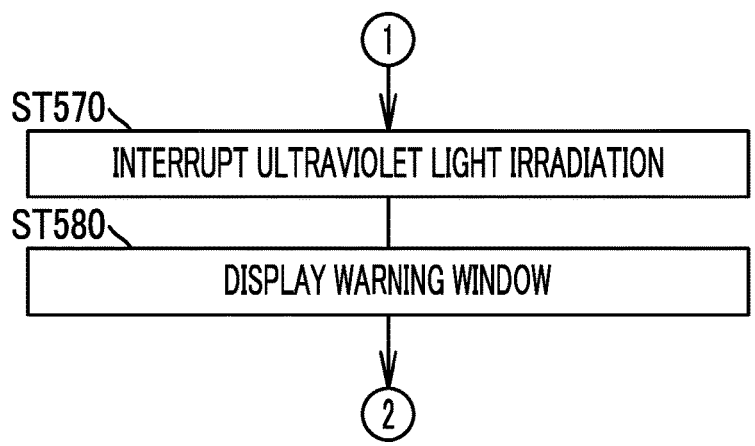
FIG. 30 is a flowchart showing a processing procedure of the control device in the second_1 embodiment.

On the other hand, before the first set period P1 elapses, determination is made in the determination processing 97 that the set condition is satisfied (in Step ST540, NO), as an example, as shown in FIG. 30, the irradiation of the ultraviolet light UV by the ultraviolet light source 34 is interrupted by the controller 96 (Step ST570). Then, the warning window 101 including the message 102 indicating that the irradiation of the ultraviolet light UV is interrupted is displayed on the display 58 by the display controller 100 (Step ST580). A series of processing is continuously repeated while the breast imaging apparatus 90 is not powered off (in Step ST590, NO).

As described above, the controller 96 of the breast imaging apparatus 90 prohibits the irradiation of the ultraviolet light UV by the ultraviolet light source 34 in a case where the predetermined set condition is satisfied. Accordingly, it is possible to perform disinfection by the irradiation of the ultraviolet light UV while reducing a concern that a human body is irradiated with the ultraviolet light UV.

As shown in FIGS. 22 to 24, the breast imaging apparatus 90 comprises the camera 93, and the controller 96 determines that the set condition is satisfied in a case where a person is shown in the captured image 95 of the camera 93. For this reason, it is possible to further reduce a concern that a human body is irradiated with the ultraviolet light UV. The camera 93 may be provided in the column 20B. The camera 93 may not be incorporated in the apparatus body 91 or may be attached to, for example, a place separated from the apparatus body 91, such as the wall surface or the ceiling of the radiography room 98. In this case, it is preferable that communication with the control device 92 is performed in a wireless manner.

As shown in FIG. 26, in making the ultraviolet light source 34 perform the irradiation of the ultraviolet light UV, the controller 96 makes the ultraviolet light source 34 continue the irradiation of the ultraviolet light UV for the predetermined first set period P1. For this reason, it is possible to perform the irradiation of the ultraviolet light UV needed for inactivating bacterium or virus to be disinfected.

As shown in FIG. 27, the controller 96 makes the ultraviolet light source 34 interrupt the irradiation of the ultraviolet light UV in a case where determination is made that the set condition is satisfied before the first set period P1 elapses. For this reason, it is possible to further reduce a concern that a human body is irradiated with the ultraviolet light UV. The display controller 100 notifies that the irradiation of the ultraviolet light UV is interrupted, by displaying the warning window 101 on the display 58. For this reason, the operator OP can know that the irradiation of the ultraviolet light UV is interrupted. The operator OP can take measure moving a person out of the radiography room 98 and restarting the irradiation of the ultraviolet light UV.

A captured image may be acquired from a surveillance camera provided in the radiography room 98. That is, the breast imaging apparatus 90 may not comprise a camera. A management apparatus of the surveillance camera provided in the radiography room 98 may detect whether or not a person is shown in the captured image, and the control device 92 may receive a detection result from the management apparatus.

Figure 31:
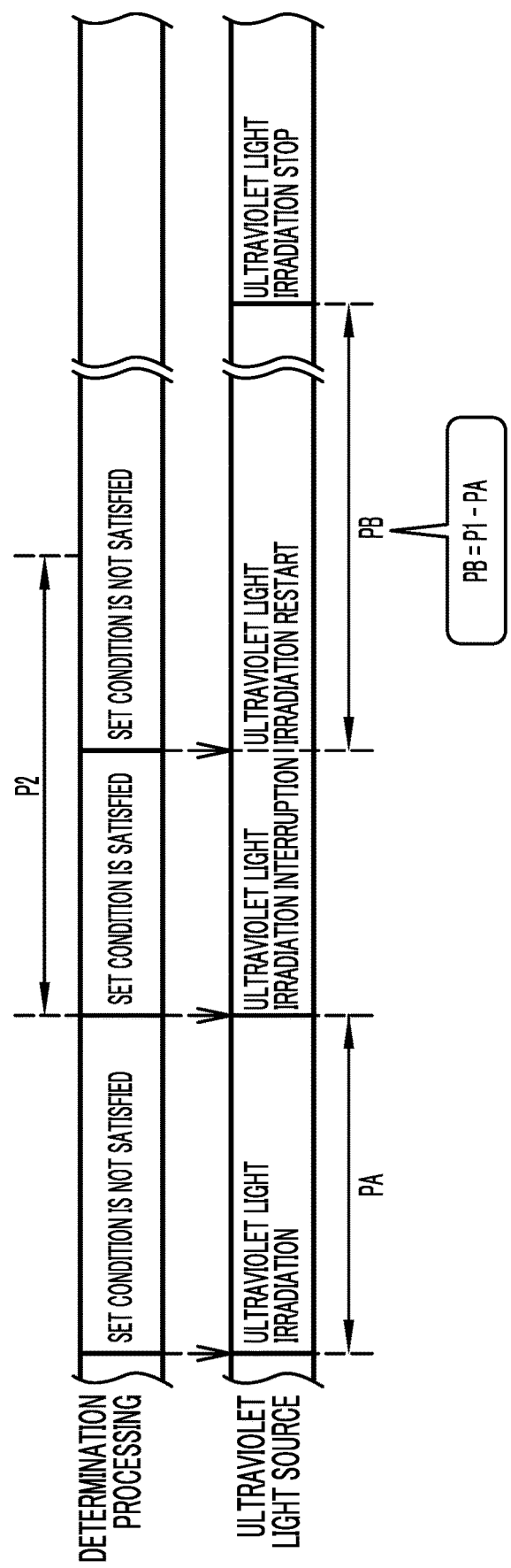
FIG. 31 is a diagram showing an aspect in which irradiation of ultraviolet light from the ultraviolet light source is restarted in a case where determination is made that the set condition is not satisfied within a predetermined second set period after irradiation of ultraviolet light is interrupted.
Figure 32:
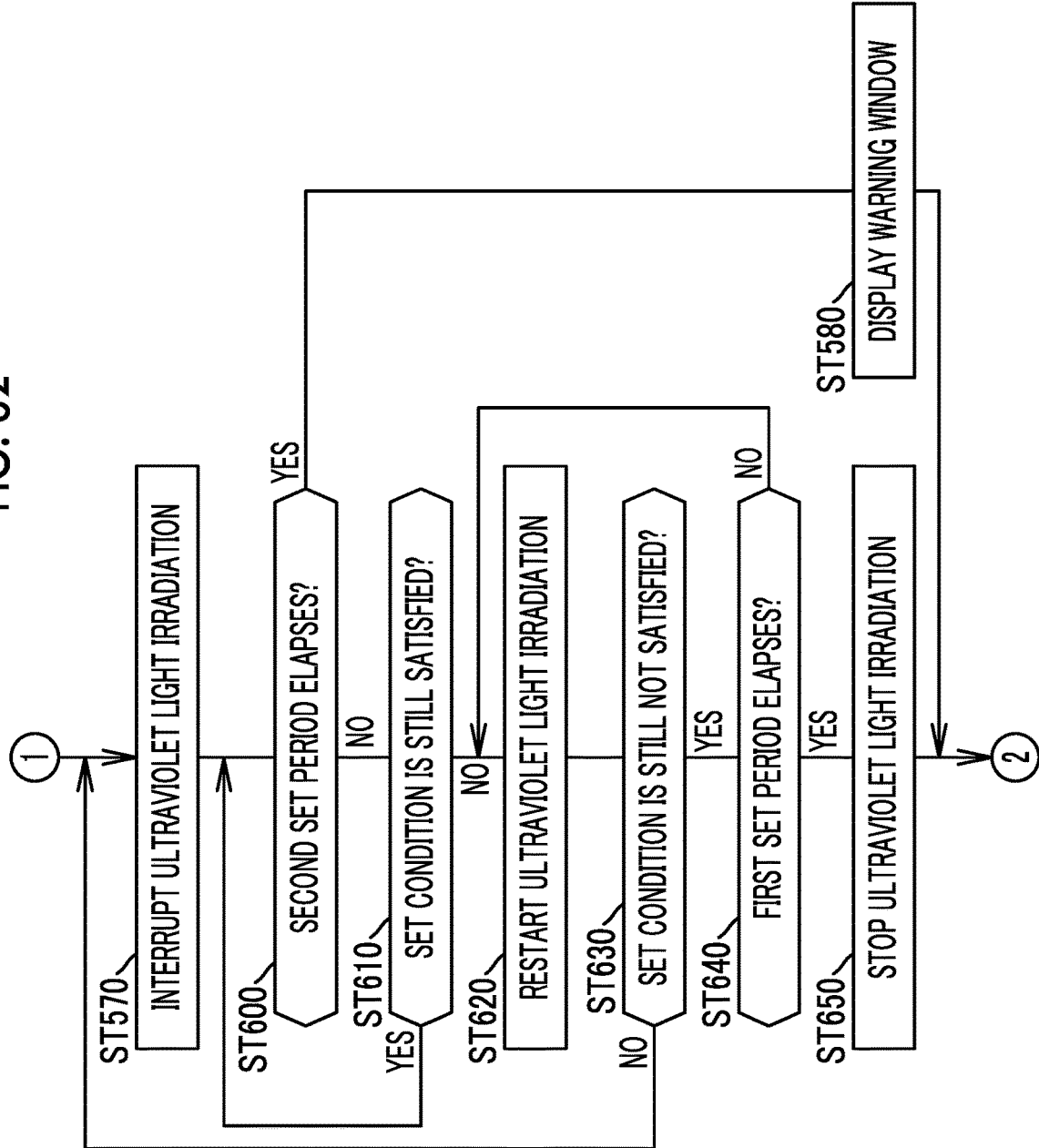
FIG. 32 is a flowchart showing a processing procedure of the control device in the aspect of FIG. 31.

An aspect shown in FIGS. 31 and 32 may be employed.

As an example, as shown in FIG. 31, in a case where determination is made that the set condition is not satisfied within a predetermined second set period P2 after the irradiation of the ultraviolet light UV is interrupted, the controller 96 makes the ultraviolet light source 34 restart the irradiation of the ultraviolet light UV. Then, after a period PB has elapsed, the irradiation of the ultraviolet light UV is stopped. The period PB is a period (PB=P1−PA) obtained by subtracting a period PA for which the irradiation of the ultraviolet light UV is performed before the irradiation of the ultraviolet light UV is interrupted, from the first set period P1. The second set period P2 is, for example, several seconds to several minutes.

As an example, as shown in FIG. 32, in a case where determination is made in the determination processing 97 that the set condition is satisfied before the first set period P1 elapses, the irradiation of the ultraviolet light UV by the ultraviolet light source 34 is interrupted by the controller 96 (Step ST570). In a case where the second set period P2 has elapsed after the irradiation of the ultraviolet light UV has been interrupted (in Step ST600, YES), the warning window 101 including the message 102 indicating the irradiation of the ultraviolet light UV is interrupted is displayed on the display 58 by the display controller 100 (Step ST580). Thereafter, in a case where the controller 96 determines that the set condition is not satisfied, and permits the irradiation of the ultraviolet light UV by the ultraviolet light source 34, the period PA for which the irradiation of the ultraviolet light UV is performed before irradiation is interrupted is reset, and the irradiation of the ultraviolet light UV is started from the beginning of the first set period P1.

In a case where the second set period P2 has not elapsed after the irradiation of the ultraviolet light UV has been interrupted (in Step ST600, NO), and in a case where determination is made in the determination processing 97 that the set condition is not satisfied (in Step ST610, NO), the irradiation of the ultraviolet light UV by the ultraviolet light source 34 is restarted by the controller 96 (Step ST620). The irradiation of the ultraviolet light UV is continued while determination is still made in the determination processing 97 that the set condition is not satisfied (in Step ST630, YES), and the first set period P1 has not elapsed (in Step ST640, NO). In a case where determination is made in the determination processing 97 that the set condition is satisfied (in Step ST630, NO), the irradiation of the ultraviolet light UV is interrupted again (Step ST570). After the first set period P1 has elapsed (in Step ST640, YES), the irradiation of the ultraviolet light UV by the ultraviolet light source 34 is stopped by the controller 96 (Step ST650).

In this way, in the aspect shown in FIGS. 31 and 32, in a case where determination is made the set condition is not satisfied within the predetermined second set period P2 after the irradiation of the ultraviolet light UV is interrupted, the controller 96 makes the ultraviolet light source 34 restart the irradiation of the ultraviolet light UV. For this reason, it is possible to restart the irradiation of the ultraviolet light UV without depending on the hand of the operator OP. It is also possible to accomplish disinfection by the irradiation of the ultraviolet light UV as much as possible, and to reduce opportunities that the breast imaging apparatus 10 is used with insufficient disinfection.

Although the warning window 101 is displayed in a case where the second set period P2 has elapsed after the irradiation of the ultraviolet light UV has been interrupted, the technique of the present disclosure is not limited thereto. The warning window 101 may be displayed immediately after the irradiation of the ultraviolet light UV is interrupted. In this case, in a case where the irradiation of the ultraviolet light UV is restarted before the OK button 103 of the warning window 101 is selected, the display of the warning window 101 is erased without waiting for the selection of the OK button 103. Then, it is possible to save labor of the operator OP for selecting the OK button 103.

In a case where the controller 96 determines that the set condition is not satisfied, the ultraviolet light source 34 may be made to continuously perform the irradiation of the ultraviolet light UV without providing a restriction, such as the first set period P1.

Second_2 Embodiment

Figure 33:
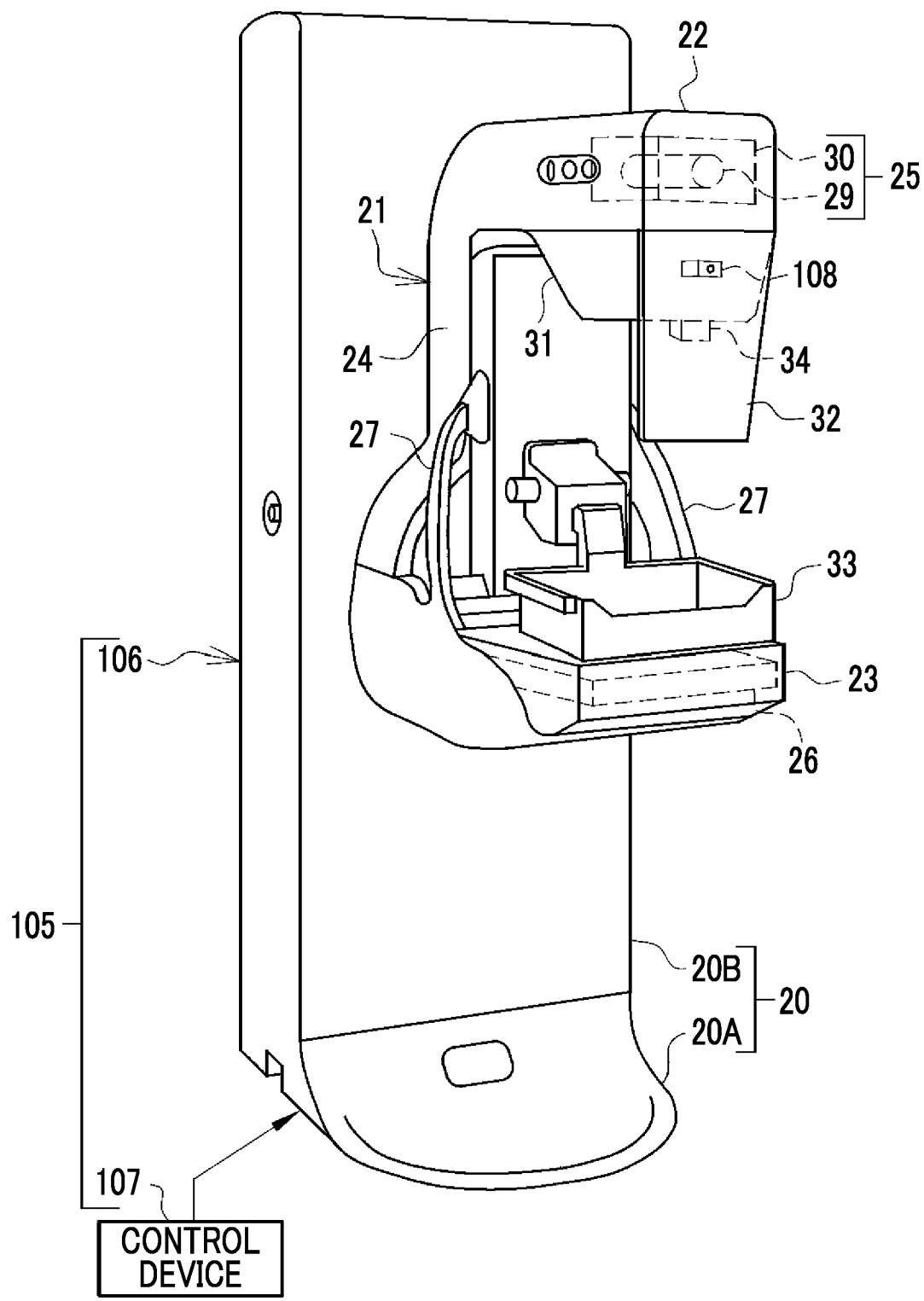
FIG. 33 is a diagram showing a breast imaging apparatus of a second_2 embodiment.

As an example, as shown in FIG. 33, a breast imaging apparatus 105 of a second_2 embodiment comprises an apparatus body 106 and a control device 107. The apparatus body 106 is different from the apparatus body 91 of the second_1 embodiment in that a moving body detection sensor 108, instead of the camera 93, is incorporated on the side of the irradiation field limiter 31 facing the subject H. Other configurations are the same as those of the apparatus body 91 and are thus represented by the same reference numerals, and description thereof will not be repeated.

The moving body detection sensor 108 is provided with a detection window on the external surface of the irradiation field limiter 31 facing the subject H. The moving body detection sensor 108 is a sensor that detects a moving body using change in infrared light, change in reflected ultrasonic wave, shielding of visible light, or the like, and is generally referred to as a human sensor. The moving body detection sensor 108 detects a moving body in the radiography room 98. The moving body detection sensor 108 outputs a moving body detection signal 110 (see FIG. 34) in a case where a moving body is detected.

Figure 34:
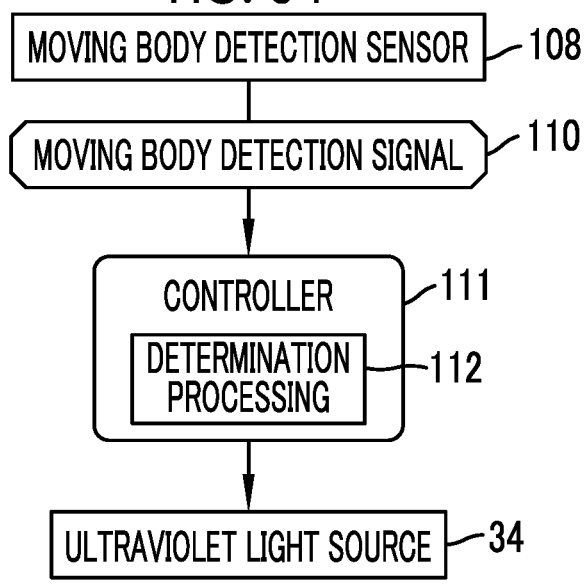
FIG. 34 is a diagram conceptually showing processing of a controller in the second_2 embodiment.

As an example, as shown in FIG. 34, the moving body detection sensor 108 outputs the moving body detection signal 110 to a controller 111 of the control device 107. The controller 111 executes determination processing 112 regarding whether or not a set condition for prohibiting the irradiation of the ultraviolet light UV by the ultraviolet light source 34 is satisfied based on the moving body detection signal 110. The controller 111 controls the operation of the ultraviolet light source 34 corresponding to a determination result of the determination processing 112.

Figure 35:
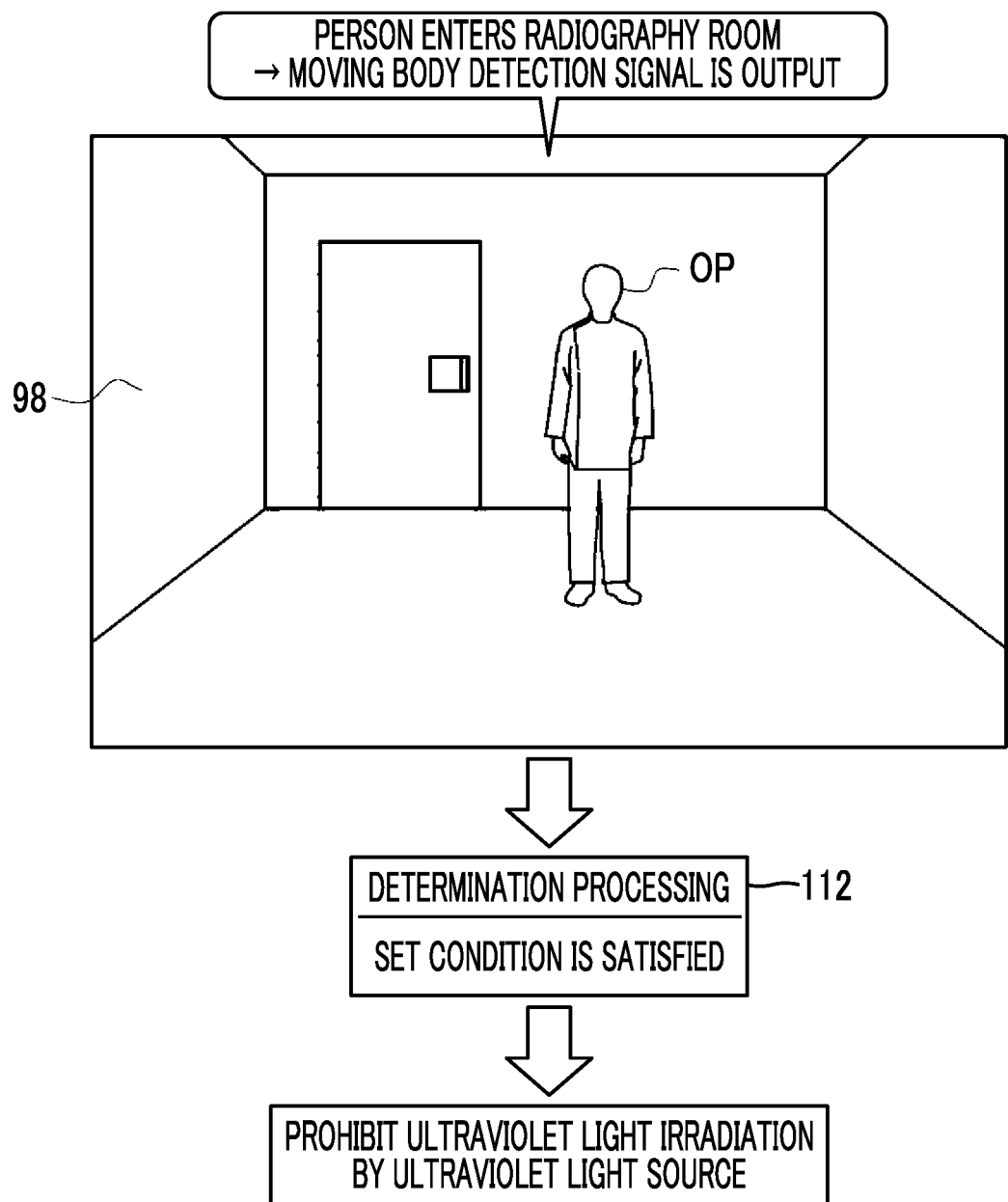
FIG. 35 is a diagram showing processing of the controller in a case where a moving body detection signal is output from a moving body detection sensor.

As an example, as shown in FIG. 35, in a case where a person, such as the operator OP, enters the radiography room 98, and the moving body detection signal 110 is output from the moving body detection sensor 108, the controller 111 determines that the set condition is satisfied. The controller 111 determines that the set condition is satisfied, for example, until a predetermined set period elapses after the moving body detection signal 110 is received. That is, the set condition in this case is that the moving body detection sensor 108 detects a moving body. In this case, the controller 111 prohibits the irradiation of the ultraviolet light UV by the ultraviolet light source 34. The set period is an average period required, for example, for single imaging of the radiographic image RI.

Figure 36:
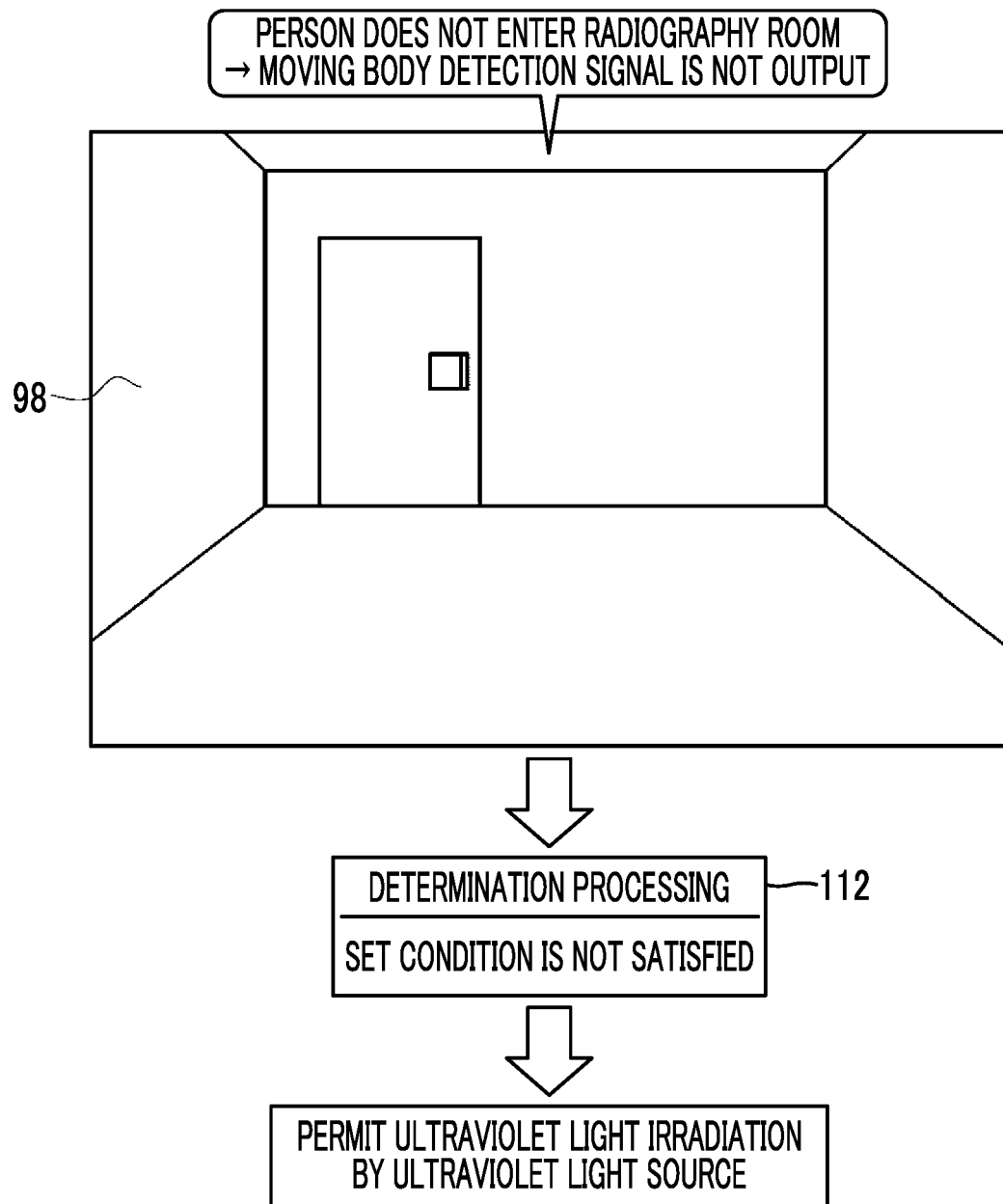
FIG. 36 is a diagram showing processing of the controller in a case where the moving body detection signal is not output from the moving body detection sensor.

In contrast, as an example, as shown in FIG. 36, in a case where a person, such as the operator OP, does not enter the radiography room 98, and the moving body detection signal 110 is not output from the moving body detection sensor 108, the controller 111 determines that the set condition is not satisfied. In this case, the controller 111 permits the irradiation of the ultraviolet light UV by the ultraviolet light source 34.

In this way, the breast imaging apparatus 105 comprises the moving body detection sensor 108 that detects a moving body, and the controller 111 determines that the set condition is satisfied in a case where the moving body detection sensor 108 detects a moving body. For this reason, it is possible to further reduce a concern that a human body is irradiated with the ultraviolet light UV. The moving body detection sensor 108 is inexpensive compared to the camera 93 of the above-described second_1 embodiment, and does not need to analyze the captured image 95 to detect whether or not a person is shown. Similarly to the camera 93, the moving body detection sensor 108 may be provided in the column 20B. The moving body detection sensor 108 may not be incorporated in the apparatus body 106 or may be attached to, for example, a place separated from the apparatus body 106, such as the wall surface or the ceiling of the radiography room 98. In this case, it is preferable that communication with the control device 92 is performed in a wireless manner.

A detection range of the moving body detection sensor 108 may be set as, for example, a comparatively narrow range, such as 1 m in the surrounding of the breast imaging apparatus 105. Alternatively, as the moving body detection sensor 108, for example, a contact detection sensor that detects contact of a person on the apparatus body 106 may be used. Then, for example, in a case where the operator OP enters the radiography room 98 for a thing to do without approaching the breast imaging apparatus 105, it is possible to prevent the irradiation of the ultraviolet light UV from being prohibited. Alternatively, a voice detection sensor that detects sound, such as voice, may be used as the moving body detection sensor 108.

A transmissive photo-interrupter that is configured with a light projector and a light receiver may be used as the moving body detection sensor 108. In this case, for example, a photo-interrupter is provided at an entrance of the radiography room 98 to detect entrance of a person to the radiography room 98 and exit of a person from the radiography room 98. As the photo-interrupter, for example, "Safety Light Curtain" (Product Name, manufactured by OMRON Inc.) can be used.

Second_3 Embodiment

Figure 37:
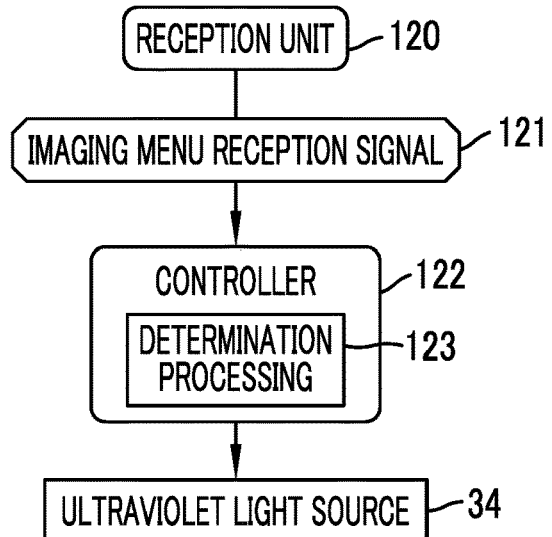
FIG. 37 is a diagram conceptually showing processing of a controller in a second_3 embodiment.

As an example, as shown in FIG. 37, a reception unit 120 of a second_3 embodiment outputs an imaging menu reception signal 121 to a controller 122 in a case where the imaging menu 80 input by the operator OP through the input device 59 is received. The controller 122 executes determination processing 123 regarding whether or not a set condition for prohibiting the irradiation of the ultraviolet light UV by the ultraviolet light source 34 is satisfied based on the imaging menu reception signal 121. The controller 122 controls the operation of the ultraviolet light source 34 corresponding to a determination result of the determination processing 123.

Figure 38:
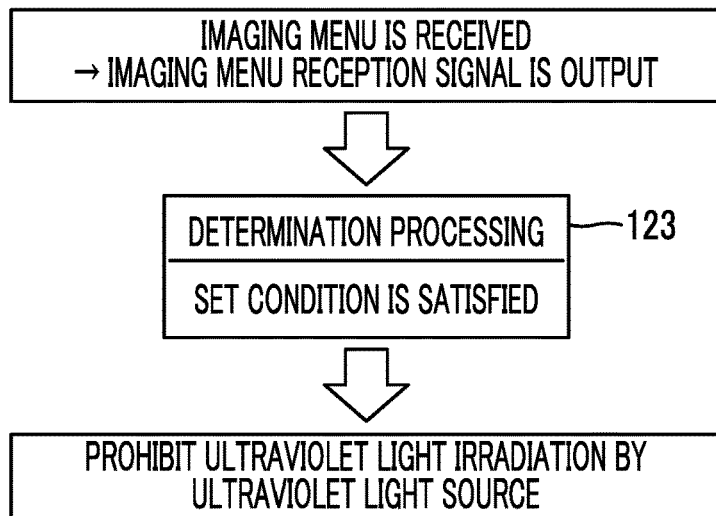
FIG. 38 is a diagram showing processing of the controller in a case where an imaging menu reception signal is output from a reception unit.

As an example, as shown in FIG. 38, in a case where the imaging menu 80 is input by the operator OP through the input device 59, the imaging menu 80 is received in the reception unit 120, and the imaging menu reception signal 121 is output from the reception unit 120, the controller 122 determines that the set condition is satisfied. The controller 122 determines that the set condition is satisfied, for example, until a predetermined set period elapses after the imaging menu reception signal 121 is received. That is, the set condition in this case is that the reception unit 120 receives the imaging menu 80. In this case, the controller 122 prohibits the irradiation of the ultraviolet light UV by the ultraviolet light source 34. The set period is an average period required, for example, for single imaging of the radiographic image RI.

Figure 39:
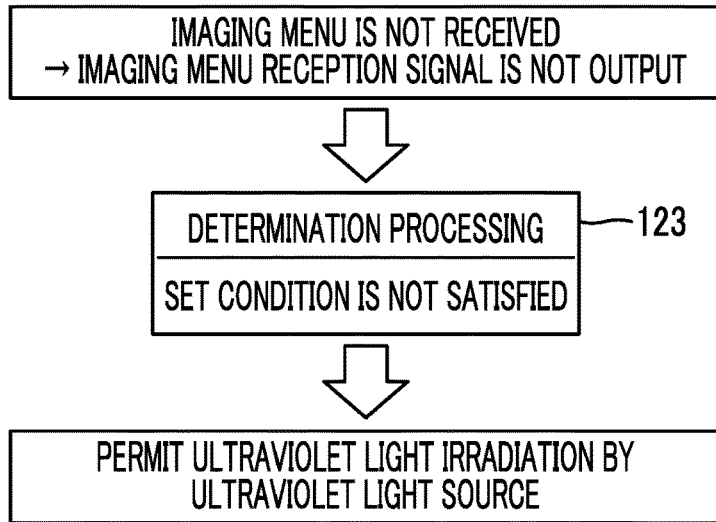
FIG. 39 is a diagram showing processing of the controller in a case where the imaging menu reception signal is not output from the reception unit.

In contrast, as an example, as shown in FIG. 39, in a case where the imaging menu 80 is not received in the reception unit 120, and the imaging menu reception signal 121 is not output from the reception unit 120, the controller 122 determines that the set condition is not satisfied. In this case, the controller 122 permits the irradiation of the ultraviolet light UV by the ultraviolet light source 34.

In this way, the controller 122 determines that the set condition is satisfied in a case where the reception unit 120 receives the imaging menu 80. Soon after the reception unit 120 receives the imaging menu 80, the subject H enters the radiography room 98, and imaging of the radiographic image RI is performed. For this reason, it is possible to further reduce a concern that a human body is irradiated with the ultraviolet light UV. There is no need to provide the camera 93 of the above-described second_1 embodiment and the moving body detection sensor 108 of the above-described second_2 embodiment.

The above-described second_1 embodiment and the second_3 embodiment or the above-described second_2 embodiment and the second_3 embodiment may be embodied in combination. In a case where the above-described second_1 embodiment and the second_3 embodiment are embodied in combination, in a case where a person is shown in the captured image 95 or in a case where the reception unit 120 receives the imaging menu 80, the controller determines that the set condition is satisfied. In a case where the above-described second_2 embodiment and the second_3 embodiment are embodied in combination, in a case where the moving body detection sensor 108 detects a moving body or in a case where the reception unit 120 receives the imaging menu 80, the controller determines that the set condition is satisfied.

In a case where the imaging menu 80 for imaging different subjects H between previous imaging and present imaging is received, the controller 122 makes the ultraviolet light source 34 perform the irradiation of the ultraviolet light UV before present imaging. On the other hand, in a case where the imaging menu 80 for imaging the identical subject H between previous imaging and present imaging is received, the controller 122 may not make the ultraviolet light source 34 perform the irradiation of the ultraviolet light UV before present imaging. In a case of imaging the identical subject H, there is no concern that bacterium and/or virus infects another subject H. Thus, the irradiation of the ultraviolet light UV is not performed, and power consumption is reduced.

Second_4 Embodiment

In a second_4 embodiment shown in FIGS. 40 to 44, in a case where an operation mode is switched from a first operation mode MD1 where power consumption is relatively high to a second operation mode MD2 where power consumption is relatively low, determination is made that a set condition is not satisfied.

Figure 40:
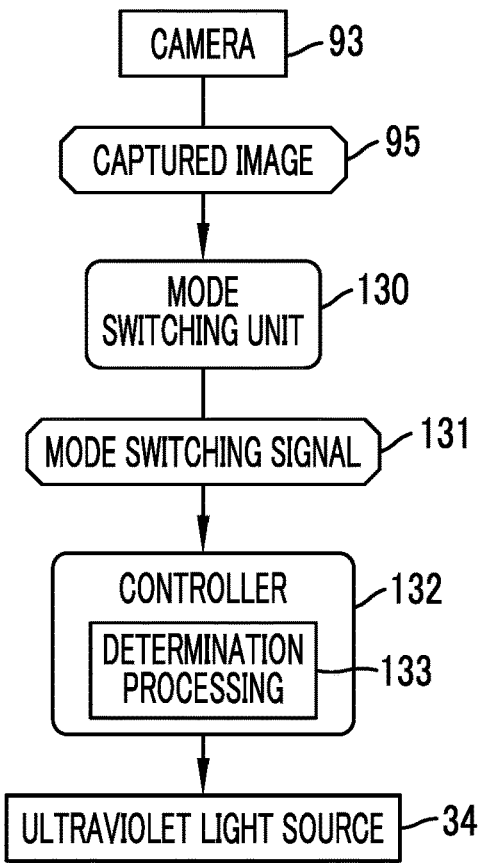
FIG. 40 is a diagram conceptually showing processing of a mode switching unit and a controller in a second_4 embodiment.

As an example, as shown in FIG. 40, the camera 93 outputs the captured image 95 to a mode switching unit 130. The mode switching unit 130 is a processing unit that is constructed in a CPU of a control device along with a controller 132 and the like, and switches the operation mode of the breast imaging apparatus based on the captured image 95. The mode switching unit 130 outputs a mode switching signal 131 to the controller 132. The controller 132 executes determination processing 133 regarding whether or not a set condition for prohibiting the irradiation of the ultraviolet light UV by the ultraviolet light source 34 is satisfied based on the mode switching signal 131. The controller 132 controls the operation of the ultraviolet light source 34 corresponding to a determination result of the determination processing 133.

Figure 41:
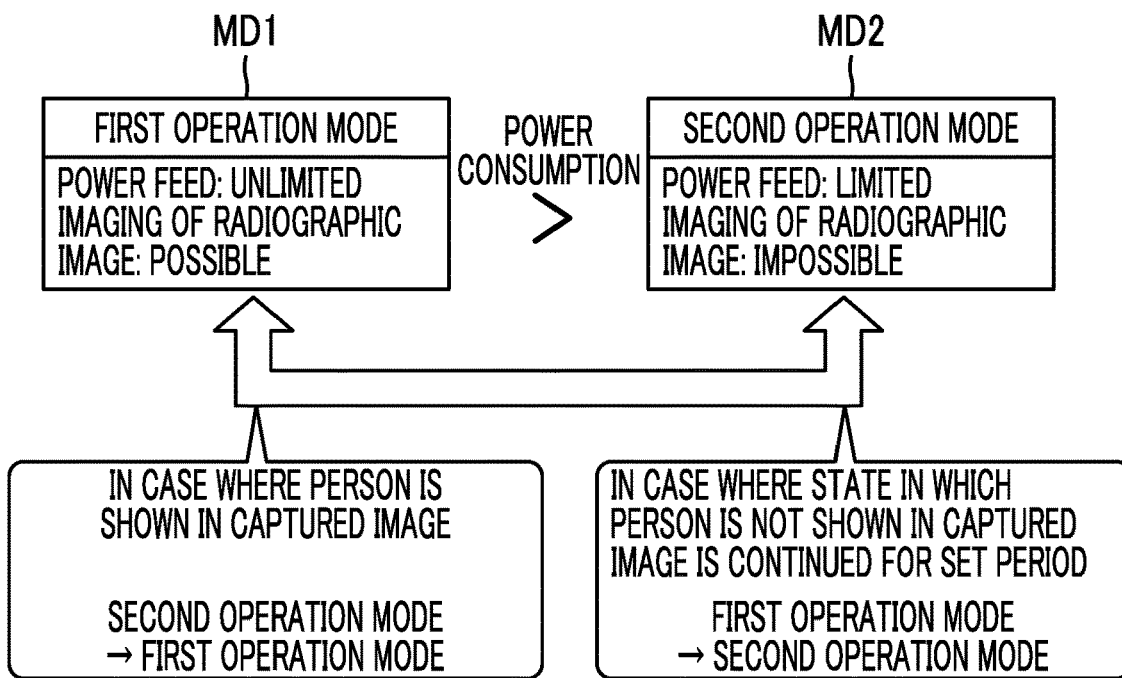
FIG. 41 is a diagram showing a scene in which a first operation mode and a second operation mode are switched based on the captured image of the camera.

As an example, as shown in FIG. 41, the mode switching unit 130 switches between the first operation mode MD1 and the second operation mode MD2. In the first operation mode MD1, power feed to each unit is unlimited, and imaging of the radiographic image RI is possible. On the other hand, in the second operation mode MD2, power feed to each unit is limited, and imaging of the radiographic image RI is impossible. In the second operation mode MD2, power feed to each unit is limited, and thus, power consumption is lower than in the first operation mode MD1. That is, the first operation mode MD1 is a so-called normal operation mode, and the second operation mode MD2 is a so-called power saving mode.

In a state of the first operation mode MD1, in a case where a state in which a person is not shown in the captured image 95 is continued for a predetermined set period, the mode switching unit 130 switches the operation mode from the first operation mode MD1 to the second operation mode MD2. On the other hand, in a state of the second operation mode MD2, in a case where a person is shown in captured image 95, the mode switching unit 130 switches the operation mode from the second operation mode MD2 to the first operation mode MD1. The set period in this case is, for example, 10 minutes.

Figure 42:
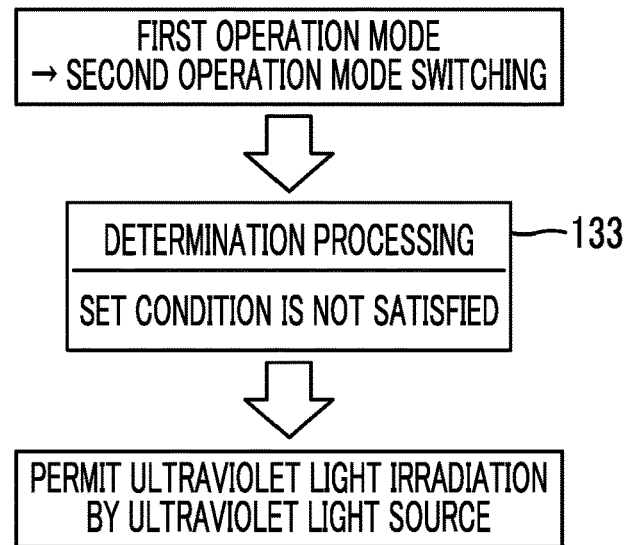
FIG. 42 is a diagram showing processing of the controller in a case where an operation mode is switched from the first operation mode to the second operation mode.

As an example, as shown in FIG. 42, in a case where the mode switching unit 130 switches the operation mode from the first operation mode MD1 to the second operation mode MD2, the controller 132 determines that the set condition is not satisfied. In this case, the controller 132 permits the irradiation of the ultraviolet light UV by the ultraviolet light source 34.

In this case, in the second_4 embodiment, the mode switching unit 130 that switches between the first operation mode MD1 where power consumption is relatively high and the second operation mode MD2 where power consumption is relatively low is provided. In a case where the mode switching unit 130 switches the operation mode to the second operation mode MD2, the controller 132 determines that the set condition is not satisfied, and permits the irradiation of the ultraviolet light UV by the ultraviolet light source 34. The second operation mode MD2 is executed in a case where a state in which a person is not shown in the captured image 95 is continued for the set period, and determination is made that there is no imaging of the radiographic image RI for a while. For this reason, a non-operation period of the breast imaging apparatus during which there is no imaging of the radiographic image RI for a while can be allotted to disinfection by the irradiation of the ultraviolet light UV.

Figure 43:
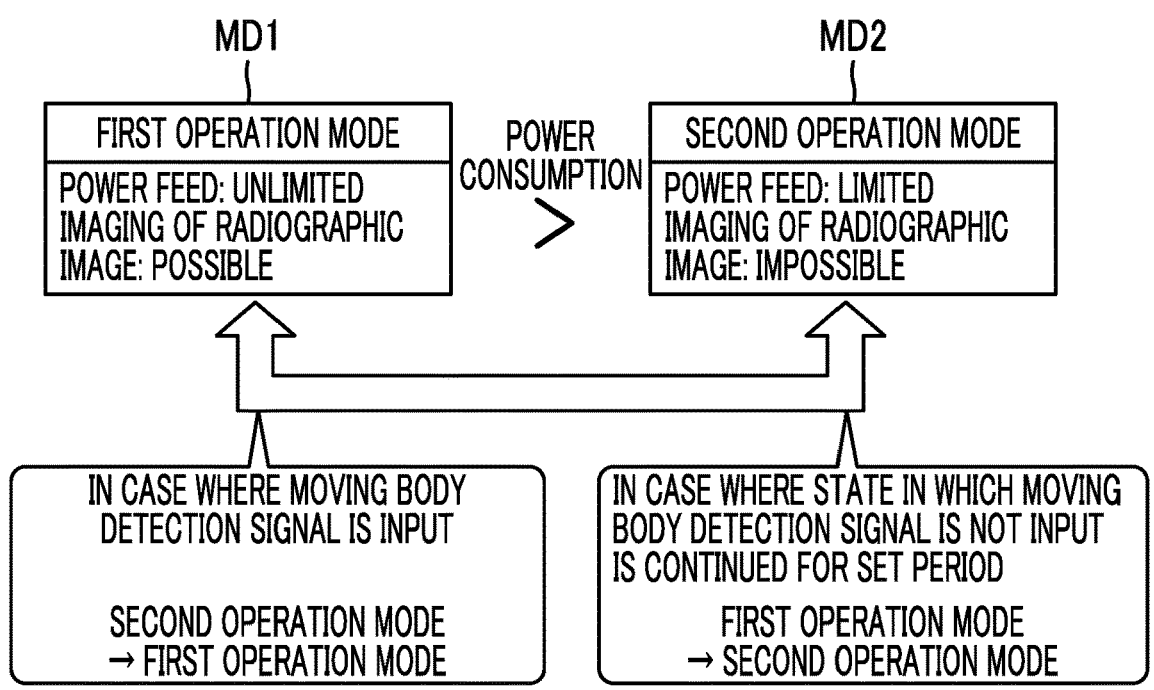
FIG. 43 is a diagram showing a scene in which the first operation mode and the second operation mode are switched based on the moving body detection signal from the moving body detection sensor.

A timing of switching the operation mode is not limited to a timing based on the captured image 95 exemplified above. For example, as shown in FIG. 43, the operation mode may be switched at a timing based on the moving body detection signal 110 from the moving body detection sensor 108. That is, in the state of the first operation mode MD1, in a case where a state in which the moving body detection signal 110 is not input from the moving body detection sensor 108 is continued for the set period, the mode switching unit 130 switches the operation mode from the first operation mode MD1 to the second operation mode MD2. On the other hand, in the state of the second operation mode MD2, in a case where the moving body detection signal 110 is input from the moving body detection sensor 108, the mode switching unit 130 switches the operation mode from the second operation mode MD2 to the first operation mode MD1.

Figure 44:
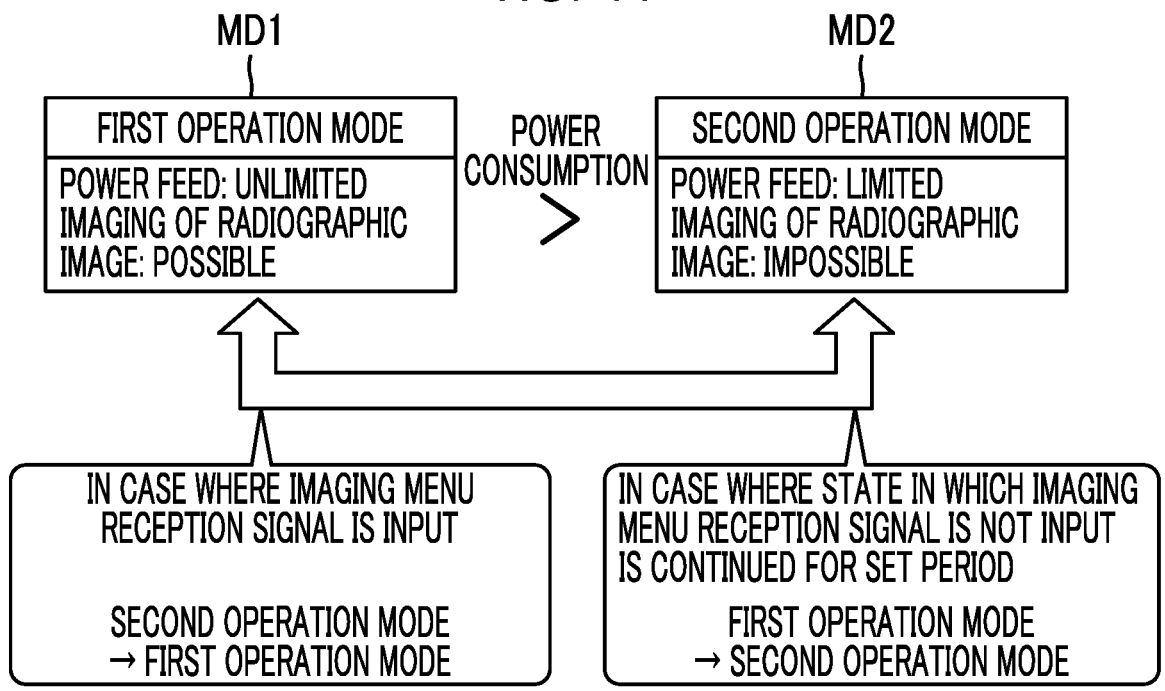
FIG. 44 is a diagram showing a scene in which the first operation mode and the second operation mode are switched based on the imaging menu reception signal from the reception unit.

Alternatively, as shown in FIG. 44, the operation mode may be switched at a timing based on the imaging menu reception signal 121 from the reception unit 120. That is, in the state of the first operation mode MD1, in a case where a state in which the imaging menu reception signal 121 is not input from the reception unit 120 is continued for the set period, the mode switching unit 130 switches the operation mode from the first operation mode MD1 to the second operation mode MD2. On the other hand, in the state of the second operation mode MD2, in a case where the imaging menu reception signal 121 is input from the reception unit 120, the mode switching unit 130 switches the operation mode from the second operation mode MD2 to the first operation mode MD1. In both aspects of FIGS. 43 and 44, an effect that the non-operation period of the breast imaging apparatus can be allotted to disinfection by the irradiation of the ultraviolet light UV is obtained.

The timing of switching the operation mode from the first operation mode MD1 to the second operation mode MD2 may be a case where there is no imaging order of the status "before imaging" in the order-specific irradiation condition information 67. Alternatively, the operation mode may be switched from the first operation mode MD1 to the second operation mode MD2 in a time period determined in advance by the operator OP, such as a lunch break, outside work hours of a medical facility. The operation mode may be switched from the first operation mode MD1 to the second operation mode MD2 at a predetermined set time or in a case where there is no operation on the apparatus body and the control device.

Second_5 Embodiment

Figure 45:
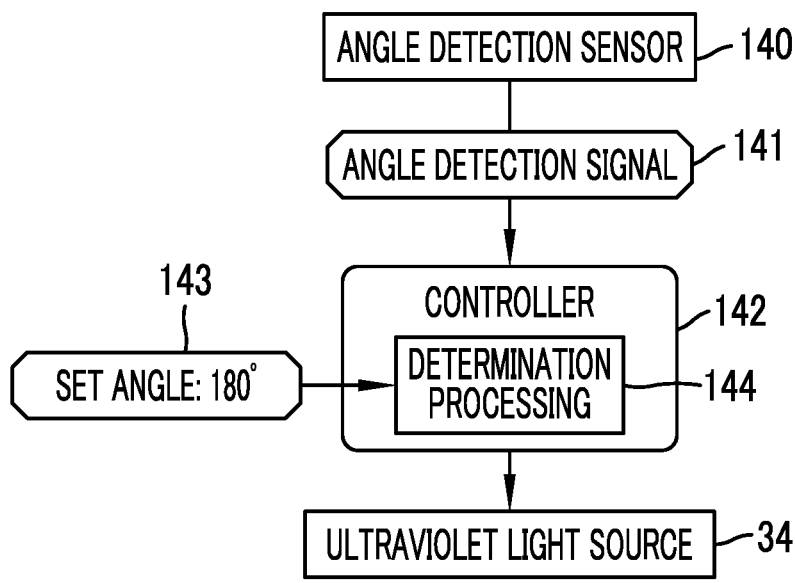
FIG. 45 is a diagram conceptually showing processing of a controller in a second_5 embodiment.
Figure 46:
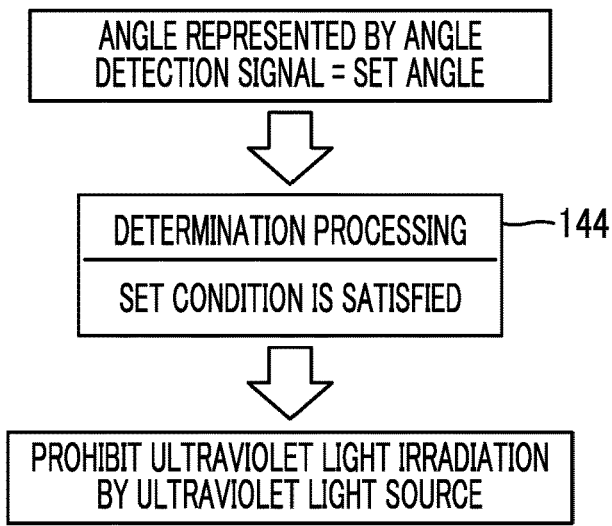
FIG. 46 is a diagram showing processing of the controller in a case where an angle represented by an angle detection signal is a set angle.

In a second_5 embodiment shown in FIGS. 45 and 46, in a case where the angle of the radiation source 25 and the radiation detector 26 with respect to the breast M is a predetermined set angle 143, determination is made that a set condition is satisfied. The second_5 embodiment supposes that the irradiation of the ultraviolet light UV is permitted regardless of whether or not there is a person, unlike the above-described second_1 to second_4 embodiments.

As an example, as shown in FIG. 45, a breast imaging apparatus of the second_5 embodiment comprises an angle detection sensor 140 that detects the angle of the radiation source 25 and the radiation detector 26 with respect to the breast M. The angle detection sensor 140 is attached to, for example, the body portion 24. The angle detection sensor 140 detects the angle to be 0° in CC_A imaging shown in FIG. 8, detects the angle to be 180° in CC_B imaging shown in FIG. 9, and detects the angle to be 60° to 90° in MLO imaging shown in FIG. 10. The angle detection sensor 140 outputs an angle detection signal 141 representing the detected angle to a controller 142. The controller 142 executes determination processing 144 regarding whether or not a set condition for prohibiting the irradiation of the ultraviolet light UV by the ultraviolet light source 34 is satisfied based on the angle detection signal 141 and the set angle 143. The controller 142 controls the operation of the ultraviolet light source 34 corresponding to a determination result of the determination processing 144. The set angle 143 is set to 180° that is the angle in CC_B imaging.

As an example, as shown in FIG. 46, in a case where the angle represented by the angle detection signal 141 from the angle detection sensor 140 is the set angle 143, the controller 142 determines that the set condition is satisfied. That is, the set condition in this case is that the angle of the radiation source 25 and the radiation detector 26 is the set angle. In this case, the controller 142 prohibits the irradiation of the ultraviolet light UV by the ultraviolet light source 34.

On the other hand, though not shown, in a case where the angle represented by the angle detection signal 141 from the angle detection sensor 140 is an angle (in the example, 0° or 60° to 90°) other than the set angle 143, the controller 142 determines that the set condition is not satisfied, and permits the irradiation of the ultraviolet light UV by the ultraviolet light source 34.

In a case where the angle is 180° set as the set angle 143, as shown in FIG. 9, the radiation source 25 and the irradiation field limiter 31 are positioned below the face of the subject H. In the middle of CC_B imaging with such a positional relationship, for example, in a case where the irradiation of the ultraviolet light UV is incorrectly performed from the ultraviolet light source 34 provided on the external surface of the irradiation field limiter 31 facing the pressing plate 33, the face of the subject H is irradiated with the ultraviolet light UV, and an influence is significant. In the second_5 embodiment, the angle detection sensor 140 that detects the angle of the radiation source 25 and the radiation detector 26 with respect to the breast M is provided. Then, the controller 142 determines that the set condition is satisfied in a case where the angle detected by the angle detection sensor 140 is the predetermined set angle 143. For this reason, it is possible to reliably prevent a situation in which the face of the subject H is incorrectly irradiated with the ultraviolet light UV, and the subject H receives a significant influence.

Figure 47:
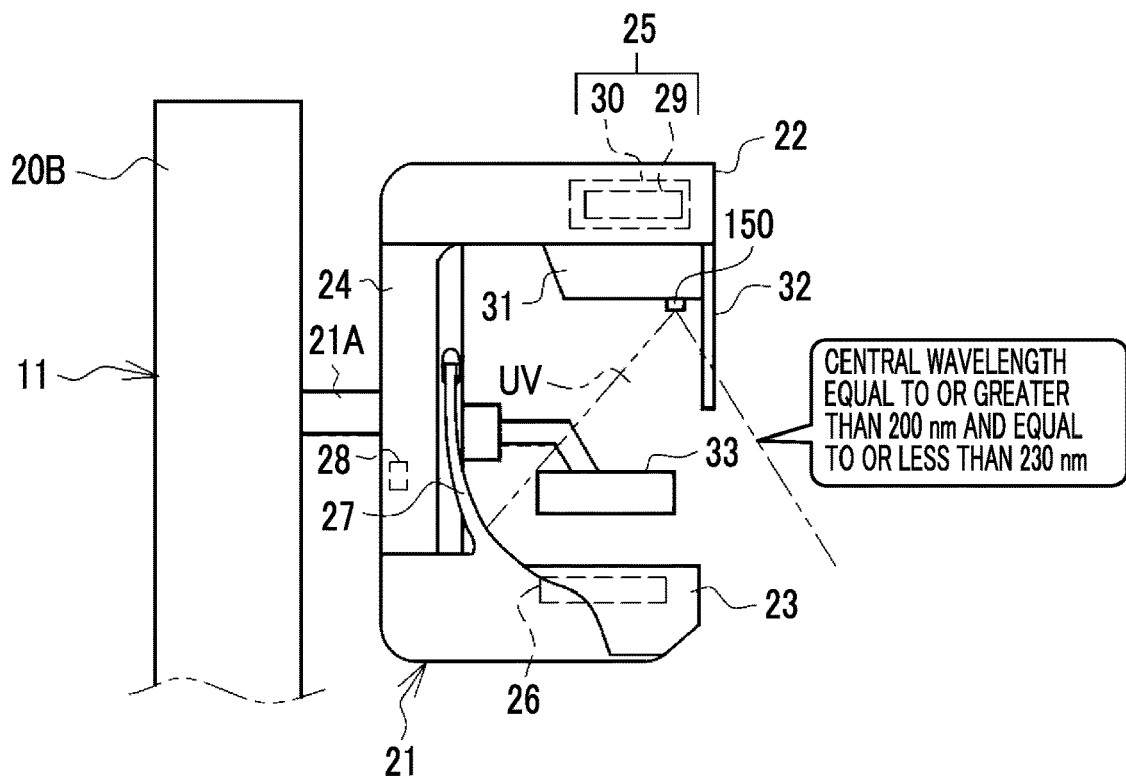
FIG. 47 is a diagram showing an example where an ultraviolet light source having a central wavelength equal to or greater than 200 nm and equal to or less than 230 nm is provided.

In the respective embodiments described above, although the ultraviolet light source 34 that emits the ultraviolet light UV having the central wavelength equal to or greater than 200 nm and equal to or less than 280 nm has been exemplified, the technique of the present disclosure is not limited thereto. As shown in FIG. 47, an ultraviolet light source 150 that emits ultraviolet light UV having a central wavelength equal to or greater than 200 nm and equal to or less than 230 nm may be used. The ultraviolet light UV having the central wavelength equal to or greater than 200 nm and equal to or less than 230 nm has little influence on a human body compared to ultraviolet light UV having the central wavelength greater than 230 nm and equal to or less than 280 nm. For this reason, even though the subject H or the like is incorrectly irradiated with the ultraviolet light, there is less influence.

Third Embodiment

In a third embodiment shown in FIGS. 48 to 58, a plurality of ultraviolet light sources that emit ultraviolet light UV of different wavelength ranges are used.

Third_1 Embodiment

Figure 48:
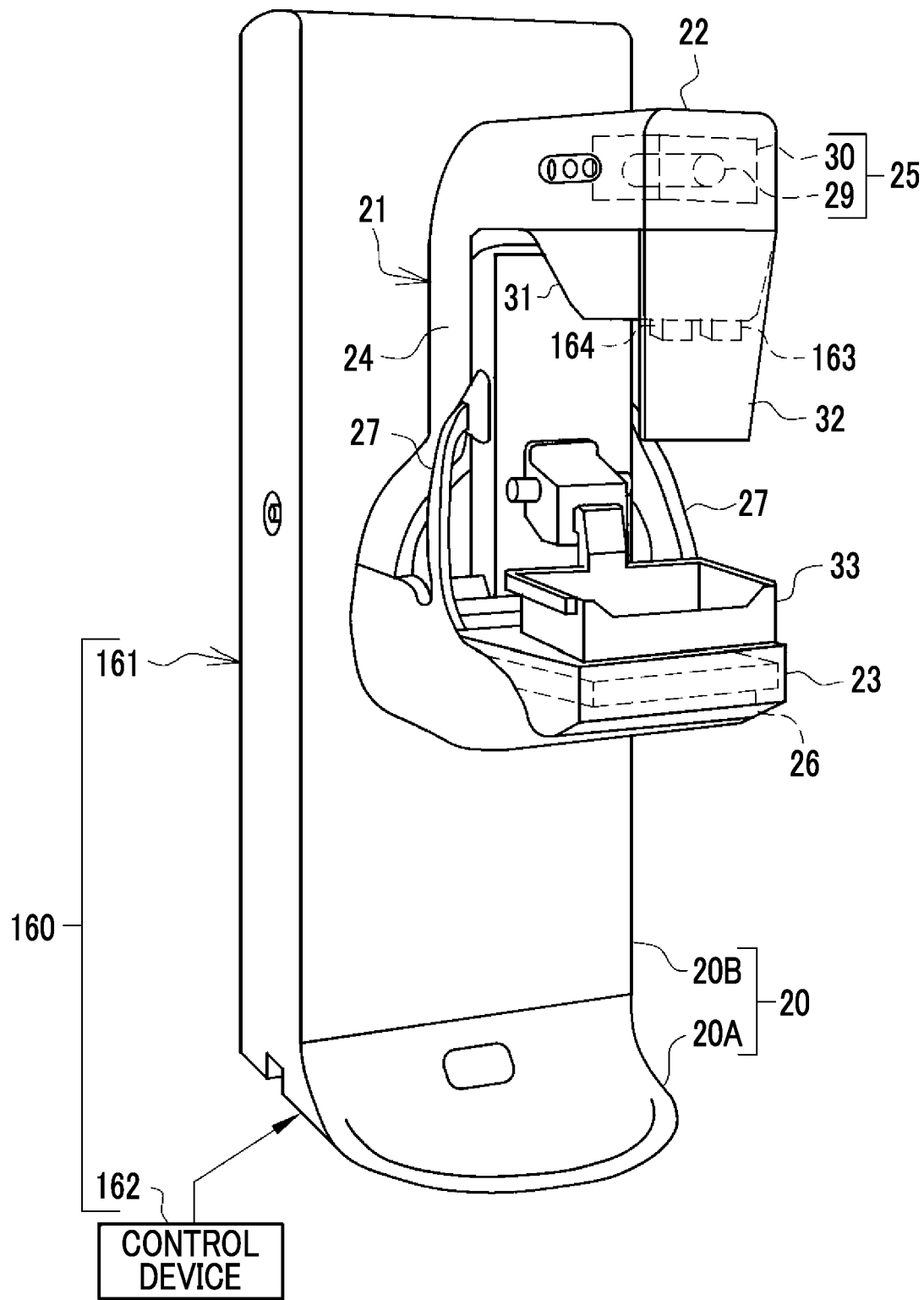
FIG. 48 is a diagram showing a breast imaging apparatus of a third_1 embodiment.

As an example, as shown in FIG. 48, a breast imaging apparatus 160 of a third_1 embodiment comprises an apparatus body 161 and a control device 162. The apparatus body 161 is different from the apparatus body 11 of the above-described first embodiment in that a first ultraviolet light source 163 and a second ultraviolet light source 164, instead of the ultraviolet light source 34, are provided alongside on the external surface of the irradiation field limiter 31 facing the pressing plate 33. Other configurations are the same as those of the apparatus body 11 and are thus represented by the same reference numerals, and description thereof will not be repeated.

Figure 49:
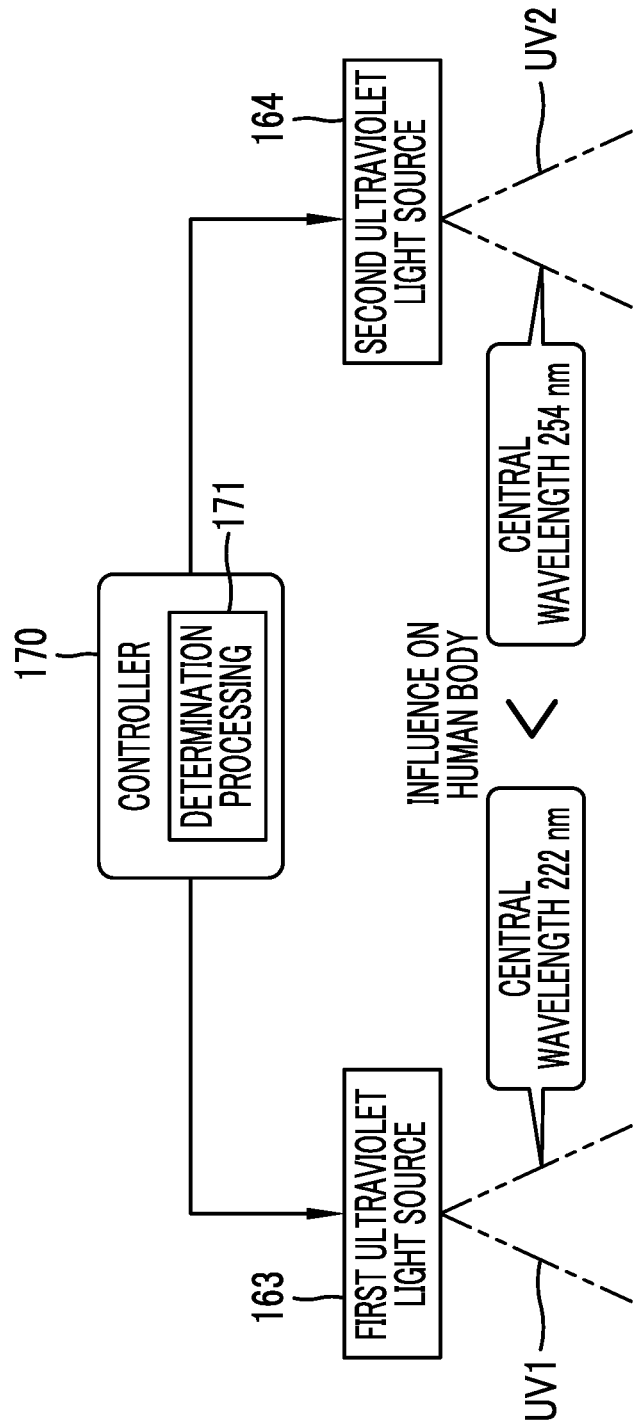
FIG. 49 is a diagram conceptually showing processing of a controller in the third_1 embodiment.

As an example, as shown in FIG. 49, the first ultraviolet light source 163 performs irradiation of first ultraviolet light UV1 having a central wavelength of 222 nm under the control of a controller 170 of the control device 162. In contrast, the second ultraviolet light source 164 performs irradiation of second ultraviolet light UV2 having a central wavelength of 254 nm under the control of the controller 170. The first ultraviolet light UV1 has little influence on a human body compared to the second ultraviolet light UV2. The first ultraviolet light UV1 may have a central wavelength of 207 nm. The fact that the first ultraviolet light UV1 having the central wavelength of 222 nm or the central wavelength of 207 nm has little influence on a human body compared to the second ultraviolet light UV2 having the central wavelength of 254 nm is described in, for example, the paragraphs [0028] to [0031] and FIGS. 7 and 8 of JP6306097B.

The controller 170 executes determination processing 171 regarding whether or not a set condition for prohibiting at least the irradiation of the second ultraviolet light UV2 by the second ultraviolet light source 164 is satisfied. The controller 170 controls the operation of the second ultraviolet light source 164 corresponding to a determination result of the determination processing 171.

Figure 50:
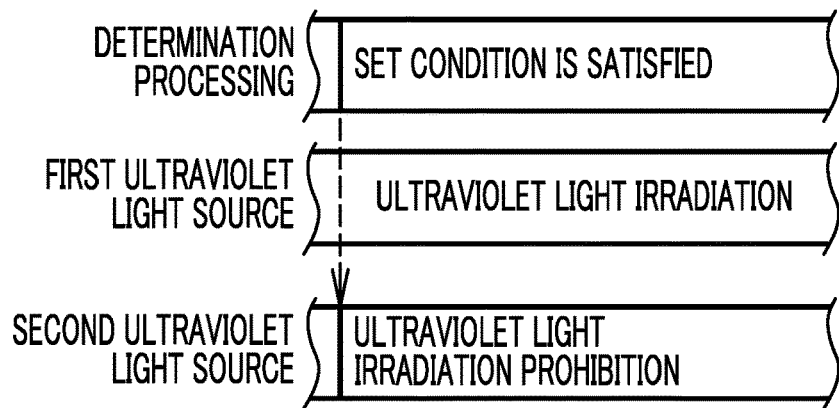
FIG. 50 is a diagram showing an example of operation control of a first ultraviolet light source and a second ultraviolet light source by a controller.
Figure 51:
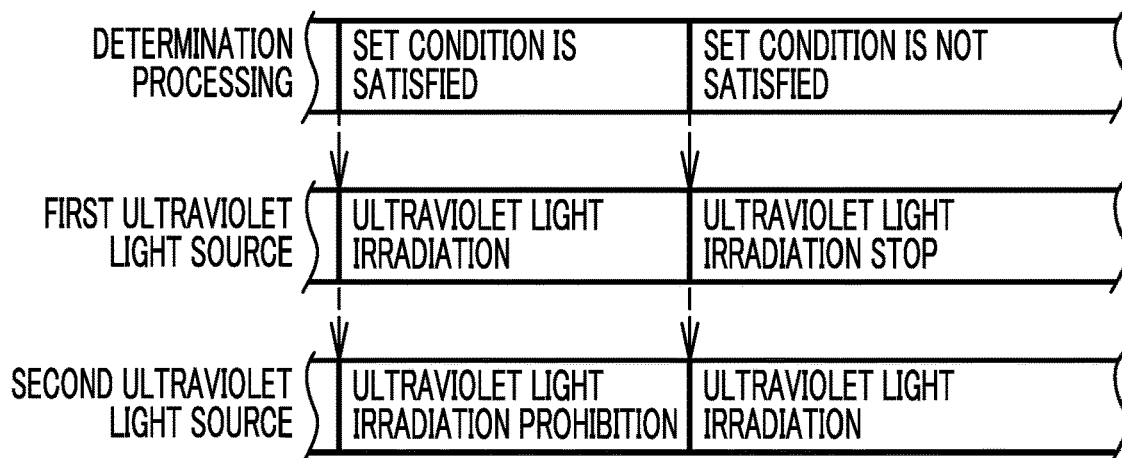
FIG. 51 is a diagram showing another example of operation control of the first ultraviolet light source and the second ultraviolet light source by the controller.
Figure 52:
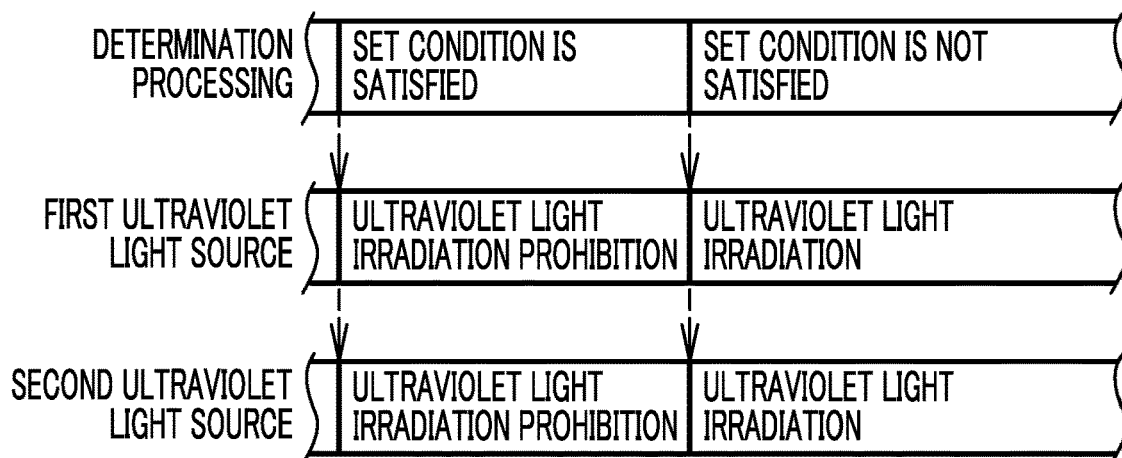
FIG. 52 is a diagram showing still another example of operation control of the first ultraviolet light source and the second ultraviolet light source by the controller.

FIGS. 50 to 52 show examples of operation control of the first ultraviolet light source 163 and the second ultraviolet light source 164 by the controller 170.

First, in the example of FIG. 50, the controller 170 makes the first ultraviolet light source 163 constantly perform the irradiation of the first ultraviolet light UV1. On the other hand, the controller 170 prohibits the irradiation of the second ultraviolet light UV2 by the second ultraviolet light source 164 in a case where determination is made in the determination processing 171 that the set condition is satisfied.

In the example of FIG. 51, in a case where determination is made in the determination processing 171 that the set condition is satisfied, the controller 170 makes the first ultraviolet light source 163 perform the irradiation of the first ultraviolet light UV1, and prohibits the irradiation of the second ultraviolet light UV2 by the second ultraviolet light source 164. In a case where determination is made in the determination processing 171 that the set condition is not satisfied, the controller 170 stops the irradiation of the first ultraviolet light UV1 by the first ultraviolet light source 163, and makes the second ultraviolet light source 164 perform the irradiation of the second ultraviolet light UV2. In the examples of FIGS. 50 and 51, the controller 170 makes an irradiation timing of the first ultraviolet light UV1 of the first ultraviolet light source 163 different from an irradiation timing of the second ultraviolet light UV2 of the second ultraviolet light source 164.

In the example of FIG. 52, in a case where determination is made in the determination processing 171 that the set condition is satisfied, the controller 170 prohibits the irradiation of the first ultraviolet light UV1 by the first ultraviolet light source 163, and prohibits the irradiation of the second ultraviolet light UV2 by the second ultraviolet light source 164. In a case where determination is made in the determination processing 171 that the set condition is not satisfied, the controller 170 makes the first ultraviolet light source 163 perform the irradiation of the first ultraviolet light UV1, and makes the second ultraviolet light source 164 perform the irradiation of the second ultraviolet light UV2. That is, the controller 170 makes the irradiation timing of the first ultraviolet light UV1 of the first ultraviolet light source 163 identical to the irradiation timing of the second ultraviolet light UV2 of the second ultraviolet light source 164.

The aspects of FIGS. 50 to 52 may be selectable by the operator OP. In the example of FIG. 50, instead of making the first ultraviolet light source 163 constantly perform the irradiation of the first ultraviolet light UV1, the irradiation of the first ultraviolet light UV1 may be stopped at a predetermined timing. For example, the irradiation and the irradiation stop of the first ultraviolet light UV1 are repeated at predetermined intervals. The irradiation of the first ultraviolet light UV1 may be performed during imaging of the radiographic image RI, and the irradiation of the first ultraviolet light UV1 may be stopped after imaging of the radiographic image RI ends. Then, it is possible to reduce power consumption compared to constant irradiation, and to suppress deterioration of a resin material due to the irradiation of the first ultraviolet light UV1.

As shown in FIGS. 48 and 49, the breast imaging apparatus 160 comprises the first ultraviolet light source 163 and the second ultraviolet light source 164 that emit the first ultraviolet light UV1 and the second ultraviolet light UV2 of different wavelength ranges. For this reason, as shown in FIGS. 50 to 52, disinfection can be performed with various variations.

As shown in FIG. 49, a plurality of ultraviolet light sources include the first ultraviolet light source 163 that emits the first ultraviolet light UV1 having a relatively small influence on the human body, and the second ultraviolet light source 164 that emits the second ultraviolet light UV2 having a relatively large influence on the human body. For this reason, as shown in FIGS. 50 and 51, it is possible to perform more thorough disinfection by positively performing the irradiation of the first ultraviolet light UV1 having a relatively small influence on the human body.

As shown in FIGS. 50 and 51, the controller 170 makes the irradiation timing of the first ultraviolet light UV1 of the first ultraviolet light source 163 different from the irradiation timing of the second ultraviolet light UV2 of the second ultraviolet light source 164. For this reason, it is possible to perform disinfection utilizing the respective characteristics of the first ultraviolet light UV1 and the second ultraviolet light UV2.

As shown in FIGS. 50 to 52, in a case where the predetermined set condition is satisfied, the controller 170 prohibits the irradiation of the second ultraviolet light UV2 by the second ultraviolet light source 164. For this reason, it is possible to reduce a concern that a human body is irradiated with the second ultraviolet light UV2. In the example of FIG. 52, it is also possible to reduce a concern that a human body is irradiated with the first ultraviolet light UV1, as well as the second ultraviolet light UV2.

Third_2 Embodiment

Figure 53:
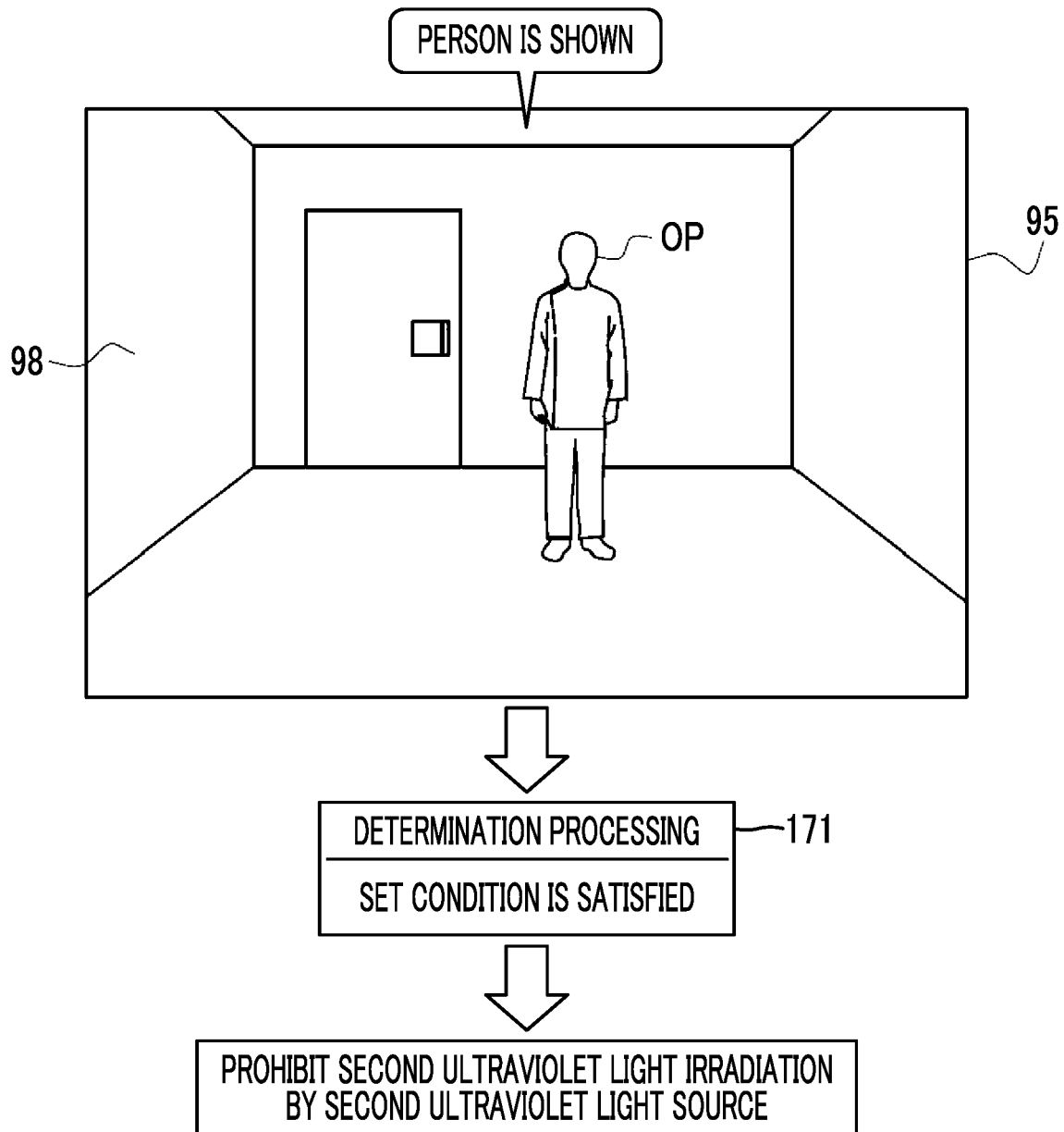
FIG. 53 is a diagram showing processing of the controller in a case where a person is shown in the captured image of the camera.
Figure 54:
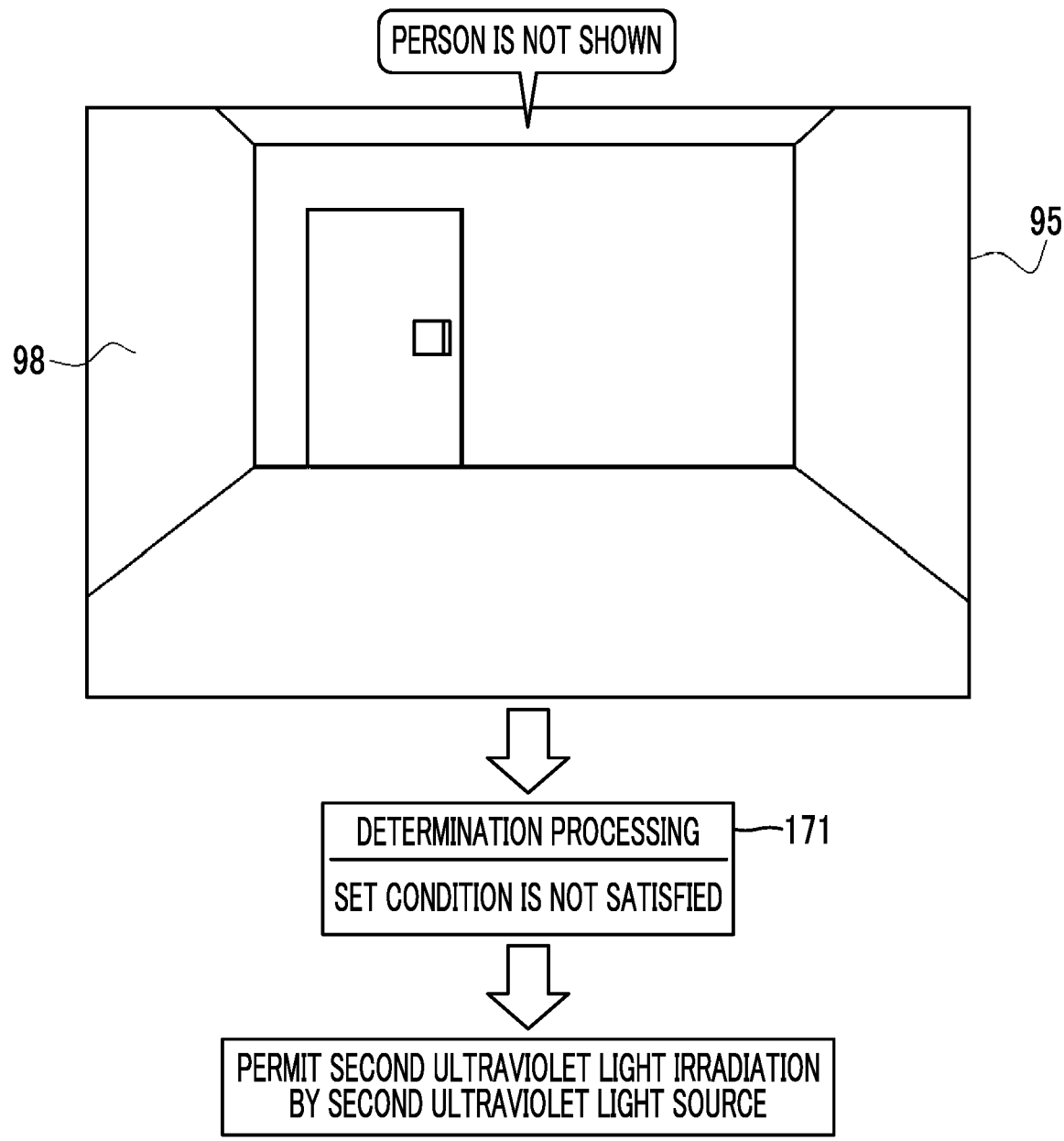
FIG. 54 is a diagram showing processing of the controller in a case where a person is not shown in the captured image of the camera.

In a third_2 embodiment shown in FIGS. 53 and 54, as in the above-described second_1 embodiment, the controller 170 executes the determination processing 171 based on the captured image 95 of the camera 93.

As an example, as shown in FIG. 53, in a case where a person, such as the operator OP, is shown in captured image 95, the controller 170 determines that the set condition is satisfied. The controller 170 determines that the set condition is satisfied, for example, while a person is shown in the captured image 95. That is, the set condition in this case is that a person is shown in the captured image 95. In this case, the controller 170 prohibits the irradiation of the second ultraviolet light UV2 by the second ultraviolet light source 164.

In contrast, as an example, as shown in FIG. 54, in a case where a person, such as the operator OP, is not shown in the captured image 95, the controller 170 determines that the set condition is not satisfied. In this case, the controller 170 permits the irradiation of the second ultraviolet light UV2 by the second ultraviolet light source 164.

In this way, the controller 170 determines that the set condition is satisfied in a case where a person is shown in the captured image 95 of the camera 93. For this reason, it is possible to further reduce a concern that a human body is irradiated with the second ultraviolet light UV2.

Third_3 Embodiment

Figure 55:
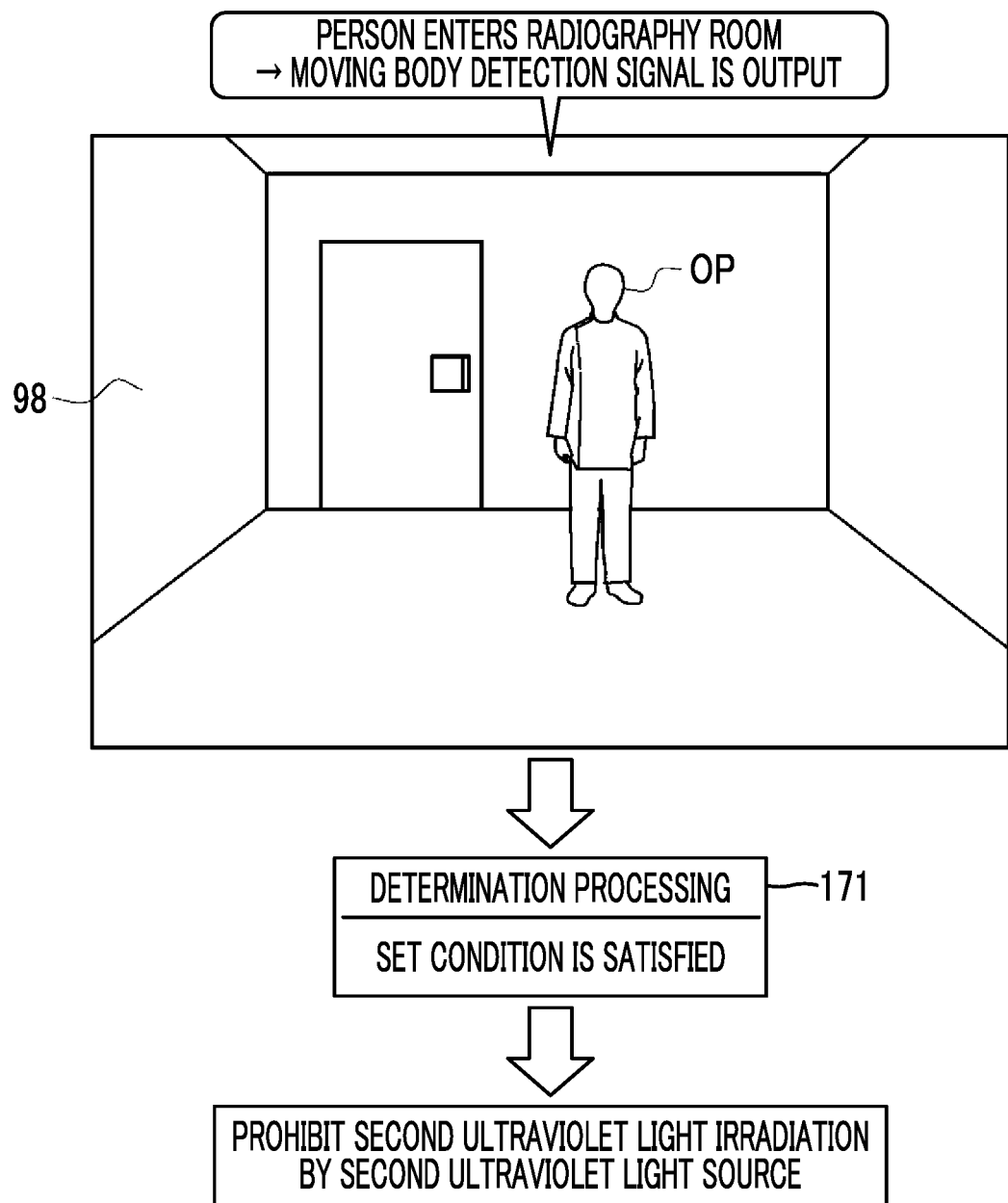
FIG. 55 is a diagram showing processing of the controller in a case where the moving body detection signal is output from the moving body detection sensor.
Figure 56:
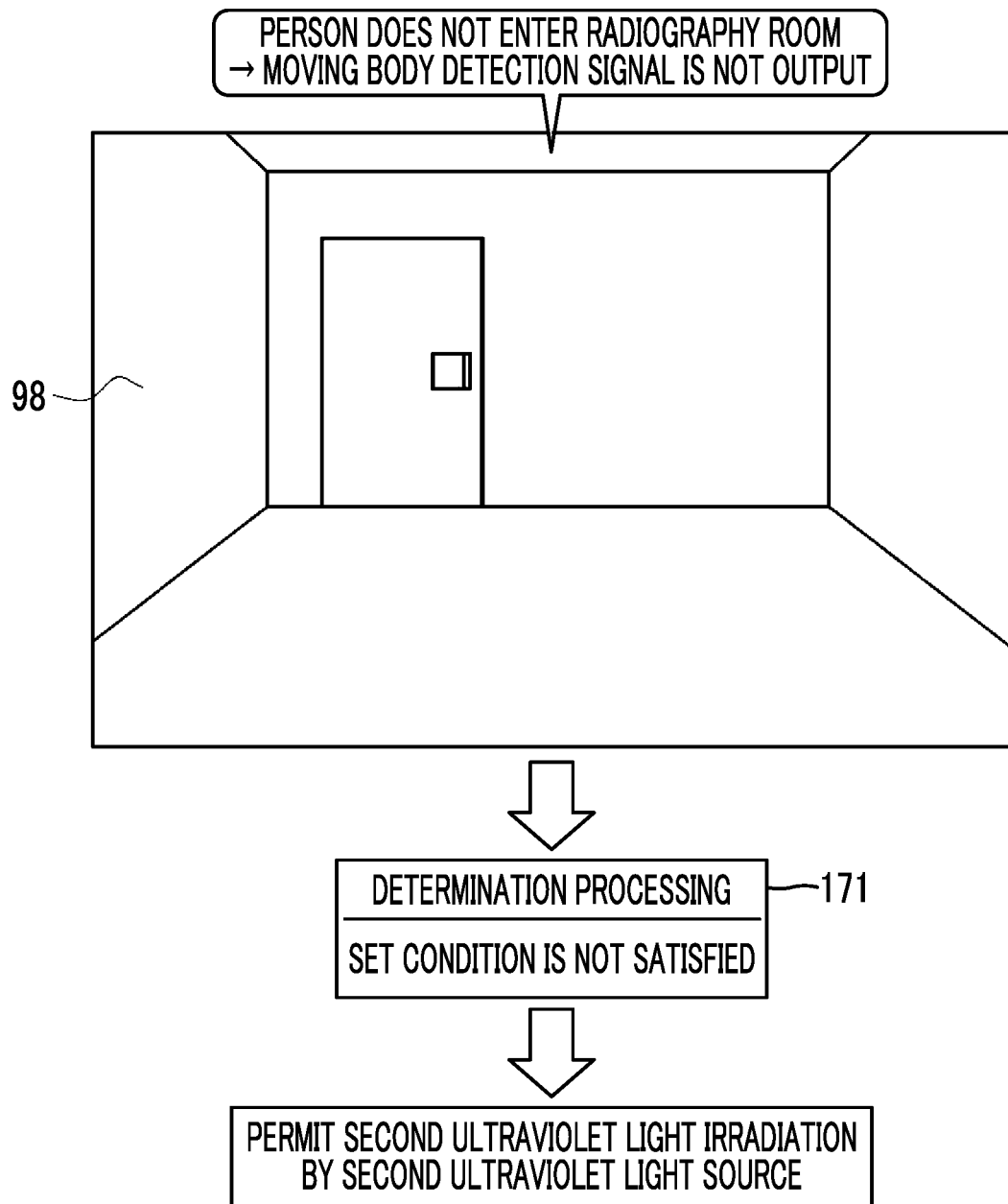
FIG. 56 is a diagram showing processing of the controller in a case where the moving body detection signal is not output from the moving body detection sensor.

In a third_3 embodiment shown in FIGS. 55 and 56, as in the above-described second_2 embodiment, the controller 170 executes the determination processing 171 based on the moving body detection signal 110.

As an example, as shown in FIG. 55, in a case where a person, such as the operator OP, enters the radiography room 98, and the moving body detection signal 110 is output from the moving body detection sensor 108, the controller 170 determines that the set condition is satisfied. The controller 170 determines that the set condition is satisfied, for example, until the set period elapses after the moving body detection signal 110 is received. That is, the set condition in this case is that the moving body detection sensor 108 detects a moving body. In this case, the controller 170 prohibits the irradiation of the second ultraviolet light UV2 by the second ultraviolet light source 164.

In contrast, as an example, as shown in FIG. 56, in a case where a person, such as the operator OP, does not enter the radiography room 98, and the moving body detection signal 110 is not output from the moving body detection sensor 108, the controller 170 determines that the set condition is not satisfied. In this case, the controller 170 permits the irradiation of the second ultraviolet light UV2 by the second ultraviolet light source 164.

In this way, the controller 170 determines that the set condition is satisfied in a case where the moving body detection sensor 108 detects a moving body. For this reason, it is possible to further reduce a concern that a human body is irradiated with the second ultraviolet light UV2. The moving body detection sensor 108 is inexpensive compared to the camera 93 of the above-described third_2 embodiment, and does not need to analyze the captured image 95 to detect whether or not a person is shown.

Third_4 Embodiment

Figure 57:
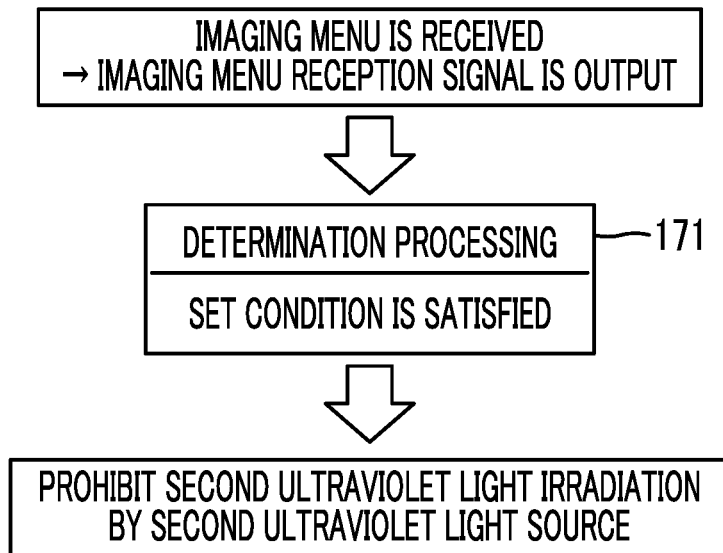
FIG. 57 is a diagram showing processing of the controller in a case where the imaging menu reception signal is output from the reception unit.
Figure 58:
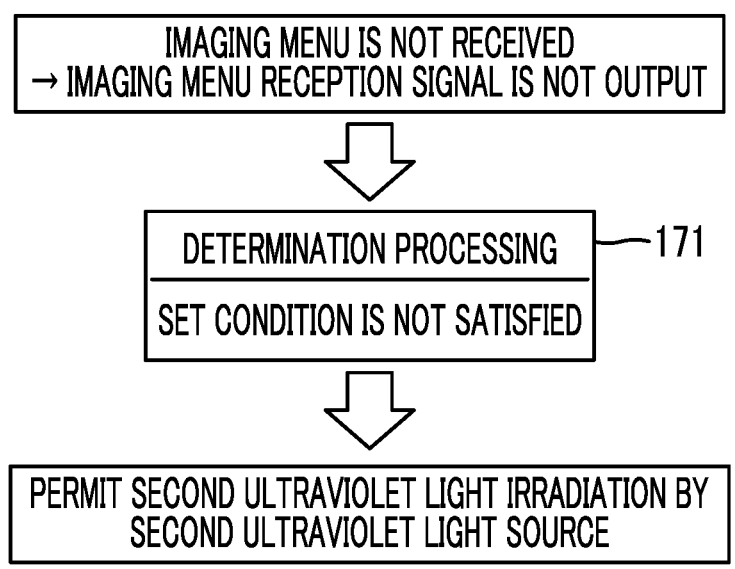
FIG. 58 is a diagram showing processing of the controller in a case where the imaging menu reception signal is not output from the reception unit.

In a third_4 embodiment shown in FIGS. 57 and 58, as in the above-described second_3 embodiment, the controller 170 executes the determination processing 171 based on the imaging menu reception signal 121 from the reception unit 120.

As an example, as shown in FIG. 57, in a case where the imaging menu 80 is input by the operator OP through the input device 59, the imaging menu 80 is received in the reception unit 120, and the imaging menu reception signal 121 is output from the reception unit 120, the controller 170 determines that the set condition is satisfied. The controller 170 determines that the set condition is satisfied, for example, until the set period elapses after the imaging menu reception signal 121 is received. That is, the set condition in this case is that the reception unit 120 receives the imaging menu 80. In this case, the controller 170 prohibits the irradiation of the second ultraviolet light UV2 by the second ultraviolet light source 164.

In contrast, as an example, as shown in FIG. 58, in a case where the imaging menu 80 is not received in the reception unit 120, and the imaging menu reception signal 121 is not output from the reception unit 120, the controller 170 determines that the set condition is not satisfied. In this case, the controller 170 permits the irradiation of the second ultraviolet light UV2 by the second ultraviolet light source 164.

In this way, the controller 170 determines that the set condition is satisfied in a case where the reception unit 120 receives the imaging menu 80. Soon after the reception unit 120 receives the imaging menu 80, the subject H enters the radiography room 98, and imaging of the radiographic image RI is performed. For this reason, it is possible to further reduce a concern that a human body is irradiated with the second ultraviolet light UV2. There is no need to provide the camera 93 of the above-described third_2 embodiment and the moving body detection sensor 108 of the above-described third_3 embodiment.

As in the above-described second_1 embodiment, the above-described second_2 embodiment, and the above-described second_3 embodiment, the above-described third_2 embodiment and the third_4 embodiment or the above-described third_3 embodiment and the third_4 embodiment may be embodied in combination.

Contrary to the above description, in a case where the reception unit 120 receives the imaging menu 80, the controller 170 may determine that the set condition is not satisfied, and may permit the irradiation of the second ultraviolet light UV2 by the second ultraviolet light source 164.

In a case where the above-described second_4 embodiment is applied, and the mode switching unit 130 switches the operation mode to the second operation mode MD2, the controller 170 may determine that the set condition is not satisfied, and may permit the irradiation of the second ultraviolet light UV2 by the second ultraviolet light source 164.

In a case where the second_5 embodiment is applied, and the angle of the radiation source 25 and the radiation detector 26 with respect to the breast M is the predetermined set angle 143, the controller 170 may determine that the set condition is satisfied, and may prohibit the irradiation of the second ultraviolet light UV2 by the second ultraviolet light source 164.

Though not shown, in the third embodiment, as in the aspect shown in FIG. 26, in a case of making the second ultraviolet light source 164 perform the irradiation of the second ultraviolet light UV2, the controller 170 makes the second ultraviolet light source 164 continue the irradiation of the second ultraviolet light UV2 for the predetermined first set period P1.

As in the aspect shown in FIG. 27, the controller 170 makes the second ultraviolet light source 164 interrupt the irradiation of the second ultraviolet light UV2 in a case where determination is made that the set condition is satisfied before the first set period P1 elapses. The display controller displays the warning window 101 on the display 58.

As in the aspect shown in FIG. 31, the controller 170 makes the second ultraviolet light source 164 restart the irradiation of the second ultraviolet light UV2 in a case where determination is made that the set condition is not satisfied within the predetermined second set period P2 after the irradiation of the second ultraviolet light UV2 is interrupted.

The first ultraviolet light source 163 and the second ultraviolet light source 164 may be provided inside the irradiation field limiter 31 instead of or in addition to the external surface of the irradiation field limiter 31. A plurality of ultraviolet light sources that emit ultraviolet light of different wavelength ranges are not limited to the first ultraviolet light source 163 and the second ultraviolet light source 164. In addition to the first ultraviolet light source 163 and the second ultraviolet light source 164, a third ultraviolet light source that emits third ultraviolet light of a wavelength range different from the first ultraviolet light UV1 and the second ultraviolet light UV2 may be provided.

As the set condition, other than the set condition exemplified above, a condition that the imaging table 23 is operated to be moved up and down, a condition that any operation, not limited to the input of the imaging menu 80, on the input device 59 of the control device is performed, or the like may be applied. For example, medical service hours of a medical facility may be applied as a set condition, and the irradiation of the ultraviolet light UV may be permitted in a time period other than the medical service hours.

In the breast imaging apparatus, a fan that supplies cooling air to a heat generating portion, such as the radiation tube 29, is constantly operated. A chamber having an ultraviolet light source near an exhaust port of cooling air of such a fan may be provided, and the breast imaging apparatus may be operated as an air cleaner.

Figure 59:
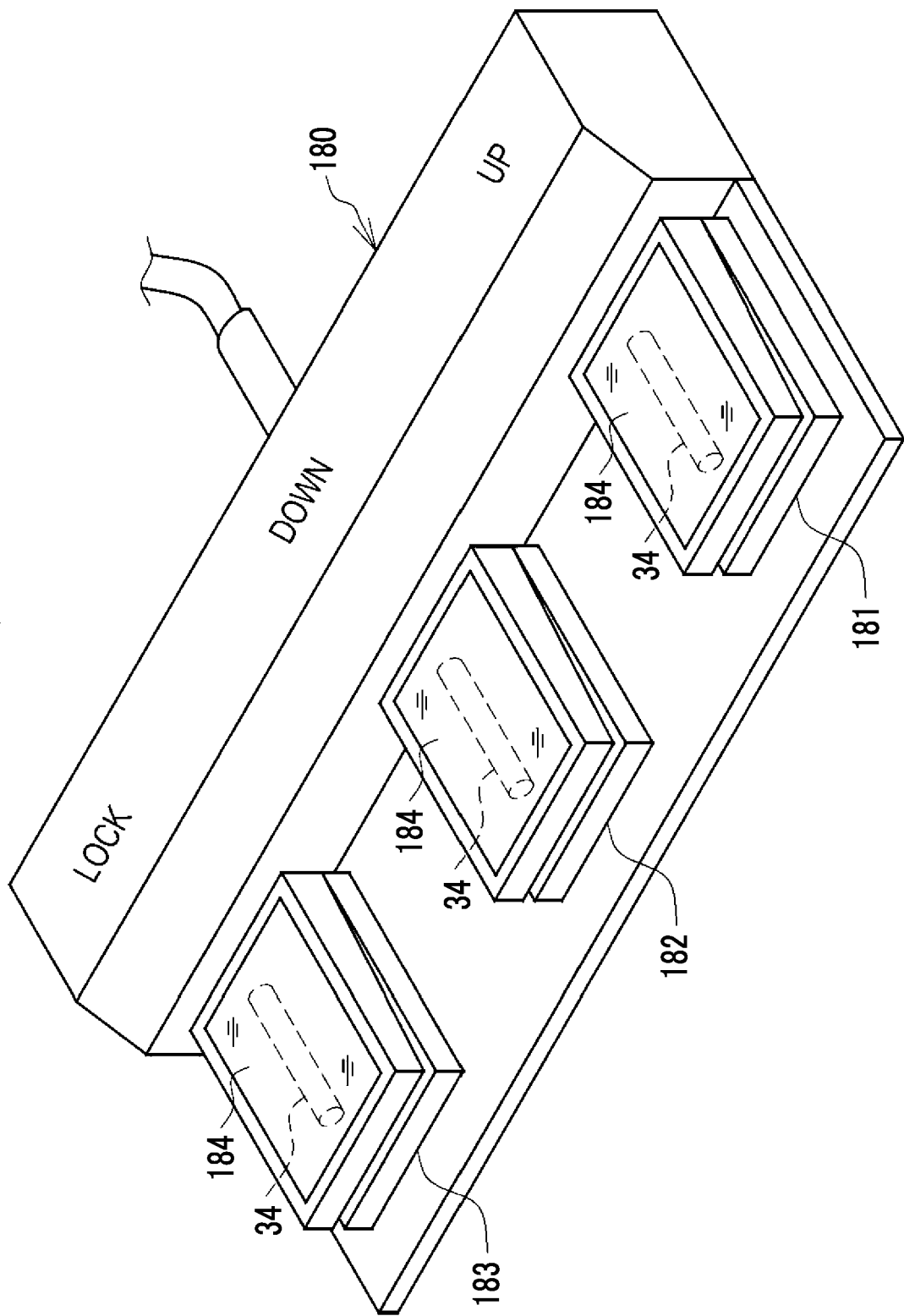
FIG. 59 is a diagram showing an aspect in which ultraviolet light sources are provided in foot-operating portions of a foot switch.

As a switch that moves the arm 21 in the height direction with respect to the column 20B and/or a switch that move the pressing plate 33 in the direction toward the imaging table 23 and the direction apart from the imaging table 23, a foot switch 180 shown in FIG. 59 may be used. The foot switch 180 has three foot-operating portions 181, 182, and 183 that are stepped on by the operator OP with the foot and are horizontally arranged in line. The foot-operating portion 181 is operated in a case of moving up the arm 21 or the pressing plate 33. The foot-operating portion 182 is operated in a case of moving down the arm 21 or the pressing plate 33. The foot-operating portion 183 is operated in a case of locking the position of the arm 21 or the pressing plate 33.

Each of the foot-operating portions 181 to 183 incorporates the ultraviolet light source 34. Then, a transmission window 184 is provided on a surface of each of the foot-operating portions 181 to 183 that are stepped on by the operator OP with the foot. The transmission window 184 is formed of a material transmitting the ultraviolet light UV similarly to the face guard 32 and the pressing plate 33. The irradiation of the ultraviolet light UV emitted from the ultraviolet light source 34 is performed toward a rear side of a shoe of the operator OP placed on each of the foot-operating portions 181 to 183 through the transmission window 184.

Figure 60:
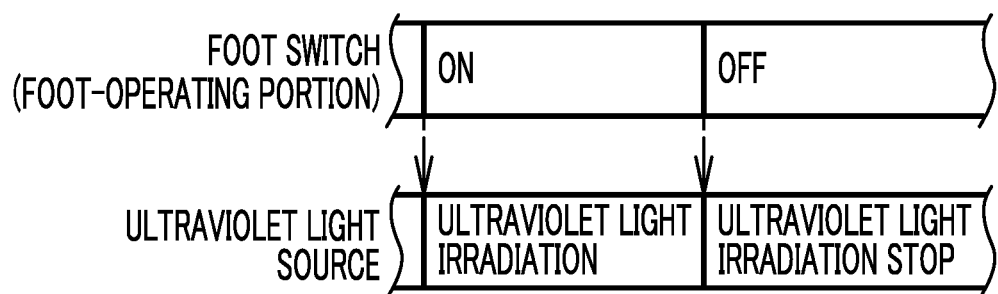
FIG. 60 is a diagram showing an example of operation control of the ultraviolet light sources provided in the foot switch.

As an example, as shown in FIG. 60, the ultraviolet light source 34 performs the irradiation of the ultraviolet light UV in a case where the foot-operating portions 181 to 183 are stepped on with the foot of the operator OP and turned on. On the contrary, the ultraviolet light source 34 stops the irradiation of the ultraviolet light UV in a case where the foot of the operator OP is released from the foot-operating portions 181 to 183 and the foot-operating portions 181 to 183 are turned off.

In this case, in a case where the ultraviolet light sources 34 are provided at places where the foot switches 180 are irradiated with the ultraviolet light UV, it is possible to effectively disinfect the shoe of the operator OP contaminated on the floor. In particular, in a case where the ultraviolet light sources 34 are provided in the foot-operating portions 181 to 183, it is possible to directly disinfect the rear side of the shoe of the operator OP on the floor.

Figure 61:
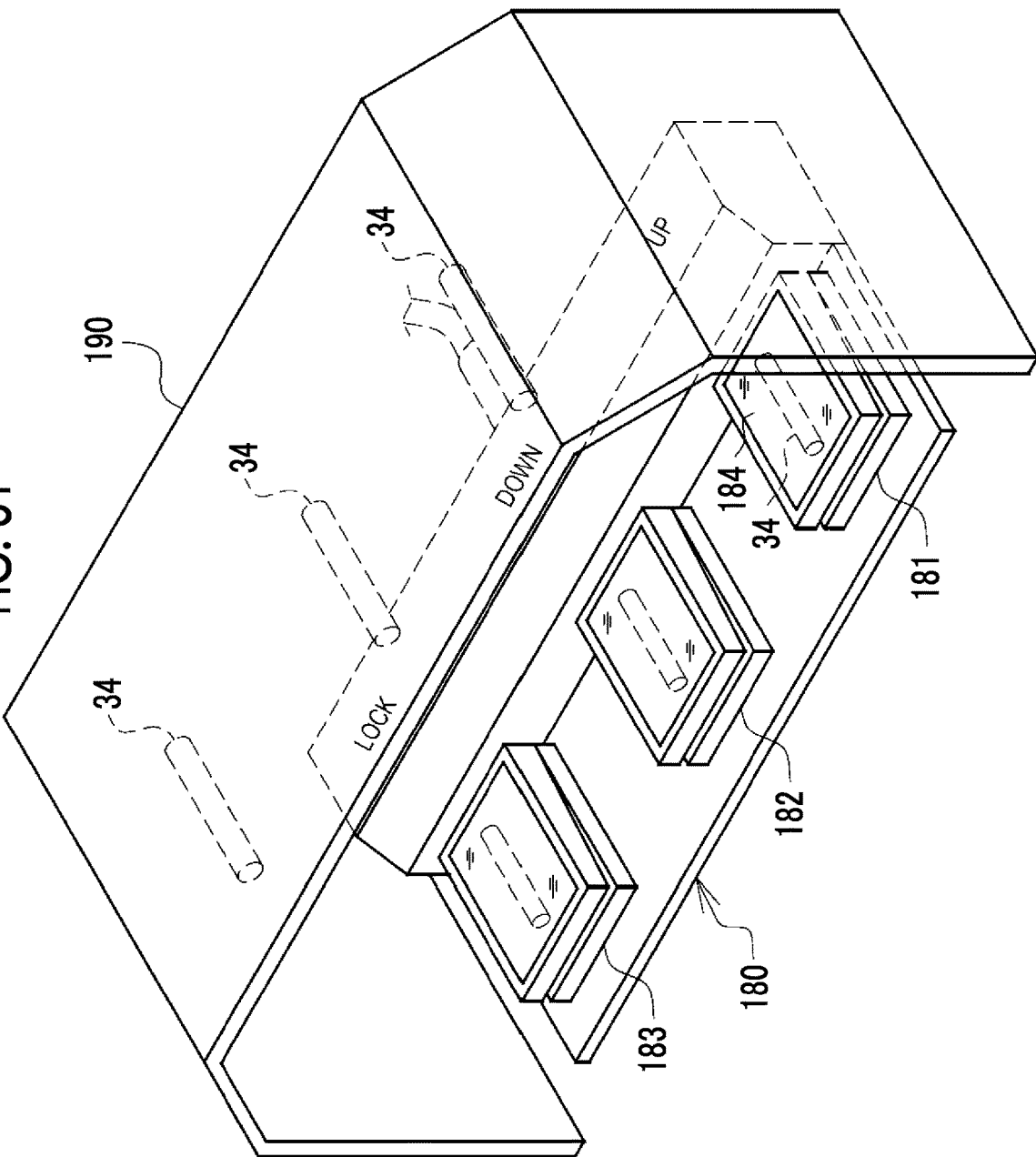
FIG. 61 is a diagram showing an aspect in which ultraviolet light sources are provided in the foot-operating portions of the foot switch and a cover.

The places where the ultraviolet light sources 34 are provided are not limited to the foot-operating portions 181 to 183. As an example, as shown in FIG. 61, the ultraviolet light sources 34 may be provided inside a cover 190 that covers the foot switch 180 from above. In more detail, the ultraviolet light sources 34 are attached to an internal surface of a top plate of the cover 190 confronting the foot switch 180. Similarly to the ultraviolet light sources 34 incorporated in the foot-operating portions 181 to 183, the ultraviolet light sources 34 provided in the cover 190 perform the irradiation of the ultraviolet light UV in a case where the foot-operating portions 181 to 183 are stepped on with the foot of the operator OP and turned on, and stop the irradiation of the ultraviolet light UV in a case where the foot of the operator OP is released from the foot-operating portions 181 to 183 and the foot-operating portions 181 to 183 are turned off. Then, it is possible to disinfect the front side of the shoe of the operator OP.

The ultraviolet light sources 34 provided in the cover 190 may constantly perform the irradiation of the ultraviolet light UV. The ultraviolet light sources 34 may be provided in at least one of the foot-operating portions 181 to 183 or the cover 190. The ultraviolet light source 150 may be used instead of the ultraviolet light source 34.

Fourth Embodiment

Figure 62:
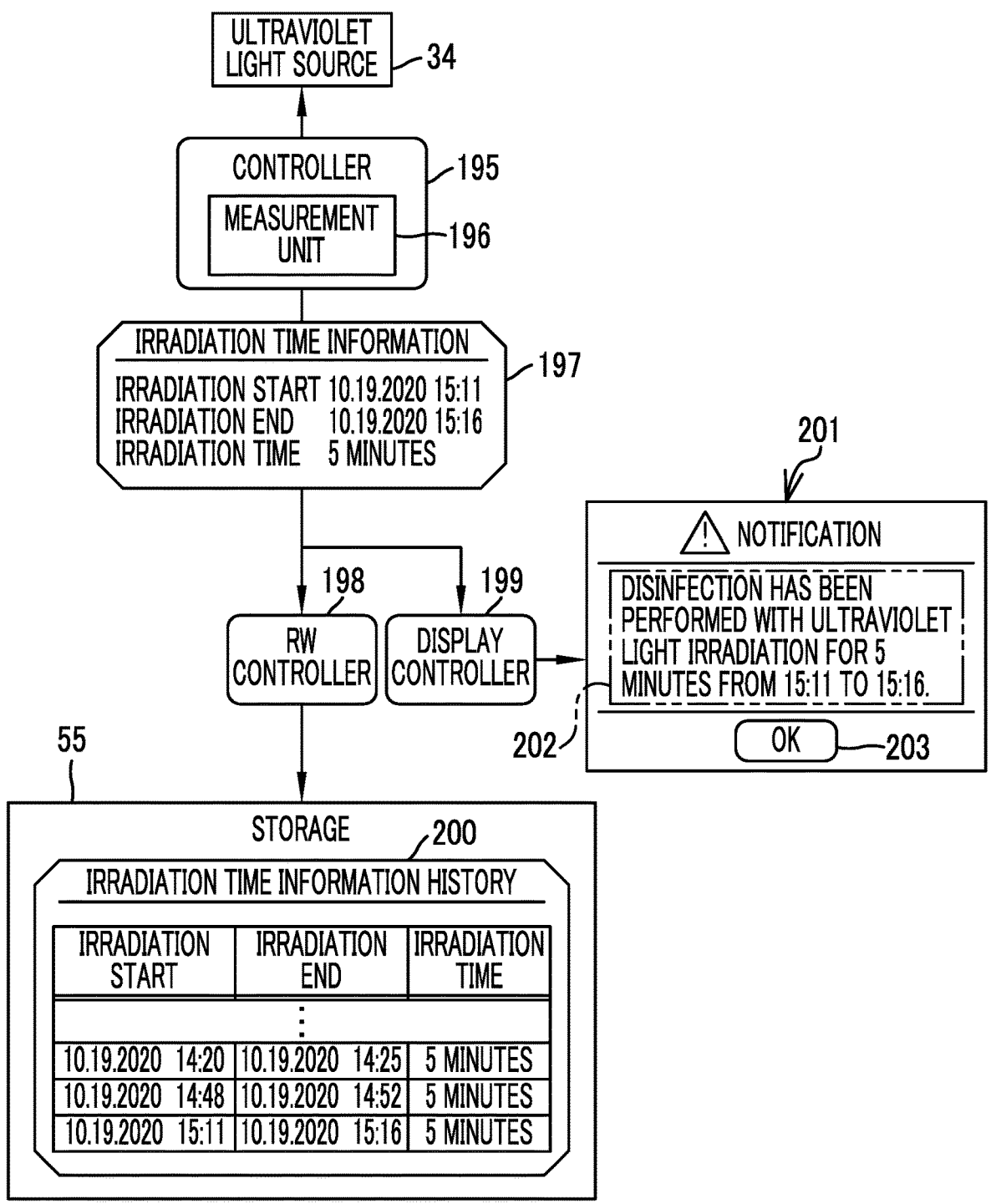
FIG. 62 is a diagram showing processing of measuring and storing an irradiation time of ultraviolet light.
Figure 63:
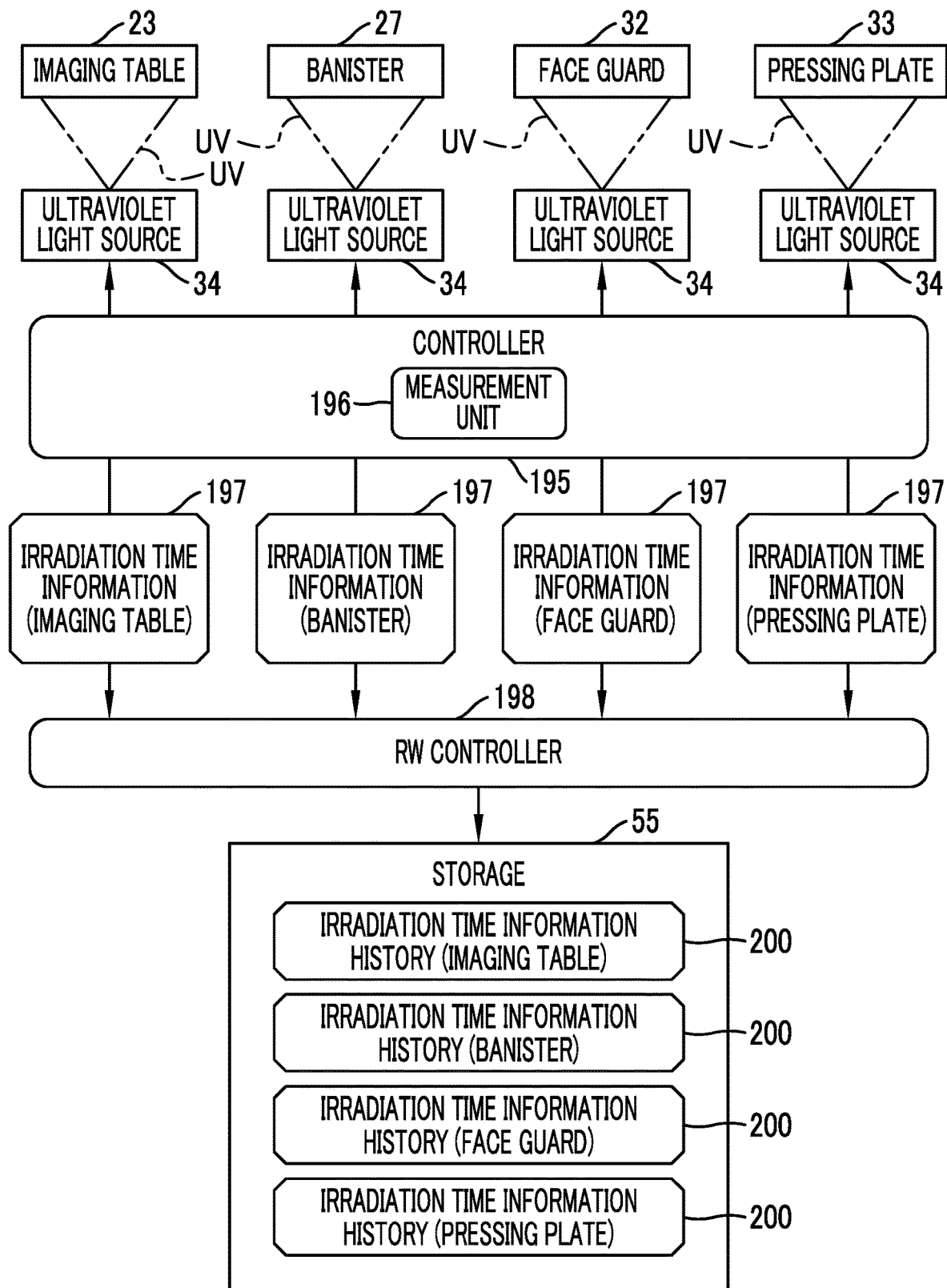
FIG. 63 is a diagram showing processing of measuring and storing an irradiation time of ultraviolet light of each of a plurality of places.
Figure 64:
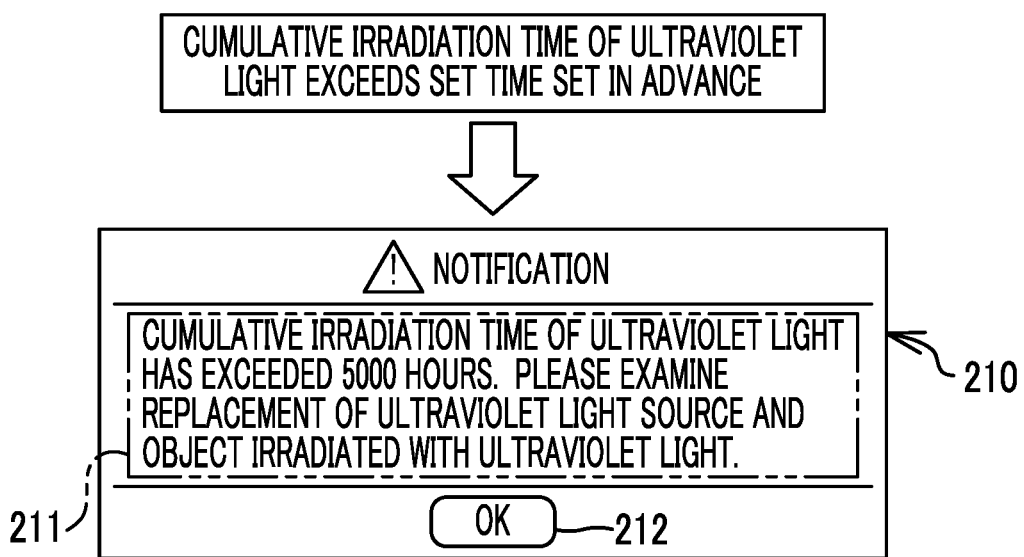
FIG. 64 is a diagram showing a notification window for notifying that a cumulative irradiation time of ultraviolet light exceeds a set time.

In a fourth embodiment shown in FIGS. 62 to 64, an irradiation time of the ultraviolet light UV is measured and the measured irradiation time is stored.

As an example, as shown in FIG. 62, a controller 195 of the fourth embodiment has a measurement unit 196. The measurement unit 196 measures the irradiation time of the ultraviolet light UV by the ultraviolet light source 34. In more detail, the measurement unit 196 stores irradiation start date and time on which the ultraviolet light source 34 starts the irradiation of the ultraviolet light UV and irradiation end date and time on which the ultraviolet light source 34 ends the irradiation of the ultraviolet light UV. Then, the measurement unit 196 obtains the irradiation time of the ultraviolet light UV from the irradiation start date and time and the irradiation end date and time. The controller 195 outputs irradiation time information 197 including the irradiation start date and time, the irradiation end date and time, and the irradiation time to an RW controller 198 and a display controller 199.

An irradiation time information history 200 is stored in the storage 55. The RW controller 198 registers the irradiation time information 197 from the controller 195 in the irradiation time information history 200. That is, the RW controller 198 stores the irradiation time of the ultraviolet light UV measured by the measurement unit 196 in the storage 55. That is, the storage 55 is an example of a "storage unit" according to the technique of the present disclosure, and the RW controller 198 is an example of a "storage controller" according to the technique of the present disclosure.

The display controller 199 displays a notification window 201 on the display 58. The notification window 201 includes a message 202 for notifying the irradiation time of the ultraviolet light UV by changing the irradiation time information 197 into a sentence. That is, the display controller 199 is an example of a second notification controller according to the technique of the present disclosure. The display of the notification window 201 is erased with selection of an OK button 203. The irradiation time of the ultraviolet light UV may be notified by playing a voice message for notifying the irradiation time of the ultraviolet light UV, or the like. In this case, a voice controller that controls the play of the voice message operates as the second notification controller.

In this way, in the fourth embodiment, the measurement unit 196 that measures the irradiation time of the ultraviolet light UV by the ultraviolet light source 34 is provided, and the RW controller 198 stores the irradiation time measured by the measurement unit 196 in the storage 55. For this reason, it is possible to manage the irradiation time of the ultraviolet light UV. It is also possible to appropriately perform the maintenance of an object irradiated with ultraviolet light that is irradiated with the ultraviolet light UV, such as the ultraviolet light source 34 and/or the pressing plate 33.

The display controller 199 notifies of the irradiation time of the ultraviolet light UV through the notification window 201. For this reason, it is possible to notify the operator OP of the irradiation time of the ultraviolet light UV. The operator OP can know that the irradiation of the ultraviolet light UV is performed for the irradiation time and disinfection is performed. The operator OP can also ascertain whether or not disinfection by the ultraviolet light UV is appropriately performed.

Although FIG. 62 illustrates a case where the number of ultraviolet light sources 34 is one, and the number of places irradiated with the ultraviolet light UV is one, the technique of the present disclosure is not limited thereto. As shown in FIG. 21, there may be a case where a plurality of ultraviolet light sources 34 are provided, and a plurality of places are irradiated with the ultraviolet light UV. In this case, as an example, as shown in FIG. 63, the measurement unit 196 measures the irradiation time of the ultraviolet light UV for each of a plurality of places. The RW controller 198 stores the irradiation time of the ultraviolet light UV of each of a plurality of places measured by the measurement unit 196 for each of a plurality of places, in the storage 55. Specifically, the RW controller 198 registers the irradiation time information 197 of each of a plurality of places in the irradiation time information history 200 prepared in the storage 55 for each of a plurality of places. FIG. 63 illustrates a case where four ultraviolet light sources 34 are provided, and the four ultraviolet light sources 34 perform the irradiation of the ultraviolet light UV toward the imaging table 23, the banisters 27, the face guard 32, and the pressing plate 33, respectively.

In this way, in a case where there are a plurality of places that are irradiated with the ultraviolet light UV, the measurement unit 196 measures the irradiation time of the ultraviolet light UV for each of a plurality of places. The RW controller 198 stores the irradiation time of the ultraviolet light UV of each of a plurality of places measured by the measurement unit 196 for each of a plurality of places. For this reason, it is possible to individually manage the irradiation time of the ultraviolet light UV of a plurality of places, and to appropriately perform the maintenance of a plurality of objects irradiated with ultraviolet light.

The irradiation time of the ultraviolet light UV is successively registered in the irradiation time information history 200. For this reason, with the irradiation time information history 200, it is possible to integrate the irradiation time to obtain a cumulative irradiation time. Accordingly, an aspect shown in FIG. 64 may be embodied.

In FIG. 64, the display controller 199 displays a notification window 210 on the display 58 in a case where the cumulative irradiation time exceeds a set time set in advance. The notification window 210 includes a message 211 indicating that the cumulative irradiation time exceeds the set time. That is, the display controller 199 is an example of a "third notification controller" according to the technique of the present disclosure. The display of the notification window 210 is erased with selection of an OK button 212. FIG. 64 illustrates a case where 5000 hours are set as the set time. Notification that the cumulative irradiation time exceeds the set time may be given by playing a voice message indicating that the cumulative irradiation time exceeds the set time, or the like. In this case, a voice controller that controls the play of the voice message operates as the third notification controller.

In this way, the display controller 199 notifies that the cumulative irradiation time exceeds the set time, through the notification window 210. For this reason, the operator OP can appropriately perform maintenance, such as replacement of the ultraviolet light source 34 and/or an object irradiated with the ultraviolet light UV. In a case where the ultraviolet light source 34 and/or the object irradiated with ultraviolet light is replaced, the cumulative irradiation time is reset to 0.

The cumulative irradiation time may be displayed on the display 58 in response to a command of the operator OP, or the like. Notification that the cumulative irradiation time exceeds the set time may be transmitted to, for example, an external maintenance server that is managed by a serviceman of the breast imaging apparatus 10, through the network 13. Then, the serviceman can know the degree of deterioration over time, a replacement timing, and the like of the ultraviolet light source 34 and/or the object irradiated with the ultraviolet light UV while staying at a remote location.

Fifth Embodiment

In the above-described first to fourth embodiments, although the breast imaging apparatus is exemplified as the radiodiagnostic apparatus, the technique of the present disclosure is not limited thereto. As an example, a radiodiagnostic apparatus 300 shown in FIGS. 65 and 66 may be applied.

Figure 65:
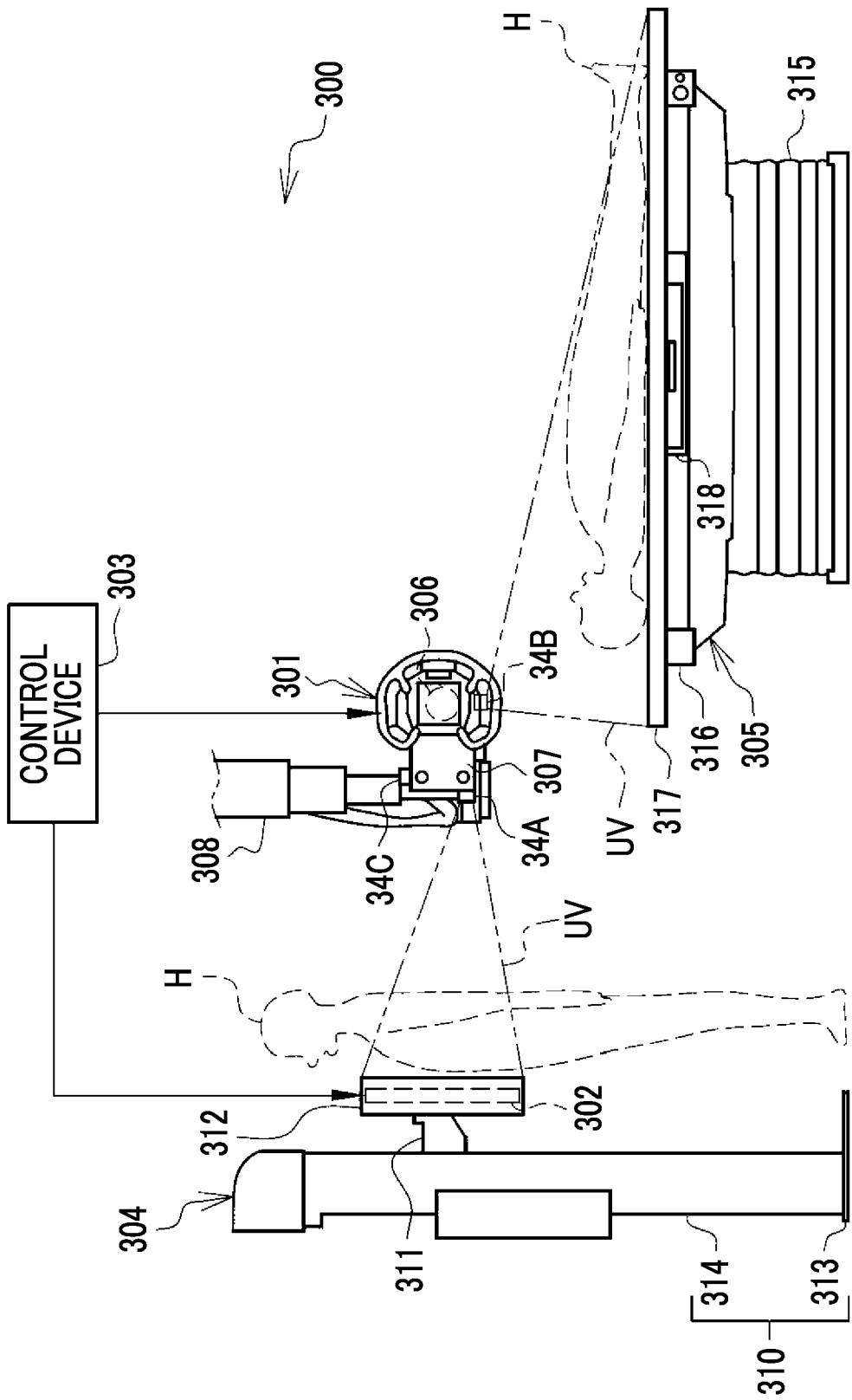
FIG. 65 is a diagram showing a case where, in a radiodiagnostic apparatus comprising an upright imaging table and a decubitus imaging table, radiography is performed using the upright imaging table.
Figure 66:
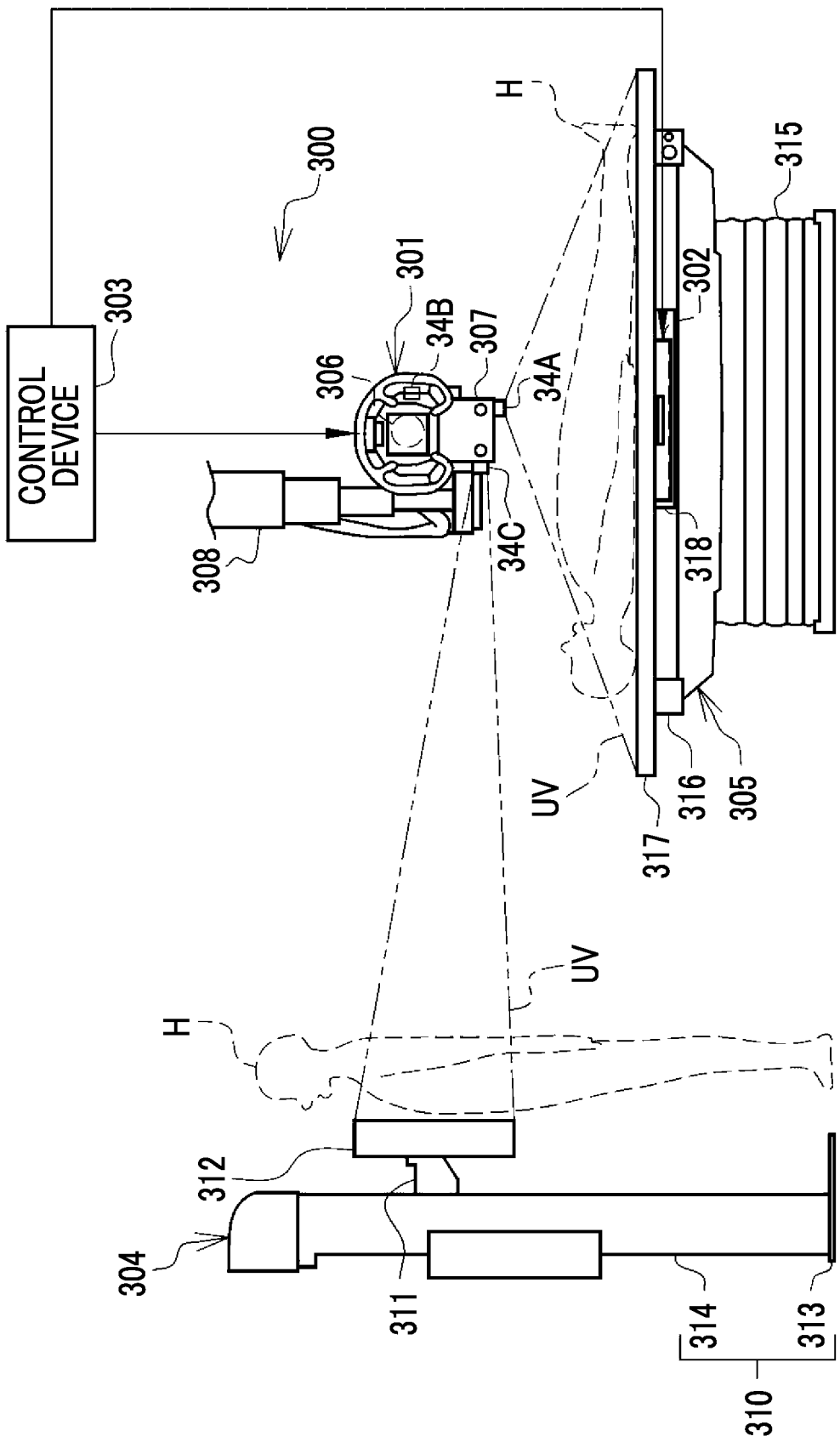
FIG. 66 is a diagram showing a case where, in the radiodiagnostic apparatus comprising the upright imaging table and the decubitus imaging table, radiography is performed using the decubitus imaging table.

In FIGS. 65 and 66, the radiodiagnostic apparatus 300 comprises a radiation source 301, a portable radiation detector 302, a control device 303, an upright imaging table 304, and a decubitus imaging table 305. The radiation source 301, the control device 303, the upright imaging table 304, and the decubitus imaging table 305 are provided in the radiography room 98. One radiation source 301 and one portable radiation detector 302 are prepared and are commonly used in the upright imaging table 304 and the decubitus imaging table 305. A plurality of portable radiation detectors 302 may be prepared.

A radiation tube 306 is incorporated in the radiation source 301. An irradiation field limiter 307 is attached to the radiation source 301. Three ultraviolet light sources 34A, 34B, and 34C are provided on the external surface of the irradiation field limiter 307.

The radiation source 301 is suspended from the ceiling of the radiography room 98 by a column 308. The column 308 is attached to a rail turned around the ceiling through a wheel. The column 308 and the radiation source 301 are movable in a horizontal direction in the radiography room 98 by the rail and the wheel. The column 308 is extendable in a height direction, and accordingly, the radiation source 301 is movable in the height direction. The radiation source 301 is rotatable with respect to the column 308 with an axis perpendicular to the paper surface as a rotation axis.

The portable radiation detector 302 is one in which a detection panel having the detection surface 44, or the like is accommodated in a portable housing, and is referred to as an electronic cassette. The portable radiation detector 302 is accommodated in the upright imaging table 304 or the decubitus imaging table 305 and used. The portable radiation detector 302 is used in a state of being detached from the upright imaging table 304 or the decubitus imaging table 305 and carried with the subject H in the radiography room 98 or is used in a state of being placed below the subject H who lies on a bed in a patient's room (see FIG. 70).

The upright imaging table 304 has a stand 310, a connection portion 311, a holder 312 for upright posture, and the like. The stand 310 is configured with a pedestal 313 that is provided on the floor surface of the radiography room, and a column 314 that extends from the pedestal 313 in the height direction. The connection portion 311 connects the holder 312 for upright posture to the stand 310. The connection portion 311 and the holder 312 for upright posture are movable in the height direction with respect to the column 314 and can perform height adjustment corresponding to the height of the subject H or an imaging part.

The holder 312 for upright posture has a box shape and accommodates the portable radiation detector 302. The holder for upright posture 312 is mostly formed of a conductive material having an electromagnetic wave shielding property, such as aluminum or stainless steel. The holder 312 for upright posture has a front surface facing the radiation source 301, and the front surface is formed of a material transmitting the radiation R, such as carbon.

The decubitus imaging table 305 has a pedestal 315 that is provided on the floor surface of the radiography room 98, a connection portion 316, a top plate 317, a holder 318 for decubitus posture, and the like. The connection portion 316 connects the top plate 317 to the pedestal 315. The pedestal 315 is a lifting type, and accordingly, the top plate 317 and the holder 318 for decubitus posture can perform height adjustment. The top plate 317 is a rectangular plate shape having a length and a width such that the subject H can lie, and is formed of a material transmitting the radiation R, such as carbon.

The holder 318 for decubitus posture is disposed in a space between the pedestal 315 and the top plate 317 formed by the connection portion 316. The holder 318 for decubitus posture has a box shape with a top covered with the top plate 317, and accommodates the portable radiation detector 302. The holder 318 for decubitus posture is formed of a conductive material having an electromagnetic wave shielding property, such as aluminum or stainless steel. The holder 318 for decubitus posture is slidable and movable in a direction in parallel with a longitudinal direction of the top plate 317 by a sliding mechanism (not shown).

FIG. 65 shows a case where the portable radiation detector 302 is accommodated in the holder 312 for upright posture of the upright imaging table 304, and radiography is performed using the upright imaging table 304. In this case, the ultraviolet light source 34A performs the irradiation of the ultraviolet light UV toward a surface of the holder 312 for upright posture facing the subject H. The ultraviolet light source 34B performs the irradiation of the ultraviolet light UV toward the top plate 317 of the decubitus imaging table 305. In this case, the ultraviolet light source 34C does not perform the irradiation of the ultraviolet light UV.

FIG. 66 shows a case where the portable radiation detector 302 is accommodated in the holder 318 for decubitus posture of the decubitus imaging table 305, and radiography is performed using the decubitus imaging table 305. In this case, the ultraviolet light source 34A performs the irradiation of the ultraviolet light UV toward the top plate 317 of the decubitus imaging table 305. The ultraviolet light source 34C performs the irradiation of the ultraviolet light UV toward the surface of the holder 312 for upright posture facing the subject H. In this case, the ultraviolet light source 34B does not perform the irradiation of the ultraviolet light UV.

In summary, the ultraviolet light source 34A irradiates both the upright imaging table 304 and the decubitus imaging table 305 with the ultraviolet light UV. The ultraviolet light source 34B irradiates the decubitus imaging table 305 with the ultraviolet light UV. The ultraviolet light source 34C irradiates the upright imaging table 304 with the ultraviolet light UV. That is, the ultraviolet light source 34A is an example of an ultraviolet light source for an upright imaging table" according to the technique of the present disclosure, and is also an example of an "ultraviolet light source for a decubitus imaging table" according to the technique of the present disclosure. The ultraviolet light source 34B is an example of an "ultraviolet light source for a decubitus imaging table" according to the technique of the present disclosure. The ultraviolet light source 34C is an example of an "ultraviolet light source for an upright imaging table" according to the technique of the present disclosure.

As in the above-described first embodiment, the control device 303 has a controller that switches between the irradiation and the irradiation stop of the ultraviolet light UV by the ultraviolet light sources 34A to 34C in response to a turn-on or off command of the operator OP. Alternatively, as in the above-described second embodiment, the control device 303 has a controller that prohibits the irradiation of the ultraviolet light UV by the ultraviolet light sources 34A to 34C in a case where the set condition is satisfied.

In this way, in the fifth embodiment, the ultraviolet light sources 34A to 34C are provided at places where the upright imaging table 304 and the decubitus imaging table 305 are irradiatable with the ultraviolet light UV. For this reason, it is possible to disinfect the upright imaging table 304 and the decubitus imaging table 305 that are contaminated due to contact of the subject H.

The ultraviolet light source 34A and the 34C for the upright imaging table 304 and the ultraviolet light sources 34A and 34B for the decubitus imaging table 305 are provided separately. For this reason, it is possible to simultaneously disinfect both the upright imaging table 304 and the decubitus imaging table 305. Awaiting time due to disinfection is reduced, and an operation rate of the radiodiagnostic apparatus 300 can be increased. In a case of continuously performing radiography using both the upright imaging table 304 and the decubitus imaging table 305 on one subject H, it is possible to perform radiography in a state in which both the upright imaging table 304 and the decubitus imaging table 305 are in a clean state.

The ultraviolet light sources 34A to 34C are provided on the external surface of the irradiation field limiter 307. For this reason, it is possible to efficiently irradiate the upright imaging table 304 and the decubitus imaging table 305 with the ultraviolet light UV.

The ultraviolet light source 34 is not limited as being provided on the external surface of the irradiation field limiter 307, and may be provided inside the irradiation field limiter 307. A place where the ultraviolet light source 34 is provided is not limited to the irradiation field limiter 307, and may be any place as long as the upright imaging table 304 and the decubitus imaging table 305 are irradiatable with the ultraviolet light UV. For example, the ultraviolet light source 34 may be attached to the wall surface or the ceiling of the radiography room 98.

At least one of the upright imaging table 304 or the decubitus imaging table 305 may be provided. The upright imaging table 304 and the decubitus imaging table 305 may be a table that accommodates a radiation detector to be not attachable and detachable, not a table that accommodates the portable radiation detector 302 to be attachable and detachable.

Sixth Embodiment

Figure 67:
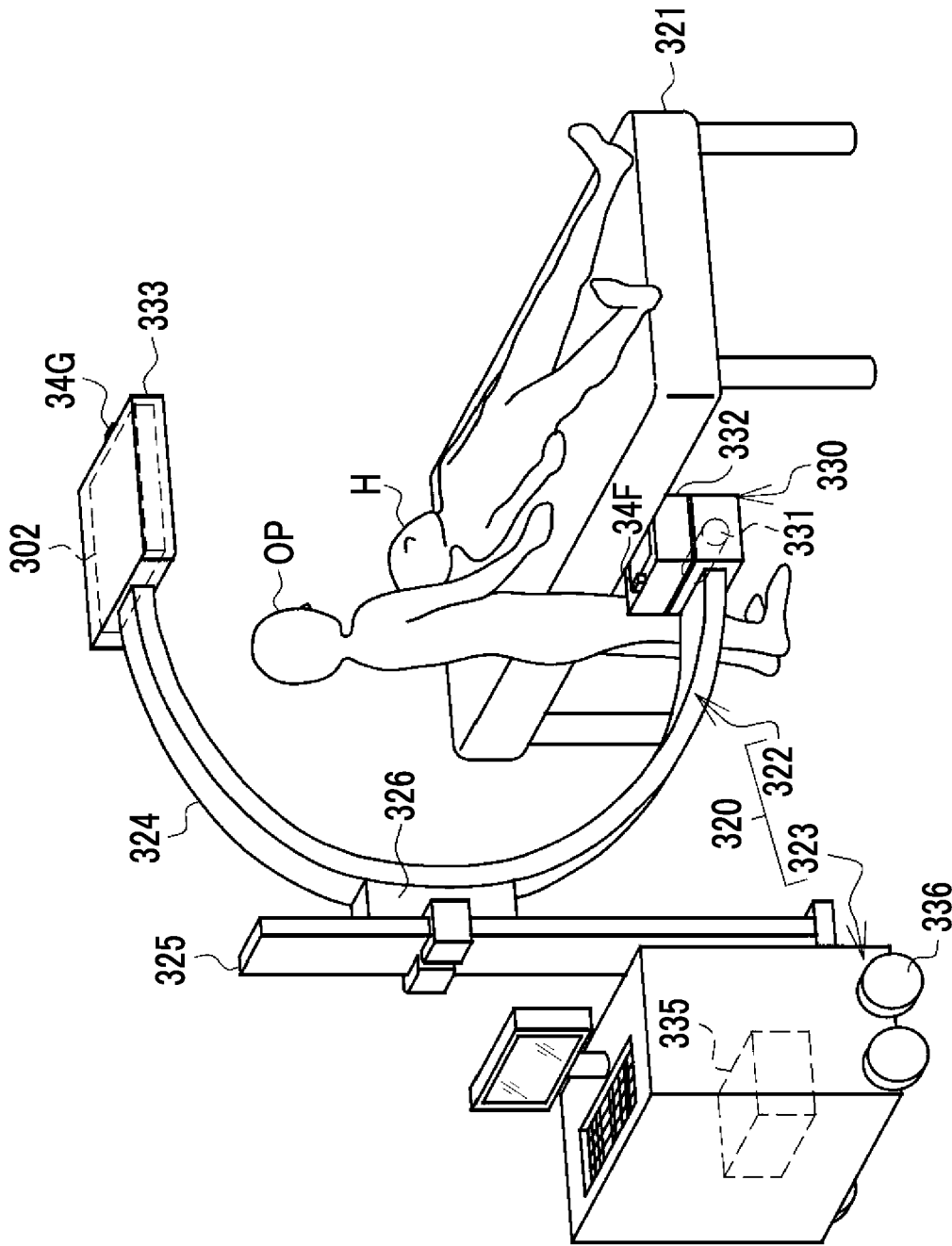
FIG. 67 is a diagram showing a radioscopy apparatus.
Figure 68:
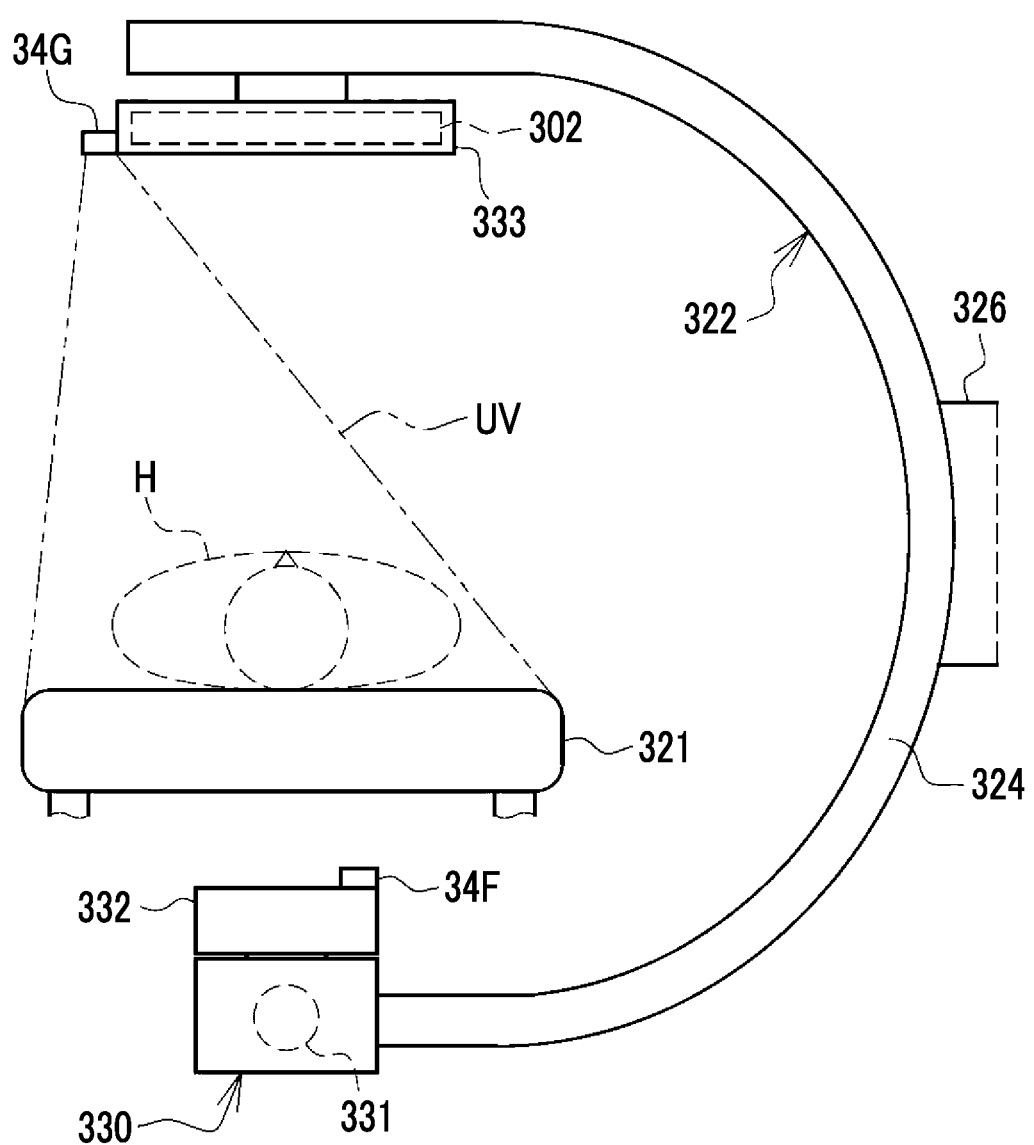
FIG. 68 is a diagram showing a scene in which radioscopy is performed in an under-tube posture.
Figure 69:
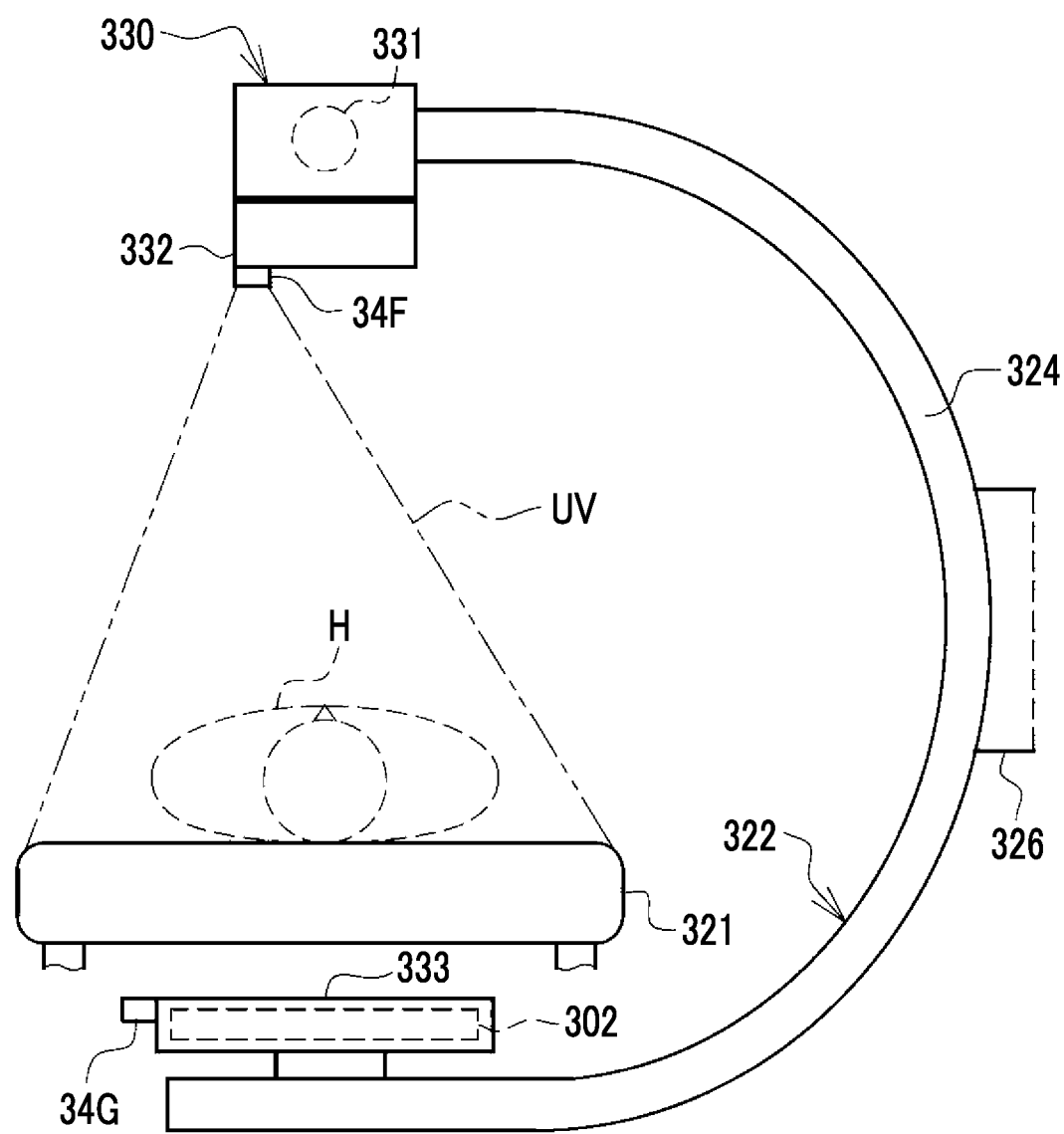
FIG. 69 is a diagram showing a scene in which radioscopy is performed in an over-tube posture.

As the radiodiagnostic apparatus, as an example, a radioscopy apparatus 320 shown in FIGS. 67 to 69 may be applied. The radioscopy apparatus 320 performs radioscopy for continuously capturing a plurality of radiographic images RI at predetermined frame intervals. FIGS. 67 to 69 show a scene in which the operator OP performs radioscopy on a chest of the subject H who lies on an operating table 321 in an operating room. The operating table 321 is an example of a "bed" according to the technique of the present disclosure.

The radioscopy apparatus 320 is configured with an arm portion 322 and a body portion 323. The arm portion 322 has an arm 324 having a substantially C shape as viewed sidewise. The body portion 323 has a column 325 that extends in a height direction. The arm 324 and the column 325 are connected through a connection portion 326. The arm 324 is movable in the height direction with respect to the column 325 and can perform height adjustment corresponding to the position of the subject H with the connection portion 326. The arm 324 is rotatable around a rotation axis that passes through the connection portion 326 and is in parallel with a horizontal direction perpendicular to the height direction.

The radiation source 330 is attached to one end of the arm 324, and the portable radiation detector 302 is attached to the other end of the arm 324. In FIGS. 67 and 68, the radiation source 330 is positioned below the subject H, and the portable radiation detector 302 is positioned above the subject H. Such a positional relationship is referred to as an under-tube posture. On the contrary, in FIG. 69, the radiation source 330 is positioned above the subject H, and the portable radiation detector 302 is positioned below the subject H. Such a positional relationship is referred to as an over-tube posture. In the under-tube posture, the radiation R from the radiation source 330 is partially shielded by the operating table 321, and thus, it is possible to reduce useless exposure to the operator OP or the like in the surrounding of the subject H.

A radiation tube 331 is incorporated in the radiation source 330. An irradiation field limiter 332 is attached to the radiation source 330. An ultraviolet light source 34F is provided on the external surface of the irradiation field limiter 332.

The portable radiation detector 302 is accommodated in a holder 333 provided at the other end of the arm 324 to face the radiation source 330. The portable radiation detector 302 can also be detached from the holder 333 and used. An ultraviolet light source 34G is provided on the external surface of the holder 333.

A control device 335 is provided in the body portion 323. In addition to the control device 335, a battery, a tube voltage generator, and the like are also provided in the body portion 323. Four wheels 336 are attached to a lower portion of the body portion 323 in the front, rear, right, and left. The body portion 323 and the radioscopy apparatus 320 are movable in a medical facility by the wheel 336.

As shown in FIG. 68, in a case of an under-tube posture, the ultraviolet light source 34G performs irradiation of ultraviolet light UV toward the operating table 321. In this case, the ultraviolet light source 34F does not perform irradiation of ultraviolet light UV. On the other hand, as shown in FIG. 69, in a case of an over-tube posture, the ultraviolet light source 34F performs irradiation of ultraviolet light UV toward the operating table 321. In this case, the ultraviolet light source 34G does not perform irradiation of ultraviolet light UV.

As in the above-described first embodiment, the control device 335 has a controller that switches between irradiation and irradiation stop of ultraviolet light UV by the ultraviolet light sources 34F and 34G in response to a turn-on or off command of the operator OP. Alternatively, as in the above-described second embodiment, the control device 335 has a controller that prohibits irradiation of ultraviolet light UV by the ultraviolet light sources 34F and 34G in a case where the set condition is satisfied.

In this way, in the sixth embodiment, the radioscopy apparatus 320 comprises the arm 324 that integrally retains the radiation source 330 and the portable radiation detector 302 at facing positions. The ultraviolet light sources 34F and 34G are provided at places where the operating table 321 that is disposed between the radiation source 330 and the portable radiation detector 302 and on which the subject H lies is irradiatable with the ultraviolet light UV. For this reason, it is possible to disinfect the operating table 321 contaminated due to contact of the subject H.

The ultraviolet light sources 34F and 34G are provided on the external surface of the irradiation field limiter 332. For this reason, it is possible to efficiently irradiate the operating table 321 with the ultraviolet light UV.

To reliably prevent the eyes of the operator OP or the like from being irradiated with the ultraviolet light UV, the irradiation of the ultraviolet light source 34F may be prohibited in a case of the under-tube posture, and the irradiation of the ultraviolet light source 34G may be prohibited in a case of the over-tube posture.

The ultraviolet light source 34 is not limited as being provided on the external surface of the irradiation field limiter 332, and may be provided inside the irradiation field limiter 332. The place where the ultraviolet light source 34 is provided is not limited to the irradiation field limiter 332, and may be any place as long as the operating table 321 is irradiatable with the ultraviolet light UV. As exemplified above, the ultraviolet light source 34 may be attached to the external surface of the holder 333 or may be attached to the arm 324. The ultraviolet light source 34 may be attached to a wall surface or a ceiling of the operating room.

The holder 333 may be a holder that accommodates the portable radiation detector 302 to be not attachable and detachable, not a holder that accommodates the radiation detector to be attachable and detachable. The radioscopy apparatus 320 may be a type of movable using the wheels 336 or may be a type of being stationary in the operating room.

Seventh Embodiment

Figure 70:
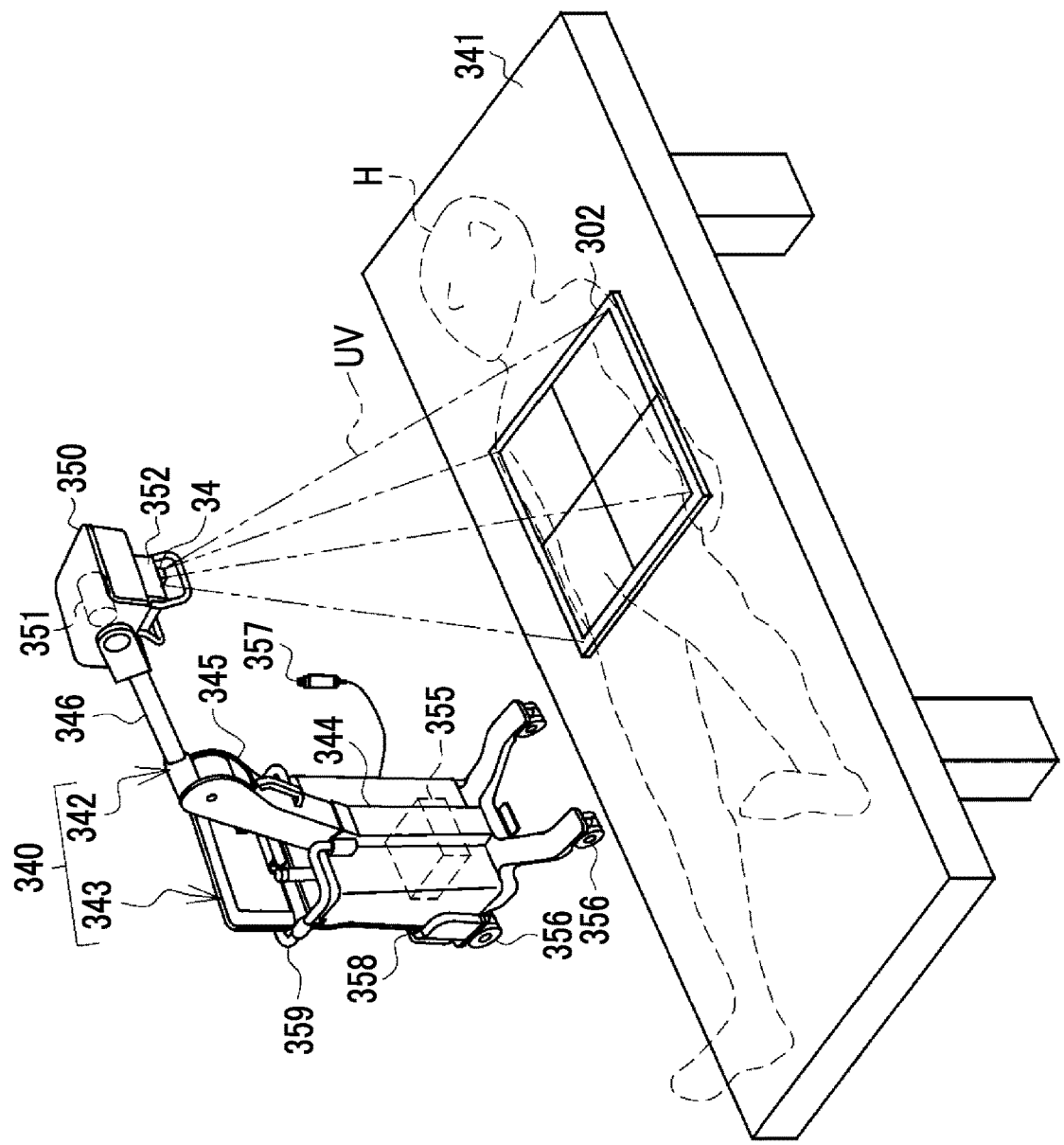
FIG. 70 is a diagram showing a mobile radiation generation apparatus.

The radiodiagnostic apparatus may be a mobile radiation generation apparatus 340 shown in FIG. 70 as an example. The mobile radiation generation apparatus 340 is used in so-called round imaging for imaging the subject H while visiting patient's rooms. For this reason, the mobile radiation generation apparatus 340 is also referred to as a treatment cart. The mobile radiation generation apparatus 340 can be carried in the operating room and used in the middle of an operation similarly to the radioscopy apparatus 320 of the above-described sixth embodiment. The mobile radiation generation apparatus 340 can also be carried in an outdoor disaster site and used in emergency. FIG. 70 shows a scene in which radiography is performed on a chest of the subject H in a state in which the portable radiation detector 302 is placed below the subject H who lies on a bed 341 of a patient's room.

The mobile radiation generation apparatus 340 is configured with an arm portion 342 and a body portion 343. The arm portion 342 has a first arm 345 that is continuously provided upward from a column 344 of the body portion 343 at a predetermined angle, and a second arm 346. The second arm 346 can be bent or extended with respect to the first arm 345.

A radiation source 350 is attached to a distal end of the second arm 346. A radiation tube 351 is incorporated in the radiation source 350. An irradiation field limiter 352 is attached to the radiation source 350. An ultraviolet light source 34 is provided on the external surface of the irradiation field limiter 352. The ultraviolet light source 34 performs the irradiation of the ultraviolet light UV toward the portable radiation detector 302 placed on the bed 341.

A control device 355 is provided in the body portion 343. In addition to the control device 355, a battery, a tube voltage generator, and the like are also provided in the body portion 343. Four wheels 356 are attached to a lower portion of the body portion 343 in the front, rear, right, and left. The body portion 343 and the mobile radiation generation apparatus 340 are movable in a medical facility using the wheels 356.

An irradiation switch 357 that is used for the operator OP to give a command to start the irradiation of the radiation R is connected to the body portion 343. In the lower portion of the body portion 343, a pocket 358 that stores the portable radiation detector 302 is provided. There are a plurality of kinds of portable radiation detectors 302 having a longitudinal/lateral size of 17 inches×17 inches, 17 inches×14 inches, 12 inches×10 inches, and the like. The pocket 358 can store a plurality of kinds of portable radiation detectors 302 regardless of the kinds. The pocket 358 has a function of charging a battery of the stored portable radiation detector 302.

A banister 359 is provided in an upper portion of the body portion 343. The banister 359 is held by the operator OP to operate the body portion 343 and the mobile radiation generation apparatus 340.

As in the above-described first embodiment, the control device 355 has a controller that switches between the irradiation and the irradiation stop of the ultraviolet light UV by the ultraviolet light source 34 in response to a turn-on or off command of the operator OP. Alternatively, as in the above-described second embodiment, the control device 355 has a controller that prohibits the irradiation of the ultraviolet light UV by the ultraviolet light source 34 in a case where the set condition is satisfied.

In this way, in the seventh embodiment, the mobile radiation generation apparatus 340 comprises the body portion 343 on which the radiation source 350 and the portable radiation detector 302 are mounted and that has the wheels 356 for running. The ultraviolet light source 34 is provided at a place where the portable radiation detector 302 is irradiatable with the ultraviolet light UV. For this reason, it is possible to disinfect the portable radiation detector 302 contaminated due to contact of the subject H.

The ultraviolet light source 34 is provided on the external surface of the irradiation field limiter 352. For this reason, it is possible to efficiently irradiate the portable radiation detector 302 with the ultraviolet light UV.

The ultraviolet light source 34 is not limited as being provided on the external surface of the irradiation field limiter 352, and may be provided inside the irradiation field limiter 352. The place where the ultraviolet light source 34 is provided is not limited to the irradiation field limiter 352, and may be any place as long as the portable radiation detector 302 is irradiatable with the ultraviolet light UV. The ultraviolet light source 34 may be attached to the second arm 346. The ultraviolet light source 34 may be provided in the pocket 358, and the portable radiation detector 302 stored in the pocket 358 may be irradiated with the ultraviolet light UV. The ultraviolet light source 34 may be provided at a place where the irradiation switch 357 and the banister 359 are irradiatable with the ultraviolet light UV.

In the mobile radiation generation apparatus 340, there is a case where a so-called computed radiography (CR) cassette incorporated with an imaging plate instead of a detection panel or the like, not the portable radiation detector 302, is used. In a case where the CR cassette is used, the irradiation of the ultraviolet light UV may be performed from the ultraviolet light source 34 to the CR cassette.

In the middle of moving the mobile radiation generation apparatus 340 using the wheels 356, the irradiation of the ultraviolet light UV may be performed from the ultraviolet light source 34 to a floor surface of a medical facility to disinfect the floor surface of the medical facility.

Eighth Embodiment

Figure 71:
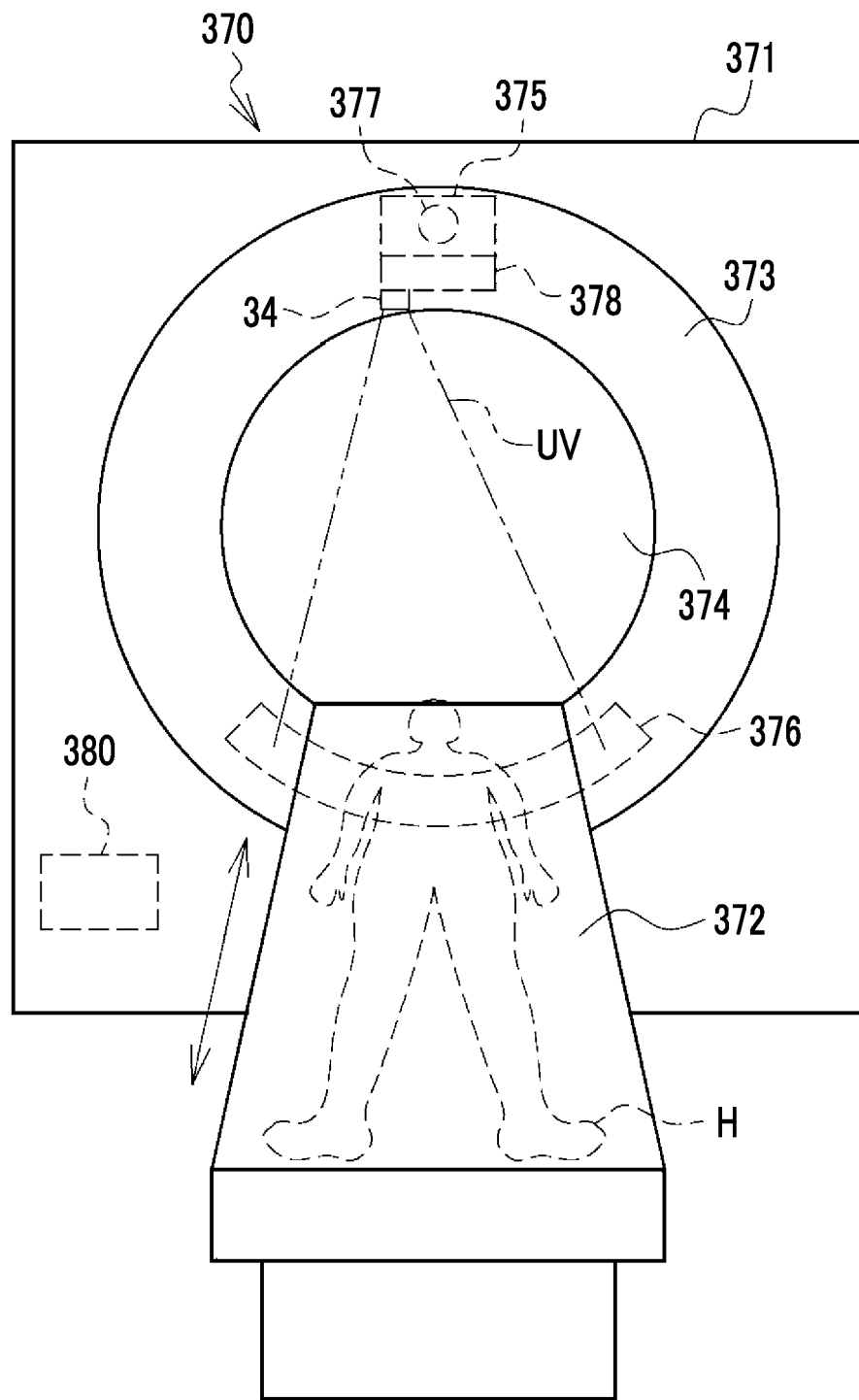
FIG. 71 is a diagram showing a radiation CT apparatus.

As the radiodiagnostic apparatus, as an example, a radiation computed tomography (CT) apparatus 370 shown in FIG. 71 may be applied. The radiation CT apparatus 370 is provided in the radiography room 98. The radiation CT apparatus 370 comprises a gantry 371 and a bed 372. The gantry 371 has a gantry rotating portion 373. The gantry rotating portion 373 has an annular shape and is rotatably supported in the gantry 371. The gantry rotating portion 373 forms a circular bore portion 374. The subject H lies on the bed 372. The bed 372 is slid and moved in the bore portion 374 by a sliding mechanism (not shown).

A radiation source 375 and a radiation detector 376 are incorporated in the gantry rotating portion 373. The radiation source 375 and the radiation detector 376 are disposed at facing positions with the bore portion 374 interposed therebetween. The radiation source 375 and the radiation detector 376 rotates with the rotation of the gantry rotating portion 373 in a state of maintaining such a positional relationship. The radiation source 375 and the radiation detector 376 reconfigure a plurality of radiographic images RI obtained by radiography at a plurality of rotation positions, whereby a tomographic image is generated.

A radiation tube 377 is incorporated in the radiation source 375. An irradiation field limiter 378 is attached to the radiation source 375. An ultraviolet light source 34 is provided on the external surface of the irradiation field limiter 378. The ultraviolet light source 34 performs the irradiation of the ultraviolet light UV toward the bed 372 that is slid and moved in the bore portion 374 in a state shown in FIG. 71 in which the radiation source 375 is disposed above and the radiation detector 376 is disposed below.

A control device 380 is provided in the gantry 371. In addition to the control device 380, a tube voltage generator and the like are also provided in the gantry 371.

As in the above-described first embodiment, the control device 380 has a controller that switches between the irradiation and the irradiation stop of the ultraviolet light UV by the ultraviolet light source 34 in response to a turn-on or off command of the operator OP. Alternatively, as in the above-described second embodiment, the control device 380 has a controller that prohibits the irradiation of the ultraviolet light UV by the ultraviolet light source 34 in a case where the set condition is satisfied.

In this way, in the eighth embodiment, the radiation CT apparatus 370 comprises the gantry 371 that incorporates the radiation source 375 and the radiation detector 376, and the bed 372 on which the subject H lies and that is slid and moved in the gantry 371. The ultraviolet light source 34 is provided at a place where the bed 372 is irradiatable with the ultraviolet light UV. For this reason, it is possible to disinfect the bed 372 contaminated due to contact of the subject H.

The ultraviolet light source 34 is provided on the external surface of the irradiation field limiter 378. For this reason, it is possible to efficiently irradiate the bed 372 with the ultraviolet light UV.

The ultraviolet light source 34 is not limited as being provided on the external surface of the irradiation field limiter 378, and may be provided inside the irradiation field limiter 378. The place where the ultraviolet light source 34 is provided is not limited to the irradiation field limiter 378, and may be any place as long as the bed 372 is irradiatable with the ultraviolet light UV. The ultraviolet light source 34 may be provided on the external surface of the gantry rotating portion 373. The ultraviolet light source 34 may be attached to the wall surface or the ceiling of the radiography room 98.

A plurality of ultraviolet light source 34 may be provided on the external surface of the gantry rotating portion 373 at equal intervals. Then, it is possible to disinfect not only a top plate of the bed 372 on which the subject H lies, but also the side surfaces of the bed 372, the inner peripheral surface of the gantry rotating portion 373 configuring the bore portion 374, and the like. The side surfaces of the bed 372 are likely to be contaminated by the subject H putting the hands thereon. The inner peripheral surface of the gantry rotating portion 373 is likely to be contaminated due to the expiration of the subject H. For this reason, in a case where the side surfaces of the bed 372 and the inner peripheral surface of the gantry rotating portion 373 are also disinfected, it is possible to further increase safety.

Ninth Embodiment

As an example, in a ninth embodiment shown in FIGS. 72 to 74, the technique of the present disclosure is applied to a nuclear magnetic resonance imaging apparatus (hereinafter, abbreviated as an MRI apparatus) 400A or 400B.

Figure 72:
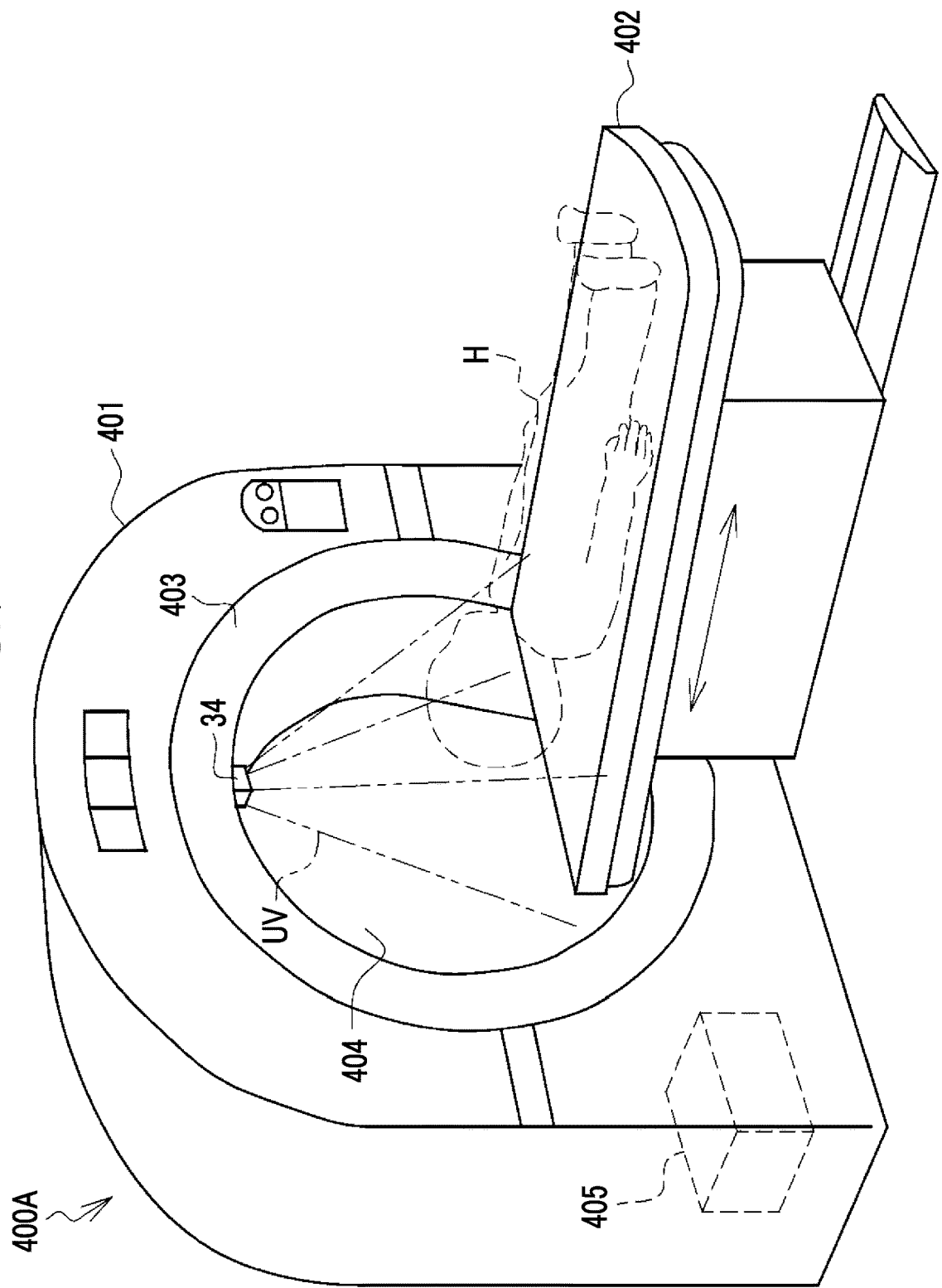
FIG. 72 is a tunnel type MRI apparatus.

In FIG. 72, the MRI apparatus 400A comprises a gantry 401 and an imaging table 402. The gantry 401 has an annular gantry body 403. The gantry body 403 forms a circular bore portion 404. The subject H lies on a bed 402. The bed 402 is slid and moved in the bore portion 404 by a sliding mechanism (not shown).

The ultraviolet light source 34 is provided on the external surface of an upper portion of the gantry body 403 facing the bed 402. The ultraviolet light source 34 performs the irradiation of the ultraviolet light UV toward the bed 402 that is slid and moved in the bore portion 404.

A control device 405 is provided in the gantry 401. As in the above-described first embodiment, the control device 405 has a controller that switches between the irradiation and the irradiation stop of the ultraviolet light UV by the ultraviolet light source 34 in response to a turn-on or off command of the operator OP. Alternatively, as in the above-described second embodiment, the control device 405 has a controller that prohibits the irradiation of the ultraviolet light UV by the ultraviolet light source 34 in a case where the set condition is satisfied.

Figure 73:
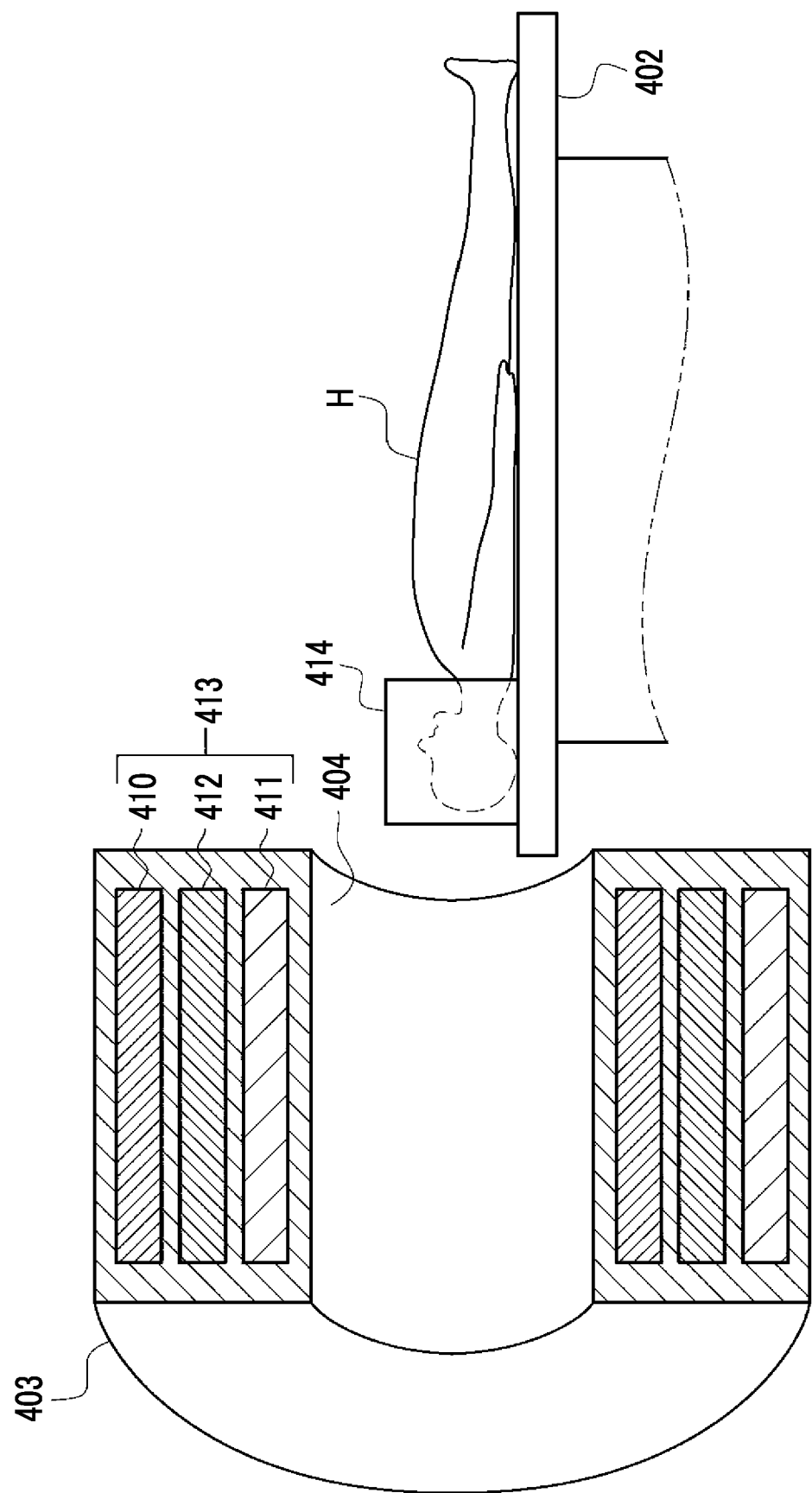
FIG. 73 is a diagram showing the inside and the like of a gantry body.

As an example, as shown in FIG. 73, the gantry body 403 incorporates a static magnetic field magnet 410, a high frequency magnetic field coil 411, and a gradient magnetic field coil 412. The static magnetic field magnet 410, the high frequency magnetic field coil 411, and the gradient magnetic field coil 412 have the same annular shape as the gantry body 403. The static magnetic field magnet 410 is positioned on the outermost side of the gantry body 403, and generates a uniform static magnetic field in an imaging space including the bore portion 404 and the like. The high frequency magnetic field coil 411 is positioned on the innermost side of the gantry body 403, and generates a high frequency magnetic field for causing nuclear magnetic resonance in hydrogen atoms in the imaging part of the subject H. The gradient magnetic field coil 412 is positioned between the static magnetic field magnet 410 and the high frequency magnetic field coil 411, and generates a linear gradient magnetic field on the static magnetic field in a superimposed manner to give positional information to a nuclear magnetic resonance signal generated from the imaging part by the high frequency magnetic field. The static magnetic field magnet 410, the high frequency magnetic field coil 411, and the gradient magnetic field coil 412 configure a magnetic field generation unit 413.

A reception coil 414 is disposed on the bed 402. The reception coil 414 receives the nuclear magnetic resonance signal. A nuclear magnetic resonance image is generated based on the nuclear magnetic resonance signal received by the reception coil 414.

Although the MM apparatus 400A shown in FIGS. 72 and 73 is a so-called tunnel type having the annular gantry body 403, the technique of the present disclosure is not limited thereto. The MRI apparatus 400B, called an open type, shown in FIG. 74 may be applied.

Figure 74:
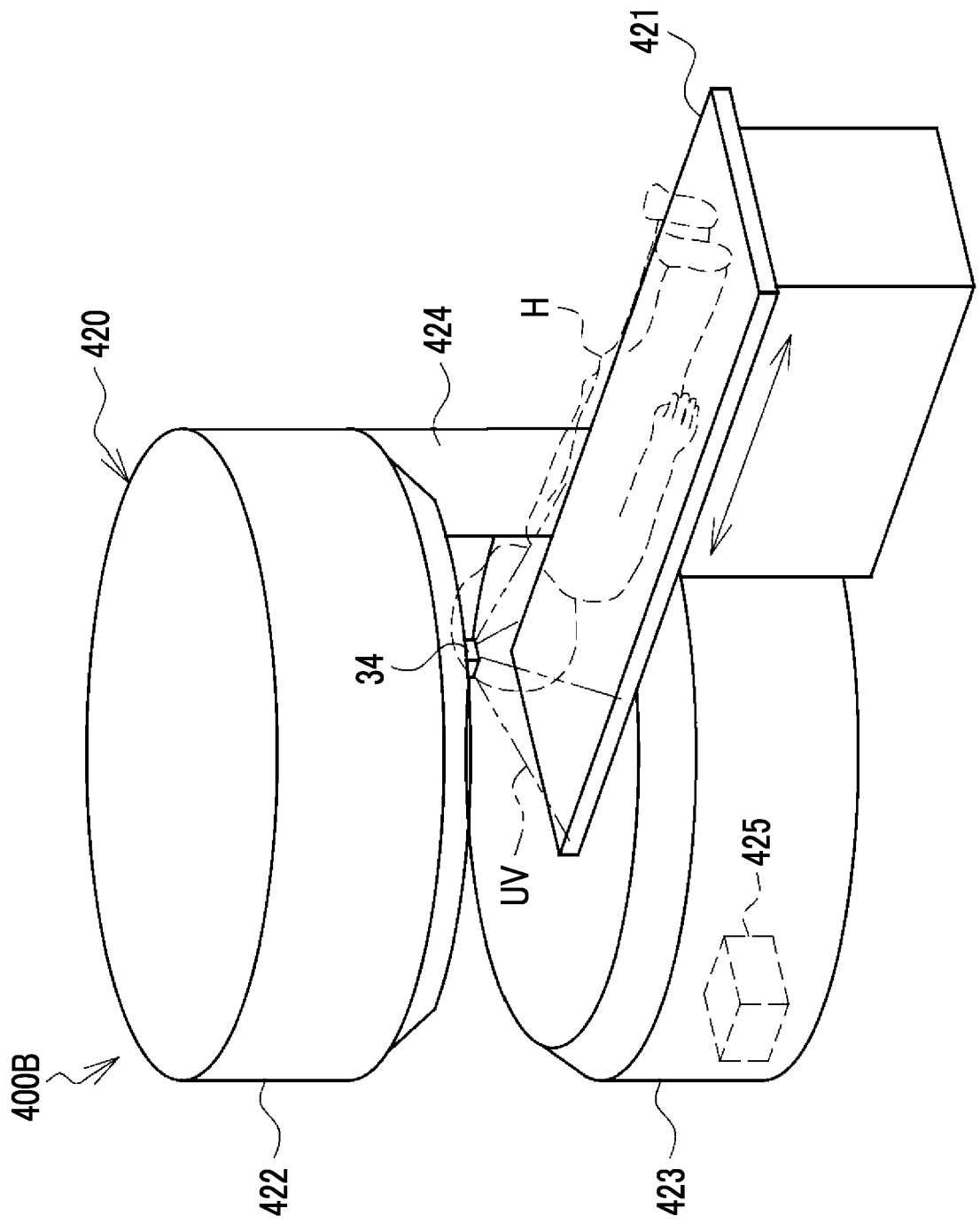
FIG. 74 is a diagram showing an open type MRI apparatus.

In FIG. 74, the MRI apparatus 400B comprises a gantry 420 and an imaging table 421. The gantry 420 has a configuration in which an upper gantry 422 and a lower gantry 423 are connected by a connection portion 424. The bed 421 is slid and moved in a space between the upper gantry 422 and the lower gantry 423. Though not shown, similarly to the MRI apparatus 400A, each of the upper gantry 422 and the lower gantry 423 incorporates a magnetic field generation unit configured with a static magnetic field magnet, a high frequency magnetic field coil, and a gradient magnetic field coil. A reception coil is disposed on a bed 421.

The ultraviolet light source 34 is provided on the external surface of the upper gantry 422 facing the bed 421. The ultraviolet light source 34 performs the irradiation of the ultraviolet light UV toward the bed 421 that is slid and moved in the space between the upper gantry 422 and the lower gantry 423.

A control device 425 is provided in the lower gantry 423. As in the above-described first embodiment, the control device 425 has a controller that switches between the irradiation and the irradiation stop of the ultraviolet light UV by the ultraviolet light source 34 in response to a turn-on or off command of the operator OP. Alternatively, as in the above-described second embodiment, the control device 425 has a controller that prohibits the irradiation of the ultraviolet light UV by the ultraviolet light source 34 in a case where the set condition is satisfied.

In this way, in the ninth embodiment, in the MRI apparatus 400A or 400B, the ultraviolet light source 34 is provided at a place where the bed 402 or 421 is irradiatable with the ultraviolet light UV. For this reason, it is possible to disinfect the bed 402 or 421 contaminated due to contact of the subject H.

The place where the ultraviolet light source 34 is provided is not limited to the place exemplified above, and may be any place as long as the bed 402 or 421 is irradiatable with the ultraviolet light UV. For example, the ultraviolet light source 34 may be attached to a wall surface or a ceiling of an imaging room.

In a case of the MRI apparatus 400A, similarly to the radiation CT apparatus 370 of the above-described eighth embodiment, a plurality of ultraviolet light sources 34 may be provided on the external surface of the gantry body 403 at equal intervals. Then, it is possible to disinfect the side surfaces of the imaging table 402, the inner peripheral surface of the gantry body 403 configuring the bore portion 404, and the like, and to further increase safety.

From the description of the ninth embodiment, it is possible to ascertain Supplementary Items 1 and 2 described below.

Supplementary Item 1

A nuclear magnetic resonance imaging apparatus comprising:
　a gantry that incorporates a magnetic field generation unit configured to generate a magnetic field;
　a reception coil that receives a nuclear magnetic resonance signal generated from an imaging part of a subject by the magnetic field;
　a bed on which the subject lies and that is slid and moved in the gantry;
　an ultraviolet light source that is provided at a place where the bed is irradiatable with the ultraviolet light; and
　a controller that prohibits the irradiation of the ultraviolet light by the ultraviolet light source in a case where a predetermined set condition is satisfied.

Supplementary Item 2

A nuclear magnetic resonance imaging apparatus comprising:
　a gantry that incorporates a magnetic field generation unit configured to generate a magnetic field;
　a reception coil that receives a nuclear magnetic resonance signal generated from an imaging part of a subject by the magnetic field;
　a bed on which the subject lies and that is slid and moved in the gantry; and
　an ultraviolet light source that is provided at a place where the bed is irradiatable with the ultraviolet light.

In the above-described fifth to ninth embodiments, the ultraviolet light source 150 may be used instead of the ultraviolet light source 34. The above-described fifth to ninth embodiments and the above-described third embodiment and/or the above-described fourth embodiment may be embodied in combination. The aspect shown in FIGS. 59 to 61 in which the ultraviolet light sources are provided in the foot switch may be applied to the above-described fifth to ninth embodiments. For example, the foot switch may be used to adjust the height of the holder 312 for upright posture of the upright imaging table 304 of the above-described fifth embodiment and/or the top plate 317 and the holder 318 for decubitus posture of the decubitus imaging table 305, and ultraviolet light sources may be provided in the foot switch.

In a case where the above-described fourth embodiment in which the irradiation time of the ultraviolet light UV is measured and the measured irradiation time is stored is applied to the above-described fifth embodiment in which the radiodiagnostic apparatus 300 having the upright imaging table 304 and the decubitus imaging table 305 is illustrated, an irradiation time of each of the upright imaging table 304 and the decubitus imaging table 305 may be measured and stored. In a case where the above-described fourth embodiment in which the irradiation time of the ultraviolet light UV is measured and the measured irradiation time is stored is applied to the above-described seventh embodiment in which the mobile radiation generation apparatus 340 is illustrated as the radiodiagnostic apparatus, identification information may be transmitted from a plurality of portable radiation detectors 302 through wireless communication or the like, and an irradiation time may be stored for each piece of transmitted identification information.

In the respective embodiments described above, for example, as the hardware structures of processing units that execute various kinds of processing, such as the reception units 70 and 120, the RW controllers 71 and 198, the controllers 72, 96, 111, 122, 132, 142, 170, and 195, the image processing unit 73, the display controllers 74, 100, and 199, the mode switching unit 130, and the measurement unit 196, various processors described below can be used. Various processors include a programmable logic device (PLD) that is a processor capable of changing a circuit configuration after manufacture, such as a field programmable gate array (FPGA), a dedicated electric circuit that is a processor having a circuit configuration dedicatedly designed for executing specific processing, such as an application specific integrated circuit (ASIC), and the like in addition to the CPU 57 that is a general-purpose processor executing software (operation program 65) to function as various processing units, as described above.

One processing unit may be configured of one of various processors described above or may be configured of a combination of two or more processors (for example, a combination of a plurality of FPGAs and/or a combination of a CPU and an FPGA) of the same type or different types. A plurality of processing units may be configured of one processor.

As an example where a plurality of processing units are configured of one processor, first, as represented by a computer, such as a client or a server, there is a form in which one processor is configured of a combination of one or more CPUs and software, and the processor functions as a plurality of processing units. Second, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, as the hardware structure of various processors, more specifically, an electric circuit (circuitry), in which circuit elements, such as semiconductor elements, are combined, can be used.

The technique of the present disclosure can also be appropriately combined with various embodiments and/or various modification examples described above. The technique of the present disclosure is not limited to the above-described embodiments, and various configurations can be of course employed without departing from the spirit and scope of the technique of the present disclosure.

The content of the above description and the content of the drawings are detailed description of portions according to the technique of the present disclosure, and are merely examples of the technique of the present disclosure. For example, the above description relating to configuration, function, operation, and advantageous effects is description relating to examples of configuration, function, operation, and advantageous effects of the portions according to the technique of the present disclosure. Thus, it is needless to say that unnecessary portions may be deleted, new elements may be added, or replacement may be made to the content of the above description and the content of the drawings without departing from the gist of the technique of the present disclosure. Furthermore, to avoid confusion and to facilitate understanding of the portions according to the technique of the present disclosure, description relating to common technical knowledge and the like that does not require particular description to enable implementation of the technique of the present disclosure is omitted from the content of the above description and the content of the drawings.

In the specification, "A and/or B" is synonymous with "at least one of A or B". That is, "A and/or B" may refer to A alone, B alone, or a combination of A and B. Furthermore, in the specification, a similar concept to "A and/or B" applies to a case in which three or more matters are expressed by linking the matters with "and/or".

All of the documents, patent applications, and technical standards in the specification are incorporated herein by reference to the same extent that the individual documents, patent applications, and technical standards are described specifically and independently.

What is claimed is:

1. A radiodiagnostic apparatus comprising:
    a radiation source that irradiates an imaging part of a subject with radiation;
    a radiation detector that detects the radiation transmitted through the imaging part to output a radiographic image;
    an ultraviolet light source that performs irradiation of ultraviolet light; and
    a controller that prohibits the irradiation of the ultraviolet light by the ultraviolet light source in a case where a predetermined set condition is satisfied; wherein
    in a case of making the ultraviolet light source perform the irradiation of the ultraviolet light, the controller makes the ultraviolet light source continue the irradiation of the ultraviolet light for a predetermined first set period;
    the controller makes the ultraviolet light source interrupt the irradiation of the ultraviolet light in a case where determination is made that the set condition is satisfied before the first set period elapses; and
    the controller makes the ultraviolet light source restart the irradiation of the ultraviolet light in a case where determination is made that the set condition is not satisfied within a predetermined second set period after the irradiation of the ultraviolet light is interrupted.

2. The radiodiagnostic apparatus according to claim 1, further comprising:
    a camera,
    wherein the controller determines that the set condition is satisfied in a case where a person is shown in a captured image of the camera.

3. The radiodiagnostic apparatus according to claim 1, further comprising:
    a moving body detection sensor that detects a moving body,
    wherein the controller determines that the set condition is satisfied in a case where the moving body detection sensor detects the moving body.

4. The radiodiagnostic apparatus according to claim 1, further comprising:
    a reception unit that receives an imaging menu indicating an imaging content,
    wherein the controller determines that the set condition is satisfied in a case where the reception unit receives the imaging menu.

5. A radiodiagnostic apparatus according to claim 1, further comprising:
a mode switching unit that switches between a first operation mode where power consumption is relatively high and a second operation mode where power consumption is relatively low,
wherein the controller determines that the set condition is not satisfied in a case where the mode switching unit performs switching to the second operation mode and permits the irradiation of the ultraviolet light by the ultraviolet light source.

6. The radiodiagnostic apparatus according to claim 1, further comprising:
a first notification controller that performs control for notifying that the irradiation of the ultraviolet light is interrupted.

7. The radiodiagnostic apparatus according to claim 1, wherein the imaging part is a breast, and
the ultraviolet light source is provided at a place where at least one of an imaging table that incorporates the radiation detector and on which the breast is placed or a pressing plate that presses the breast while sandwiching the breast with the imaging table is irradiatable with the ultraviolet light.

8. The radiodiagnostic apparatus according to claim 7, further comprising:
an irradiation field limiter that is provided between the radiation source and the pressing plate, and defines an irradiation field of the radiation to the imaging table,
wherein the ultraviolet light source is provided on an external surface of the irradiation field limiter.

9. The radiodiagnostic apparatus according to claim 8, wherein the radiation source and the radiation detector are capable of changing an angle with respect to the breast,
the radiodiagnostic apparatus further comprises:
an angle detection sensor that detects the angle, and
the controller determines that the set condition is satisfied in a case where the angle detected by the angle detection sensor is a predetermined set angle.

10. The radiodiagnostic apparatus according to claim 7, further comprising:
an irradiation field limiter that is provided between the radiation source and the pressing plate, and defines an irradiation field of the radiation to the imaging table,
wherein the ultraviolet light source is provided inside the irradiation field limiter.

11. The radiodiagnostic apparatus according to claim 10, wherein an irradiation field lamp that performs irradiation of light representing the irradiation field toward the imaging table is provided in the irradiation field limiter, and
the ultraviolet light source is provided alongside the irradiation field lamp.

12. The radiodiagnostic apparatus according to claim 7, wherein the pressing plate is formed of a material that transmits the ultraviolet light.

13. The radiodiagnostic apparatus according to claim 1, further comprising:
at least one of an upright imaging table or a decubitus imaging table that accommodates the radiation detector,
wherein the ultraviolet light source is provided at a place where at least one of the upright imaging table or the decubitus imaging table is irradiatable with the ultraviolet light.

14. The radiodiagnostic apparatus according to claim 13, wherein, in a case where the radiodiagnostic apparatus comprises both the upright imaging table and the decubitus imaging table, an ultraviolet light source for the upright imaging table and an ultraviolet light source for the decubitus imaging table are provided separately.

15. The radiodiagnostic apparatus according to claim 13, wherein the ultraviolet light source is provided in an irradiation field limiter that defines an irradiation field of the radiation.

16. The radiodiagnostic apparatus according to claim 1, further comprising:
an arm that integrally retains the radiation source and the radiation detector at facing positions,
wherein the ultraviolet light source is provided at a place where a bed that is disposed between the radiation source and the radiation detector and on which the subject lies is irradiatable with the ultraviolet light.

17. The radiodiagnostic apparatus according to claim 1, further comprising:
a body portion on which the radiation source and a portable radiation detector are mounted and that has wheels for running,
wherein the ultraviolet light source is provided at a place where the portable radiation detector is irradiatable with the ultraviolet light.

18. The radiodiagnostic apparatus according to claim 1, further comprising:
a gantry that incorporates the radiation source and the radiation detector; and
a bed on which the subject lies and that slides and moves in the gantry,
wherein the ultraviolet light source is provided at a place where the bed is irradiatable with the ultraviolet light.

19. The radiodiagnostic apparatus according to claim 1, further comprising:
a foot switch that is stepped on by an operator with a foot and operated,
wherein the ultraviolet light source is provided at a place where the foot switch is irradiatable with the ultraviolet light.

20. The radiodiagnostic apparatus according to claim 19, wherein the ultraviolet light source is provided in a foot-operating portion of the foot switch.

21. The radiodiagnostic apparatus according to claim 19, further comprising:
a cover that covers the foot switch from above,
wherein the ultraviolet light source is provided inside the cover.

22. The radiodiagnostic apparatus according to claim 1, further comprising:
a measurement unit that measures an irradiation time of the ultraviolet light by the ultraviolet light source; and
a storage controller that stores the irradiation time measured by the measurement unit in a storage unit.

23. The radiodiagnostic apparatus according to claim 22, wherein there are a plurality of places where the irradiation of the ultraviolet light is performed,
the measurement unit measures the irradiation time for each of the plurality of places, and
the storage controller stores the irradiation time of each of the plurality of places measured by the measurement unit for each of the plurality of places.

24. The radiodiagnostic apparatus according to claim 22, further comprising:

a second notification controller that performs control for notifying of the irradiation time.

25. The radiodiagnostic apparatus according to claim 22, further comprising:
a third notification controller that, in a case where a cumulative irradiation time obtained by integrating the irradiation time exceeds a set time set in advance, performs control for notifying that the cumulative irradiation time exceeds the set time.

26. A method of operating a radiodiagnostic apparatus, the method comprising:
irradiating an imaging part of a subject with radiation from a radiation source;
detecting the radiation transmitted through the imaging part with a radiation detector to output a radiographic image;
performing irradiation of ultraviolet light from an ultraviolet light source; and
prohibiting the irradiation of the ultraviolet light by the ultraviolet light source in a case where a predetermined set condition is satisfied;
in a case of making the ultraviolet light source perform the irradiation of the ultraviolet light, continuing the irradiation of the ultraviolet light for a predetermined first set period;
making the ultraviolet light source interrupt the irradiation of the ultraviolet light in a case where determination is made that the set condition is satisfied before the first set period elapses; and
making the ultraviolet light source restart the irradiation of the ultraviolet light in a case where determination is made that the set condition is not satisfied within a predetermined second set period after the irradiation of the ultraviolet light is interrupted.

* * * * *